United States Patent
Jordan et al.

(10) Patent No.: US 11,661,423 B2
(45) Date of Patent: *May 30, 2023

(54) HETEROCYCLIC COMPOUNDS AS RET KINASE INHIBITORS

(71) Applicant: Cancer Research Technology Limited, London (GB)

(72) Inventors: Allan Michael Jordan, Manchester (GB); Rebecca Newton, Manchester (GB); Bohdan Waszkowycz, Manchester (GB); Jonathan Mark Sutton, Harlow (GB); George Hynd, Harlow (GB); Silvia Paoletta, Nottingham (GB); Euan Alexander Fraser Fordyce, Nottingham (GB)

(73) Assignee: Cancer Research Technology Limited, London (GB)

( * ) Notice: Subject to any disclaimer, the term of this patent is extended or adjusted under 35 U.S.C. 154(b) by 197 days.

This patent is subject to a terminal disclaimer.

(21) Appl. No.: 17/075,004

(22) Filed: Oct. 20, 2020

(65) Prior Publication Data

US 2021/0047334 A1 Feb. 18, 2021

Related U.S. Application Data

(63) Continuation of application No. 16/093,858, filed as application No. PCT/GB2017/051077 on Apr. 18, 2017, now Pat. No. 10,844,067.

(30) Foreign Application Priority Data

Apr. 15, 2016 (GB) ...................... 1606635

(51) Int. Cl.
| | |
|---|---|
| *C07D 487/04* | (2006.01) |
| *A61P 35/00* | (2006.01) |
| *C07D 471/04* | (2006.01) |
| *C07D 519/00* | (2006.01) |

(52) U.S. Cl.
CPC ............ *C07D 487/04* (2013.01); *A61P 35/00* (2018.01); *C07D 471/04* (2013.01); *C07D 519/00* (2013.01)

(58) Field of Classification Search
CPC .. C07D 487/04; C07D 471/04; C07D 519/00; A61P 35/00
See application file for complete search history.

(56) References Cited

U.S. PATENT DOCUMENTS

| | | |
|---|---|---|
| 5,055,464 A | 10/1991 | Murakami et al. |
| 5,646,153 A | 7/1997 | Spada et al. |
| 7,429,596 B2 | 9/2008 | Tanaka et al. |
| 7,772,231 B2 | 8/2010 | Sheppard et al. |
| 7,923,555 B2 | 4/2011 | Chen et al. |
| 8,314,111 B2 | 11/2012 | Chen et al. |
| 8,501,724 B1 | 8/2013 | Chen et al. |
| 8,796,455 B2 | 8/2014 | Chen et al. |
| 8,901,134 B2 | 12/2014 | Bloomfield et al. |
| 9,096,611 B2 | 8/2015 | Ren et al. |
| 9,174,994 B2 | 11/2015 | Liu et al. |
| 9,271,963 B2 | 3/2016 | Hartmann et al. |
| 9,358,229 B2 | 6/2016 | Vannucchi et al. |
| 9,409,911 B2 | 8/2016 | Honigberg et al. |
| 9,512,125 B2 | 12/2016 | Shokat et al. |
| 9,629,843 B2 | 4/2017 | Shokat et al. |
| 9,669,032 B2 | 6/2017 | Liu et al. |
| 9,724,354 B2 | 8/2017 | Brake et al. |
| 9,738,610 B2 | 8/2017 | Vincent et al. |
| 9,765,037 B2 | 9/2017 | Van Voorhis et al. |

(Continued)

FOREIGN PATENT DOCUMENTS

| | | |
|---|---|---|
| CN | 101316845 A | 12/2008 |
| EP | 2528919 B1 | 11/2016 |

(Continued)

OTHER PUBLICATIONS

Golub, T. R., "Molecular classification of cancer: class discovery and class prediction by gene expression monitoring." Science 286.5439 (1999): 531-537.*

(Continued)

*Primary Examiner* — John M Mauro
(74) *Attorney, Agent, or Firm* — McNeill Baur PLLC

(57) ABSTRACT

The present invention relates to compounds of formula I that function as inhibitors of RET (rearranged during transfection) kinase enzyme activity: wherein HET, $X_1$, $X_2$, $X_3$, $X_4$, integer a and $R_3$ are each as defined herein. The present invention also relates to processes for the preparation of these compounds, to pharmaceutical compositions comprising them, and to their use in the treatment of proliferative disorders, such as cancer, as well as other diseases or conditions in which RET kinase activity is implicated.

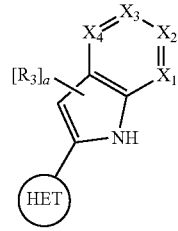

Formula I

24 Claims, No Drawings

(56) References Cited

U.S. PATENT DOCUMENTS

| | | | |
|---|---|---|---|
| 9,828,378 | B2 | 11/2017 | Ren et al. |
| 10,844,067 | B2 * | 11/2020 | Jordan .................. C07D 471/04 |
| 2008/0064878 | A1 | 3/2008 | Aoki et al. |
| 2009/0274698 | A1 | 11/2009 | Bhagwat et al. |
| 2009/0312319 | A1 | 12/2009 | Ren et al. |
| 2011/0224223 | A1 * | 9/2011 | Shokat .................... A61P 35/00 |
| | | | 435/375 |
| 2011/0281866 | A1 | 11/2011 | Ren et al. |
| 2013/0018040 | A1 | 1/2013 | Van Voorhis et al. |
| 2014/0357651 | A1 | 12/2014 | Liu et al. |
| 2014/0377285 | A1 | 12/2014 | Liu et al. |
| 2016/0272645 | A1 | 9/2016 | Rai et al. |
| 2017/0327506 | A1 | 11/2017 | Buffa et al. |
| 2019/0106425 | A1 | 4/2019 | Jordan et al. |
| 2019/0263819 | A1 | 8/2019 | Jordan et al. |

FOREIGN PATENT DOCUMENTS

| | | |
|---|---|---|
| WO | 2005077954 A2 | 8/2005 |
| WO | 2007061737 A2 | 5/2007 |
| WO | 2007064993 A2 | 6/2007 |
| WO | 2007079164 A3 | 9/2007 |
| WO | 2009088990 A1 | 7/2009 |
| WO | 2010006072 A2 | 1/2010 |
| WO | 2010006086 A2 | 1/2010 |
| WO | 2010036380 A1 | 4/2010 |
| WO | 2010059593 A1 | 5/2010 |
| WO | 2010064875 A2 | 6/2010 |
| WO | 2011008302 A1 | 1/2011 |
| WO | 2011055215 A2 | 5/2011 |
| WO | 2011094628 A1 | 8/2011 |
| WO | 2011153553 A2 | 12/2011 |
| WO | 2012006619 A2 | 1/2012 |
| WO | 2012148540 A1 | 11/2012 |
| WO | 2012151562 A1 | 11/2012 |
| WO | 2013070976 A1 | 5/2013 |
| WO | 2013077921 A2 | 5/2013 |
| WO | 2013078440 A2 | 5/2013 |
| WO | 2013116382 A1 | 8/2013 |
| WO | 2013153479 A2 | 10/2013 |
| WO | 2014047662 A2 | 3/2014 |
| WO | 2014049364 A1 | 4/2014 |
| WO | 2014151147 A1 | 9/2014 |
| WO | 2014153509 A1 | 9/2014 |
| WO | 2015058084 A1 | 4/2015 |
| WO | 2015079251 A1 | 6/2015 |
| WO | 2016075224 A1 | 5/2016 |
| WO | 2016123151 A1 | 8/2016 |
| WO | 2017027883 A1 | 2/2017 |
| WO | 2017160717 A2 | 9/2017 |
| WO | 2017178844 A1 | 10/2017 |
| WO | 2017178845 A1 | 10/2017 |

OTHER PUBLICATIONS

Sawyers, C., "Targeted cancer therapy." Nature 432.7015 (2004): 294-297.*
Mologni, L., "Ponatinib is a potent inhibitor of wild-type and drug-resistant gatekeeper mutant RET kinase." Molecular and cellular endocrinology 377.1-2 (2013): 1-6.*
CAS Registry No. 950187-48-1 (Database Registry Chemical Abstracts Service, Columbus, OH) entered Oct. 11, 2007, p. 1.*
G. Malcolm Dyson, "May's Chemistry of Synthetic Drugs," Fifth Edition, 11 pages (1959) (partial translation).
Carlomagno et al., "Disease associated mutations at valine 804 in the RET receptor tyrosine kinase confer resistance to selective kinase inhibitors," Oncogene 23, 6056-6063, (2004).
Chao et al., "RET fusion genes in Non-Small-Cell Lung Cancer," JCO 30, 4439-4441, (2012).
Daley, et al., "Transformation of an interleukin 3-dependent hematopoietic cell line by the chronic myelogenous leukemia-specific P210bcr/abl protein," Proc. Natl. Acad. Sci. USA, 85, 9312-16, (1988).

Dinér et al., "Preparation of 3-Substituted-1-Isopropyl-1H-pyrazolo[3,4-d]pyrimidin-4-amines as RET Kinase Inhibitors," J Med Chem 55 (10) 4872-6, (2012).
Elisei et al., "Prognostic Significance of Somatic RET Oncogene Mutations in Sporadic Medullary Thyroid Cancer: A 10-Year Follow-Up Study," Journal of Clinical Endocrinology and Metabolism 93(3), 682-687, (2008).
Elisei et al., "RET genetic screening in patients with medullary thyroid cancer and their relatives: experience with 807 individuals at one center," Journal of Clinical Endocrinology and Metabolism 92(12), 4725-4729 (2007).
Examination Report issued in corresponding European Application No. 17719688.8, dated Mar. 27, 2020, 3 pages.
International Search Report and Written Opinion for International Application No. PCT/GB2017/051076 dated May 30, 2017.
International Search Report and Written Opinion for International Application No. PCT/GB2017/051077 dated May 30, 2017.
International Search Report and Written Opinion for International Application No. PCT/GB2018/050986 dated Jun. 4, 2018; 13 pages.
Ju et al., "A transforming KIF5B and RET gene fusion in lung adenocarcinoma revealed from whole-genome and transcriptome sequencing," Genome Res. 22, 436-445, (2012).
Kohno et al., "KIF5B-RET fusions in lung adenocarcinoma," Nat Med. 12, 375-377, (2012).
Lipson et al. "Identification of new ALK and RET gene fusions from colorectal and lung cancer biopsies," Nat Med. 12, 382-384, (2012).
Matsubara et al., "Identification of CCDC6-RET fusion in the human lung adenocarcinoma cell line, LC-2/ad," J Thorac Oncol. 12, 1872-6, (2012).
Nagilla et al., "Cabozantinib for the treatment of Advanced Medullary Thyroid Cancer," Adv Ther 11, 925-934, (2012).
Pitt, S.C. et al., "The Phosphatidylinositol 3-Kinase/Akt Signaling Pathway in Medullary Thyroid Cancer," Surgery, 144(5), pp. 721-724 (2008).
Santoro et al., "Drug insight: Small-molecule inhibitors of protein kinases in the treatment of thyroid cancer," Nature Clinical Practice: Endocrinology and Metabolism 2, 42-52, (2006).
Schlumberger et al., "New therapeutic approaches to treat medullary thyroid carcinoma," Nat Clin Pract Endocrinol Metab, 4(1), pp. 22-32 (2008).
UK Search Report for Application No. GB1606631.8 dated Jan. 27, 2017.
UK Search Report for Application No. GB1606635.9 dated Jan. 27, 2017.
Verbeek et al., "The effects of four different tyrosine kinase inhibitors on medullary and papillary thyroid cancer cells," J Clin Endocrinol Metab. 96, 2010-2381, (2011).
Vitagliano et al., "The tyrosine inhibitor ZD6474 blocks proliferation of RET mutant medullary thyroid carcinoma cells," Endocrine-related Cancer 18, 1-11, (2011).
Wang et al., "RET fusions define a unique molecular and clinicopathologic subtype of non-small-cell lung cancer," JCO 30, 4352-4359, (2012).
Wells et al., "Vandetanib in patients with locally advanced or metastatic medullary thyroid cancer: a randomized, double-blind phase III trial," JCO 10, 134-141, (2012).
Wells et al., "Targeting the RET pathway in thyroid cancer," Clin Can Res. 15, 7119-7123, (2009).
Acute Leukemia, Merck Manual (Online Edition) 6 pages, pp. 1-6 (2013).
Apsel et al., "Targeted polypharmacology: discovery of dual inhibitors of tyrosine and phosphoinositide kinases," Nature Chemical Biology (4)(11); pp. 691-699 (2008).
Gura, "Systems for Identifying New Drugs Are Often Faulty," Cancer Models, Science, vol. 278, No. 5340, pp. 1041-1042, (1997).
Johnson et al., "Relationships between drug activity in NCI preclinical in vitro and in vivo models and early clinical trials," British Journal of Cancer 64(10): 1424-1431, (2001).

(56) References Cited

OTHER PUBLICATIONS

Pearce et al., "Failure modes in anticancer drug discovery and development," Cancer Drug Design and Discovery Chapter 18, pp. 424-435 (2008).
Simone, "Oncology: Introduction," Cecil Textbook of Medicine, 20th Edition, vol. 1, pp. 1004-1010 (1996).

* cited by examiner

HETEROCYCLIC COMPOUNDS AS RET KINASE INHIBITORS

CROSS-REFERENCE TO RELATED APPLICATIONS

This application is a continuation of U.S. patent application Ser. No. 16/093,858, which adopts the international filing date of Apr. 18, 2017, which is a national phase entry pursuant to 35 U.S.C. § 371 of International Application No. PCT/GB2017/051077, filed Apr. 18, 2017, which claims the benefit of priority to United Kingdom Patent Application No. GB 1606635.9, filed Apr. 15, 2016, the disclosure of each of which is incorporated herein by reference in its entirety.

INTRODUCTION

The present invention relates to certain compounds that function as inhibitors of RET (rearranged during transfection) kinase enzyme activity. The present invention also relates to processes for the preparation of these compounds, to pharmaceutical compositions comprising them, and to their use in the treatment of proliferative disorders, such as cancer, as well as other diseases or conditions in which RET kinase activity is implicated.

BACKGROUND OF THE INVENTION

Cancer is caused by uncontrolled and unregulated cellular proliferation. Precisely what causes a cell to become malignant and proliferate in an uncontrolled and unregulated manner has been the focus of intense research over recent decades. This research has led to the identification of a number of molecular targets associated with key metabolic pathways that are known to be associated with malignancy.

RET (REarranged during Transfection) is a receptor tyrosine kinase (RTK) that forms part of a macromolecular receptor complex containing dimerized RET receptor, two co-receptors and a bound ligand. The glial derived neurotrophic factor (GDNF) family of ligands bind RET in association with one of four glycosyl phosphatidylinositol (GPI) anchored GDNF family α-receptors (GFRα). Ligand binding to the corresponding GFRα co-receptor triggers RET dimerization followed by trans-phosphorylation of intracellular signalling cascades. These downstream signalling networks play a key role in regulating cell survival, differentiation, proliferation, migration and chemotaxis.

Activating mutations in RET have been identified in familial and sporadic forms of medullary thyroid carcinomas (MTC) (Santoro & Carlomagno 2006; Schulmberger et al. 2008; Wells & Santoro 2009) and these correlate with aggressive disease progression (Elisei et al. 2008). Clinical benefit has been observed in MTC patients using the small molecule VEGFR2/EGFR inhibitor vandetanib (Wells et al. 2011) which has recently been approved by the FDA & EMEA. RET inhibition is a secondary pharmacology of this agent, which also targets VEGFR2 (Vascular endothelial growth factor receptor, also known as KDR—kinase insert domain receptor) and EGFR (epidermal growth factor receptor). The clinical benefit in MTC is considered to be due to RET inhibition but is unfortunately accompanied by significant side effects (rash, hypertension, diarrhoea) due to inhibition of EGFR and/or VEGFR. Furthermore, vandetanib also exhibits off-target activity versus hERG. Collectively all of these unwanted pharmacological activities may compromise its use in advanced MTC and also its extrapolation into earlier clinical settings (e.g. adjuvant).

Furthermore, several recent publications (Ju et al., 2012; Lipson et al., 2012; Kohno et al., 2012; Wang et al., 2012; Chao et al., 2012) describe various RET fusion translocations (e.g. KIF5B-RET and CCDC6-RET) present in approximately 1% of NSCLC (non-small cell lung carcinoma) patient samples, which may offer an important alternative disease segment in which a specific RET inhibitor would offer clinical benefit.

Therefore, there is a requirement for the development of more selective inhibitors of RET, in particular inhibitors that show less inhibition of KDR. It is anticipated that these more selective inhibitors will produce the desired therapeutic benefits associated with RET inhibition without the side effects associated with significant KDR inhibition. Such inhibitors will offer the potential of better therapy for cancers such as MTC and NSCLC and will widen the scope for the clinical use of RET inhibitors in earlier disease settings.

It is therefore an object of the present invention to provide further inhibitors of RET kinase enzyme activity.

Another object of the present invention is to provide inhibitors of RET kinase enzyme activity that show a greater selectivity for the inhibition of RET kinase relative to the inhibition of KDR.

SUMMARY OF THE INVENTION

According to a first aspect of the present invention, there is provided a compound, or a pharmaceutically acceptable salt, hydrate or solvate thereof, as defined herein.

According to a further aspect of the present invention, there is provided a pharmaceutical composition comprising a compound as defined herein, or a pharmaceutically acceptable salt, hydrate or solvate thereof, in admixture with a pharmaceutically acceptable diluent or carrier.

According to a further aspect of the present invention, there is provided a method of inhibiting RET kinase enzyme activity, or mutant forms thereof (e.g. $RET^{V804M}$), in vitro or in vivo, said method comprising contacting a cell with an effective amount of a compound or a pharmaceutically acceptable salt, hydrate or solvate thereof as defined herein.

According to a further aspect of the present invention, there is provided a method of selectively inhibiting RET kinase enzyme activity, or mutant forms thereof (e.g. $RET^{V804M}$), over KDR enzyme activity in vitro or in vivo, said method comprising contacting a cell with an effective amount of a compound, or a pharmaceutically acceptable salt, hydrate or solvate thereof, as defined herein.

According to a further aspect of the present invention, there is provided a method of inhibiting cell proliferation, in vitro or in vivo, said method comprising contacting a cell with an effective amount of a compound or a pharmaceutically acceptable salt, hydrate or solvate thereof as defined herein, or a pharmaceutical composition as defined herein.

According to a further aspect of the present invention, there is provided a method of treating a disease or disorder in which RET kinase activity is implicated in a patient in need of such treatment, said method comprising administering to said patient a therapeutically effective amount of a compound or a pharmaceutically acceptable salt, hydrate or solvate thereof as defined herein, or a pharmaceutical composition as defined herein.

According to a further aspect of the present invention, there is provided a method of treating a proliferative disorder in a patient in need of such treatment, said method comprising administering to said patient a therapeutically effective amount of a compound or a pharmaceutically acceptable salt, hydrate or solvate thereof as defined herein, or a pharmaceutical composition as defined herein.

According to a further aspect of the present invention, there is provided a method of treating cancer in a patient in need of such treatment, said method comprising administering to said patient a therapeutically effective amount of a compound or a pharmaceutically acceptable salt, hydrate or solvate thereof as defined herein, or a pharmaceutical composition as defined herein.

According to a further aspect of the present invention, there is provided a compound, or a pharmaceutically acceptable salt, hydrate or solvate thereof, or a pharmaceutical composition as defined herein for use in therapy.

According to a further aspect of the present invention, there is provided a compound or a pharmaceutically acceptable salt, hydrate or solvate thereof as defined herein, or a pharmaceutical composition as defined herein, for use in the treatment of a proliferative condition.

According to a further aspect of the present invention, there is provided a compound, or a pharmaceutically acceptable salt, hydrate or solvate thereof, or a pharmaceutical composition as defined herein for use in the treatment of cancer. In a particular embodiment, the cancer is human cancer.

According to a further aspect of the present invention, there is provided a compound, or a pharmaceutically acceptable salt, hydrate or solvate thereof, as defined herein for use in the inhibition of RET kinase enzyme activity, or mutant forms thereof (e.g. $RET^{V804M}$).

According to a further aspect of the present invention, there is provided a compound, or a pharmaceutically acceptable salt, hydrate or solvate thereof, as defined herein for use in the selective inhibition of RET kinase enzyme activity, or mutant forms thereof (e.g. $RET^{V804M}$), relative to KDR enzyme activity.

According to a further aspect of the present invention, there is provided a compound, or a pharmaceutically acceptable salt, hydrate or solvate thereof, as defined herein for use in the treatment of a disease or disorder in which RET kinase activity, or mutant forms thereof (e.g. $RET^{V804M}$), is implicated.

According to a further aspect of the present invention, there is provided the use of a compound, or a pharmaceutically acceptable salt, hydrate or solvate thereof, as defined herein in the manufacture of a medicament for the treatment of a proliferative condition.

Suitably, the proliferative disorder is cancer, suitably a human cancer (for example medullary thyroid cancer (MTC) or non-small cell lung cancer).

According to a further aspect of the present invention, there is provide the use of a compound, or a pharmaceutically acceptable salt, hydrate or solvate thereof, as defined herein in the manufacture of a medicament for the treatment of cancer.

According to a further aspect of the present invention, there is provided a use of a compound, or a pharmaceutically acceptable salt, hydrate or solvate thereof, as defined herein in the manufacture of a medicament for the inhibition of RET kinase enzyme activity, or mutant forms thereof (e.g. $RET^{V804M}$).

According to a further aspect of the present invention, there is provided a use of a compound, or a pharmaceutically acceptable salt, hydrate or solvate thereof, as defined herein in the manufacture of a medicament for the selective inhibition of RET kinase enzyme activity, or mutant forms thereof (e.g. $RET^{V804M}$), relative to KDR enzyme activity.

According to a further aspect of the present invention, there is provided a use of a compound, or a pharmaceutically acceptable salt, hydrate or solvate thereof, as defined herein in the manufacture of a medicament for the treatment of a disease or disorder in which RET kinase activity, or mutant forms thereof (e.g. $RET^{V804M}$), is implicated.

According to a further aspect of the present invention, there is provided a process for preparing a compound, or a pharmaceutically acceptable salt, hydrate or solvate thereof, as defined herein.

According to a further aspect of the present invention, there is provided a compound, or a pharmaceutically acceptable salt, hydrate or solvate thereof, obtainable by, or obtained by, or directly obtained by a process of preparing a compound as defined herein.

According to a further aspect of the present invention, there are provided novel intermediates as defined herein which are suitable for use in any one of the synthetic methods set out herein.

Features, including optional, suitable, and preferred features in relation to one aspect of the invention may also be features, including optional, suitable and preferred features in relation to any other aspect of the invention.

DETAILED DESCRIPTION OF THE INVENTION

Definitions

Unless otherwise stated, the following terms used in the specification and claims have the following meanings set out below.

It is to be appreciated that references to "treating" or "treatment" include prophylaxis as well as the alleviation of established symptoms of a condition. "Treating" or "treatment" of a state, disorder or condition therefore includes: (1) preventing or delaying the appearance of clinical symptoms of the state, disorder or condition developing in a human that may be afflicted with or predisposed to the state, disorder or condition but does not yet experience or display clinical or subclinical symptoms of the state, disorder or condition, (2) inhibiting the state, disorder or condition, i.e., arresting, reducing or delaying the development of the disease or a relapse thereof (in case of maintenance treatment) or at least one clinical or subclinical symptom thereof, or (3) relieving or attenuating the disease, i.e., causing regression of the state, disorder or condition or at least one of its clinical or subclinical symptoms.

A "therapeutically effective amount" means the amount of a compound that, when administered to a mammal for treating a disease, is sufficient to effect such treatment for the disease. The "therapeutically effective amount" will vary depending on the compound, the disease and its severity and the age, weight, etc., of the mammal to be treated.

In this specification the term "alkyl" includes both straight and branched chain alkyl groups. References to individual alkyl groups such as "propyl" are specific for the straight chain version only and references to individual branched chain alkyl groups such as "isopropyl" are specific for the branched chain version only. For example, "(1-6C)alkyl" includes (1-4C)alkyl, (1-3C)alkyl, propyl, isopropyl and t-butyl. A similar convention applies to other radicals, for example "phenyl(1-6C)alkyl" includes phenyl(1-4C)alkyl, benzyl, 1-phenylethyl and 2-phenylethyl.

The term "(m-nC)" or "(m-nC) group" used alone or as a prefix, refers to any group having m to n carbon atoms.

An "alkylene," "alkenylene," or "alkynylene" group is an alkyl, alkenyl, or alkynyl group that is positioned between and serves to connect two other chemical groups. Thus, "(1-6C)alkylene" means a linear saturated divalent hydrocarbon radical of one to six carbon atoms or a branched saturated divalent hydrocarbon radical of three to six carbon atoms, for example, methylene, ethylene, propylene, 2-methylpropylene, pentylene, and the like.

"(2-6C)alkenylene" means a linear divalent hydrocarbon radical of two to six carbon atoms or a branched divalent hydrocarbon radical of three to six carbon atoms, containing at least one double bond, for example, as in ethenylene, 2,4-pentadienylene, and the like.

"(2-6C)alkynylene" means a linear divalent hydrocarbon radical of two to six carbon atoms or a branched divalent hydrocarbon radical of three to six carbon atoms, containing at least one triple bond, for example, as in ethynylene, propynylene, and butynylene and the like.

"(3-8C)cycloalkyl" means a hydrocarbon ring containing from 3 to 8 carbon atoms, for example, cyclopropyl, cyclobutyl, cyclopentyl, cyclohexyl, cycloheptyl or bicyclo[2.2.1]heptyl.

"(3-8C)cycloalkenyl" means a hydrocarbon ring containing from 3 to 8 carbon atoms and at least one double bond, for example, cyclobutenyl, cyclopentenyl, cyclohexenyl or cycloheptenyl, such as 3-cyclohexen-1-yl, or cyclooctenyl.

"(3-8C)cycloalkyl-(1-6C)alkylene" means a (3-8C)cycloalkyl group covalently attached to a (1-6C)alkylene group, both of which are defined herein.

The term "halo" or "halogeno" refers to fluoro, chloro, bromo and iodo.

The term "heterocyclyl", "heterocyclic" or "heterocycle" means a non-aromatic saturated or partially saturated monocyclic, fused, bridged, or spiro bicyclic heterocyclic ring system(s). Monocyclic heterocyclic rings contain from about 3 to 12 (suitably from 3 to 7) ring atoms, with from 1 to 5 (suitably 1, 2 or 3) heteroatoms selected from nitrogen, oxygen or sulfur in the ring. Bicyclic heterocycles contain from 7 to 17 member atoms, suitably 7 to 12 member atoms, in the ring. Bicyclic heterocyclic(s) rings may be fused, spiro, or bridged ring systems. Examples of heterocyclic groups include cyclic ethers such as oxiranyl, oxetanyl, tetrahydrofuranyl, dioxanyl, and substituted cyclic ethers. Heterocycles containing nitrogen include, for example, azetidinyl, pyrrolidinyl, piperidinyl, piperazinyl, tetrahydrotriazinyl, tetrahydropyrazolyl, and the like. Typical sulfur containing heterocycles include tetrahydrothienyl, dihydro-1,3-dithiol, tetrahydro-2H-thiopyran, and hexahydrothiepine. Other heterocycles include dihydro-oxathiolyl, tetrahydro-oxazolyl, tetrahydro-oxadiazolyl, tetrahydrodioxazolyl, tetrahydro-oxathiazolyl, hexahydrotriazinyl, tetrahydro-oxazinyl, morpholinyl, thiomorpholinyl, tetrahydropyrimidinyl, dioxolinyl, octahydrobenzofuranyl, octahydrobenzimidazolyl, and octahydrobenzothiazolyl. For heterocycles containing sulfur, the oxidized sulfur heterocycles containing SO or $SO_2$ groups are also included. Examples include the sulfoxide and sulfone forms of tetrahydrothienyl and thiomorpholinyl such as tetrahydrothiene 1,1-dioxide and thiomorpholinyl 1,1-dioxide. A suitable value for a heterocyclyl group which bears 1 or 2 oxo (=O) or thioxo (=S) substituents is, for example, 2-oxopyrrolidinyl, 2-thioxopyrrolidinyl, 2-oxoimidazolidinyl, 2-thioxoimidazolidinyl, 2-oxopiperidinyl, 2,5-dioxopyrrolidinyl, 2,5-dioxoimidazolidinyl or 2,6-dioxopiperidinyl. Particular heterocyclyl groups are saturated monocyclic 3 to 7 membered heterocyclyls containing 1, 2 or 3 heteroatoms selected from nitrogen, oxygen or sulfur, for example azetidinyl, tetrahydrofuranyl, tetrahydropyranyl, pyrrolidinyl, morpholinyl, tetrahydrothienyl, tetrahydrothienyl 1,1-dioxide, thiomorpholinyl, thiomorpholinyl 1,1-dioxide, piperidinyl, homopiperidinyl, piperazinyl or homopiperazinyl. As the skilled person would appreciate, any heterocycle may be linked to another group via any suitable atom, such as via a carbon or nitrogen atom. However, reference herein to piperidino or morpholino refers to a piperidin-1-yl or morpholin-4-yl ring that is linked via the ring nitrogen.

By "bridged ring systems" is meant ring systems in which two rings share more than two atoms, see for example *Advanced Organic Chemistry*, by Jerry March, 4$^{th}$ Edition, Wiley Interscience, pages 131-133, 1992. Examples of bridged heterocyclyl ring systems include, aza-bicyclo[2.2.1]heptane, 2-oxa-5-azabicyclo[2.2.1]heptane, aza-bicyclo[2.2.2]octane, aza-bicyclo[3.2.1]octane and quinuclidine.

By "spiro bi-cyclic ring systems" we mean that the two ring systems share one common spiro carbon atom, i.e. the heterocyclic ring is linked to a further carbocyclic or heterocyclic ring through a single common spiro carbon atom. Examples of spiro ring systems include 6-azaspiro[3.4]octane, 2-oxa-6-azaspiro[3.4]octane, 2-azaspiro[3.3]heptanes, 2-oxa-6-azaspiro[3.3]heptanes, 7-oxa-2-azaspiro[3.5]nonane, 6-oxa-2-azaspiro[3.4]octane, 2-oxa-7-azaspiro[3.5]nonane and 2-oxa-6-azaspiro[3.5]nonane.

"Heterocyclyl(1-6C)alkyl" means a heterocyclyl group covalently attached to a (1-6C)alkylene group, both of which are defined herein.

The term "heteroaryl" or "heteroaromatic" means an aromatic mono-, bi-, or polycyclic ring incorporating one or more (for example 1-4, particularly 1, 2 or 3) heteroatoms selected from nitrogen, oxygen or sulfur. The term heteroaryl includes both monovalent species and divalent species. Examples of heteroaryl groups are monocyclic and bicyclic groups containing from five to twelve ring members, and more usually from five to ten ring members. The heteroaryl group can be, for example, a 5-or 6-membered monocyclic ring or a 9-or 10-membered bicyclic ring, for example a bicyclic structure formed from fused five and six membered rings or two fused six membered rings. Each ring may contain up to about four heteroatoms typically selected from nitrogen, sulfur and oxygen. Typically the heteroaryl ring will contain up to 3 heteroatoms, more usually up to 2, for example a single heteroatom. In one embodiment, the heteroaryl ring contains at least one ring nitrogen atom. The nitrogen atoms in the heteroaryl rings can be basic, as in the case of an imidazole or pyridine, or essentially non-basic as in the case of an indole or pyrrole nitrogen. In general the number of basic nitrogen atoms present in the heteroaryl group, including any amino group substituents of the ring, will be less than five.

Examples of heteroaryl include furyl, pyrrolyl, thienyl, oxazolyl, isoxazolyl, imidazolyl, pyrazolyl, thiazolyl, isothiazolyl, oxadiazolyl, thiadiazolyl, triazolyl, tetrazolyl, pyridyl, pyridazinyl, pyrimidinyl, pyrazinyl, 1,3,5-triazenyl, benzofuranyl, indolyl, isoindolyl, benzothienyl, benzoxazolyl, benzimidazolyl, benzothiazolyl, benzothiazolyl, indazolyl, purinyl, benzofurazanyl, quinolyl, isoquinolyl, quinazolinyl, quinoxalinyl, cinnolinyl, pteridinyl, naphthyridinyl, carbazolyl, phenazinyl, benzisoquinolinyl, pyridopyrazinyl, thieno[2,3-b]furanyl, 2H-furo[3,2-b]-pyranyl, 5H-pyrido[2,3-d]-o-oxazinyl, 1H-pyrazolo[4,3-d]oxazolyl, 4H-imidazo[4,5-d]thiazolyl, pyrazino[2,3-d]pyridazinyl, imidazo[2,1-b]thiazolyl, imidazo[1,2-b][1,2,4]triazinyl. "Heteroaryl" also covers partially aromatic bi- or polycyclic ring systems wherein at least one ring is an aromatic ring and one or more of the other ring(s) is a non-aromatic, saturated or partially saturated ring, provided at least one ring contains one or more heteroatoms selected from nitrogen, oxygen or sulfur. Examples of partially aromatic heteroaryl groups include for example, tetrahydroisoquinolinyl, tetrahydroquinolinyl, 2-oxo-1,2,3,4-tetrahydroquinolinyl, dihydrobenzthienyl, dihydrobenzfuranyl, 2,3-dihydro-benzo[1,4]dioxinyl, benzo[1,3]dioxolyl, 2,2-dioxo-1,3-dihydro-2-benzothienyl, 4,5,6,7-tetrahydrobenzofuranyl, indolinyl, 1,2,3,4-tetrahydro-1,8-naphthyridinyl, 1,2,3,4-tetrahydropyrido[2,3-b]pyrazinyl and 3,4-dihydro-2H-pyrido[3,2-b][1,4]oxazinyl.

Examples of five membered heteroaryl groups include but are not limited to pyrrolyl, furanyl, thienyl, imidazolyl, furazanyl, oxazolyl, oxadiazolyl, oxatriazolyl, isoxazolyl, thiazolyl, isothiazolyl, pyrazolyl, triazolyl and tetrazolyl groups.

Examples of six membered heteroaryl groups include but are not limited to pyridyl, pyrazinyl, pyridazinyl, pyrimidinyl and triazinyl.

A bicyclic heteroaryl group may be, for example, a group selected from:
a benzene ring fused to a 5- or 6-membered ring containing 1, 2 or 3 ring heteroatoms;
a pyridine ring fused to a 5- or 6-membered ring containing 1, 2 or 3 ring heteroatoms;
a pyrimidine ring fused to a 5- or 6-membered ring containing 1 or 2 ring heteroatoms;
a pyrrole ring fused to a 5- or 6-membered ring containing 1, 2 or 3 ring heteroatoms;
a pyrazole ring fused to a 5- or 6-membered ring containing 1 or 2 ring heteroatoms;
a pyrazine ring fused to a 5- or 6-membered ring containing 1 or 2 ring heteroatoms;
an imidazole ring fused to a 5- or 6-membered ring containing 1 or 2 ring heteroatoms;
an oxazole ring fused to a 5- or 6-membered ring containing 1 or 2 ring heteroatoms;
an isoxazole ring fused to a 5- or 6-membered ring containing 1 or 2 ring heteroatoms;
a thiazole ring fused to a 5- or 6-membered ring containing 1 or 2 ring heteroatoms;
an isothiazole ring fused to a 5- or 6-membered ring containing 1 or 2 ring heteroatoms;
a thiophene ring fused to a 5- or 6-membered ring containing 1, 2 or 3 ring heteroatoms;
a furan ring fused to a 5- or 6-membered ring containing 1, 2 or 3 ring heteroatoms;
a cyclohexyl ring fused to a 5- or 6-membered heteroaromatic ring containing 1, 2 or 3 ring heteroatoms; and
a cyclopentyl ring fused to a 5- or 6-membered heteroaromatic ring containing 1, 2 or 3 ring heteroatoms.

Particular examples of bicyclic heteroaryl groups containing a six membered ring fused to a five membered ring include but are not limited to benzfuranyl, benzthiophenyl, benzimidazolyl, benzoxazolyl, benzisoxazolyl, benzthiazolyl, benzisothiazolyl, isobenzofuranyl, indolyl, isoindolyl, indolizinyl, indolinyl, isoindolinyl, purinyl (e.g., adeninyl, guaninyl), indazolyl, benzodioxolyl and pyrazolopyridinyl groups.

Particular examples of bicyclic heteroaryl groups containing two fused six membered rings include but are not limited to quinolinyl, isoquinolinyl, chromanyl, thiochromanyl, chromenyl, isochromenyl, chromanyl, isochromanyl, benzodioxanyl, quinolizinyl, benzoxazinyl, benzodiazinyl, pyridopyridinyl, quinoxalinyl, quinazolinyl, cinnolinyl, phthalazinyl, naphthyridinyl and pteridinyl groups.

"Heteroaryl(1-6C)alkyl" means a heteroaryl group covalently attached to a (1-6C)alkylene group, both of which are defined herein. Examples of heteroaralkyl groups include pyridin-3-ylmethyl, 3-(benzofuran-2-yl)propyl, and the like.

The term "aryl" means a cyclic or polycyclic aromatic ring having from 5 to 12 carbon atoms. The term aryl includes both monovalent species and divalent species. Examples of aryl groups include, but are not limited to, phenyl, biphenyl, naphthyl and the like. In particular embodiment, an aryl is phenyl.

The term "aryl(1-6C)alkyl" means an aryl group covalently attached to a (1-6C)alkylene group, both of which are defined herein. Examples of aryl-(1-6C)alkyl groups include benzyl, phenylethyl, and the like.

This specification also makes use of several composite terms to describe groups comprising more than one functionality. Such terms will be understood by a person skilled in the art. For example heterocyclyl(m-nC)alkyl comprises (m-nC)alkyl substituted by heterocyclyl.

The term "optionally substituted" refers to either groups, structures, or molecules that are substituted and those that are not substituted. The term "wherein a/any CH, $CH_2$, $CH_3$ group or heteroatom (i.e. NH) within a $R^1$ group is optionally substituted" suitably means that (any) one of the hydrogen radicals of the $R^1$ group is substituted by a relevant stipulated group.

Where optional substituents are chosen from "one or more" groups it is to be understood that this definition includes all substituents being chosen from one of the specified groups or the substituents being chosen from two or more of the specified groups.

The phrase "compound of the invention" means those compounds which are disclosed herein, both generically and specifically.

Compounds of the Invention

In one aspect, the present invention relates to compounds, or pharmaceutically acceptable salts, hydrates or solvates thereof, having the structural formula (I), shown below:

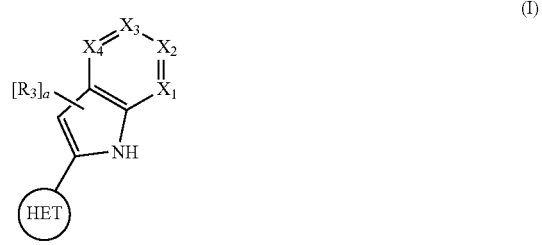

wherein:
HET is selected from one of the following:

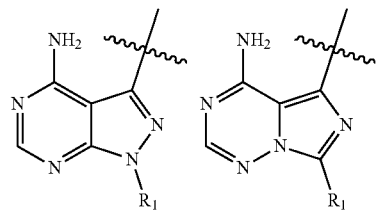

-continued

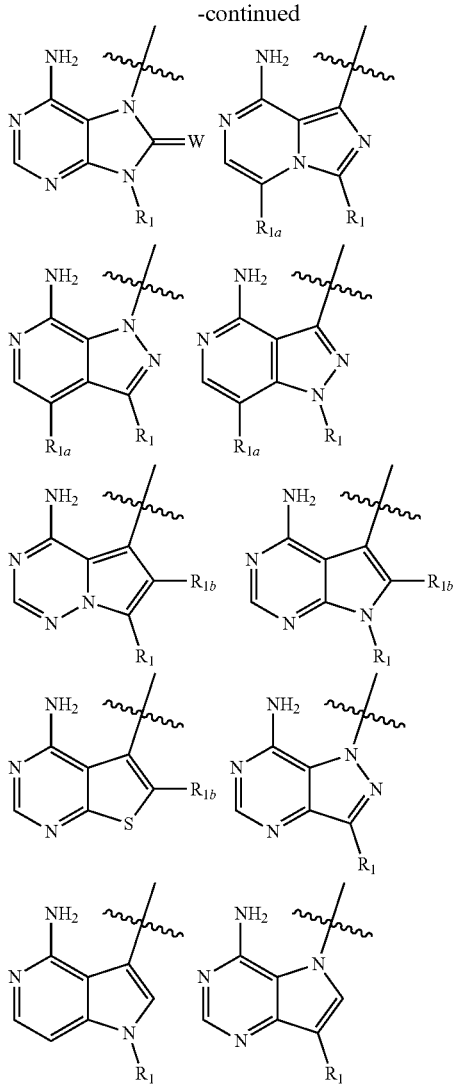

wherein

denotes the point of attachment;
R$_1$ is selected from hydrogen, (1-4C)haloalkyl, (1-4C)haloalkoxy or a group of the formula:

-L-Y-Q wherein:
L is absent or (1-5C)alkylene optionally substituted by one or more substituents selected from (1-2C)alkyl or oxo;
Y is absent or O, S, SO, SO$_2$, N(R$_a$), C(O), C(O)O, OC(O), C(O)N(R$_a$), N(R$_a$)C(O), N(R$_a$)C(O)N(R$_b$), N(R$_a$)C(O)O, OC(O)N(R$_a$), S(O)$_2$N(R$_a$), or N(R$_a$)SO$_2$, wherein R$_a$ and R$_b$ are each independently selected from hydrogen or (1-4C)alkyl; and
Q is hydrogen, (1-6C)alkyl, (2-6C)alkenyl, (2-6C)alkynyl, aryl, (3-10C)cycloalkyl, (3-10C)cycloalkenyl, heteroaryl or heterocyclyl; wherein Q is optionally further substituted by one or more substituent groups independently selected from (1-4C)alkyl, halo, (1-4C)haloalkyl, (1-4C)haloalkoxy, amino, (1-4C)aminoalkyl, cyano, hydroxy, carboxy, carbamoyl, sulphamoyl, mercapto, ureido, NR$_c$R$_d$, OR$_c$, C(O)R$_c$, C(O)OR$_c$, OC(O)R$_c$, C(O)N(R$_d$)R$_c$, N(R$_d$)C(O)R$_c$, S(O)$_p$R$_c$ (where p is 0, 1 or 2), SO$_2$N(R$_d$)R$_c$, N(R$_d$)SO$_2$R$_c$, Si(R$_e$)(R$_d$)R$_c$ or (CH$_2$)$_q$NR$_c$R$_d$ (where q is 1, 2 or 3); wherein R$_c$, R$_d$ and R$_e$ are each independently selected from hydrogen, (1-6C)alkyl or (3-6C)cycloalkyl; or R$_c$ and R$_d$ are linked such that, together with the nitrogen atom to which they are attached, they form a 4-7 membered heterocyclic ring which is optionally substituted by one or more substituents selected from (1-4C)alkyl, halo, (1-4C)haloalkyl, (1-4C)haloalkoxy, (1-4C)alkoxy, (1-4C)alkylamino, amino, cyano or hydroxy; or
Q is optionally substituted by a group of the formula:

-L$_1$-L$_{Q1}$-W$_1$ wherein:
L$_1$ is absent or (1-3C)alkylene optionally substituted by one or more substituents selected from (1-2C)alkyl or oxo;
L$_{Q1}$ is absent or selected from or O, S, SO, SO$_2$, N(R$_f$), C(O), C(O)O, OC(O), C(O)N(R$_f$), N(R$_f$)C(O), N(R$_f$)C(O)N(R$_g$), N(R$_f$)C(O)O, OC(O)N(R$_f$), S(O)$_2$N(R$_f$), or N(R$_f$)SO$_2$, wherein R$_f$ and R$_g$ are each independently selected from hydrogen or (1-2C)alkyl; and
W$_1$ is hydrogen, (1-6C)alkyl, aryl, aryl(1-2C)alkyl, (3-8C)cycloalkyl, (3-8C)cycloalkenyl, heteroaryl or heterocyclyl;
wherein W$_1$ is optionally substituted by one or more substituents selected from (1-4C)alkyl, halo, (1-4C)haloalkyl, (1-4C)haloalkoxy, (1-4C)alkoxy, (1-4C)alkylamino, amino, cyano, hydroxy, carboxy, carbamoyl, sulphamoyl, mercapto, ureido, aryl, heteroaryl, heterocycyl, (3-6C)cycloalkyl, NR$_h$R$_i$, OR$_h$, C(O)R$_h$, C(O)OR$_h$, OC(O)R$_h$, C(O)N(R$_i$)R$_h$, N(R$_i$)C(O)R$_h$, S(O)$_r$R$_h$ (where r is 0, 1 or 2), SO$_2$N(R$_i$)R$_h$, N(R$_i$)SO$_2$R$_h$ or (CH$_2$)$_s$NR$_i$R$_h$ (where s is 1, 2 or 3); wherein R$_h$ and R$_i$ are each independently selected from hydrogen, (1-4C)alkyl or (3-6C)cycloalkyl;
R$_{1a}$ and R$_{1b}$ are each selected from H, (1-4C)alkyl, halo, (1-4C)haloalkyl, (1-4C)haloalkoxy, (1-4C)alkoxy, (1-4C)alkylamino, amino, cyano, hydroxy, carboxy, carbamoyl, sulphamoyl or mercapto;
W is selected from O, S or NR$_{W1}$, wherein R$_{W1}$ is selected from H or (1-2C)alkyl
a is an integer selected from 0, 1 or 2;
X$_1$, X$_2$, X$_3$ and X$_4$ are independently selected from CH, CR$_2$ or N;
R$_2$ is selected from hydrogen, halo, (1-4C)alkyl, (1-4C)alkoxy, (1-4C)haloalkyl, (1-4C)haloalkoxy, amino, cyano, nitro, aryl, heteroaryl, heterocyclyl, cycloalkyl, (2-4C)alkynyl, NR$_j$R$_k$, OR$_j$, C(O)R$_j$, C(O)OR$_j$, OC(O)R$_j$, C(O)N(R$_k$)R$_j$, N(R$_k$)C(O)R$_j$, N(R$_k$)C(O)N(R$_j$), S(O)$_{r1}$R$_k$ (where r$_1$ is 0, 1 or 2), SO$_2$N(R$_j$)R$_k$, N(R$_j$)SO$_2$R$_k$ or (CH$_2$)$_v$NR$_j$R$_k$ (where v is 1, 2 or 3); wherein R$_j$ and R$_k$ are each independently selected from hydrogen or (1-4C)alkyl; and wherein said (1-4C)alkyl, aryl, heteroaryl, heterocycyl or cycloalkyl is optionally substituted by one or more substituents selected from halo, (1-4C)alkyl, (1-4C)alkoxy, (1-4C)haloalkyl, (1-4C)haloalkoxy, amino, cyano, nitro, phenyl, (2-4C)alkynyl, NR$_{j1}$R$_{k1}$, OR$_{j1}$, C(O)

$R_{j1}$, $C(O)OR_{j1}$, $OC(O)R_{j1}$, $C(O)N(R_{k1})R_{j1}$, $N(R_{k1})C(O)R_{j1}$, $S(O)_{r2}R_h$ (where $r_2$ is 0, 1 or 2), $SO_2N(R_{j1})R_{k1}$, $N(R_{j1})SO_2R_{k1}$ or $(CH_2)_{v1}NR_{j1}R_{k1}$ (where $v_1$ is 1, 2 or 3); and wherein $R_{j1}$ and $R_{k1}$ are each independently selected from hydrogen or (1-4C)alkyl; and $R_3$ is selected from hydrogen, halo, (1-4C)alkyl, (1-4C)alkoxy, (1-4C)haloalkyl, (1-4C)haloalkoxy, amino, cyano, nitro, (2-4C)alkynyl, $NR_lR_m$, $OR_l$, $C(O)R_l$, $C(O)OR_l$, $OC(O)R_l$, $C(O)N(R_m)R_l$, $N(R_m)C(O)R_l$, or $(CH_2)_yNR_lR_m$ (where y is 1, 2 or 3); wherein said (1-4C)alkyl is optionally substituted by one or more substituents selected from amino, hydroxy, (1-2C)alkoxy or halo; and wherein $R_l$ and $R_m$ are each independently selected from hydrogen or (1-4C)alkyl;

with the proviso that:

i) when the integer a is 0, $X_1$, $X_2$, $X_3$ and $X_4$ are CH and HET is of the formula shown below:

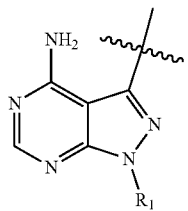

$R_1$ is not isopropyl, cyclobutyl, 2,3-dihydro-1H-inden-2-yl, 1,2,3,4-tetrahydro-2-naphthalenyl or 4-piperidinylmethyl; or ii) $R_1$ is not isopropyl when the integer a is 0, $X_2$ is CH, HET is of the formula shown below:

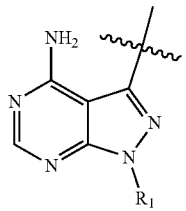

and:

a) $X_3$ is N and $X_1$ and $X_4$ are CH;
b) $X_1$ is N, $X_3$ is $COCH_3$ and $X_4$ is CH; or
c) $X_1$ is CH, $X_3$ is $COCH_3$ and $X_4$ is N;

iii) the compound is not 2-[4-amino-1-(propan-2-yl)-1H-pyrazolo[3,4-d]pyrimidin-3-yl]-1H-indol-5-ol; and iv) only one of $X_1$, $X_2$, $X_3$ or $X_4$ can be N.

Particular compounds of the invention include, for example, compounds of the Formula I, or pharmaceutically acceptable salts, hydrates and/or solvates thereof, wherein, unless otherwise stated, each of HET, $R_1$, $R_{1a}$, $R_{1b}$, W, integer a, $X_1$, $X_2$, $X_3$, $X_4$, $R_2$ and $R_3$ and any associated substituent groups has any of the meanings defined hereinbefore or in any of paragraphs (1) to (65) hereinafter:—

(1) HET is selected from one of the following:

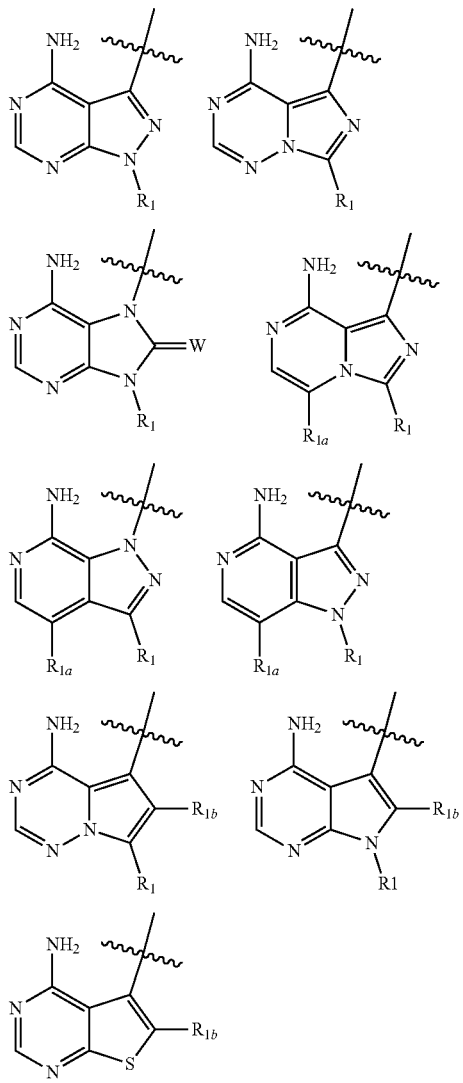

(2) HET is selected from one of the following:

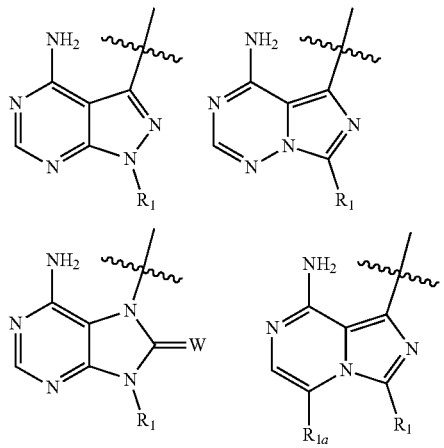

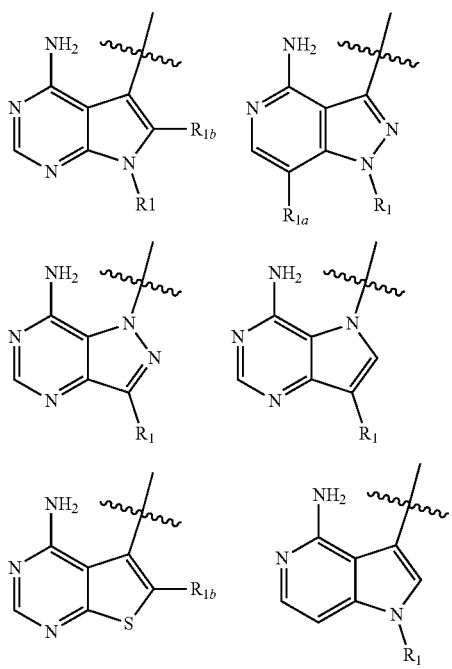
(3) HET is selected from one of the following:
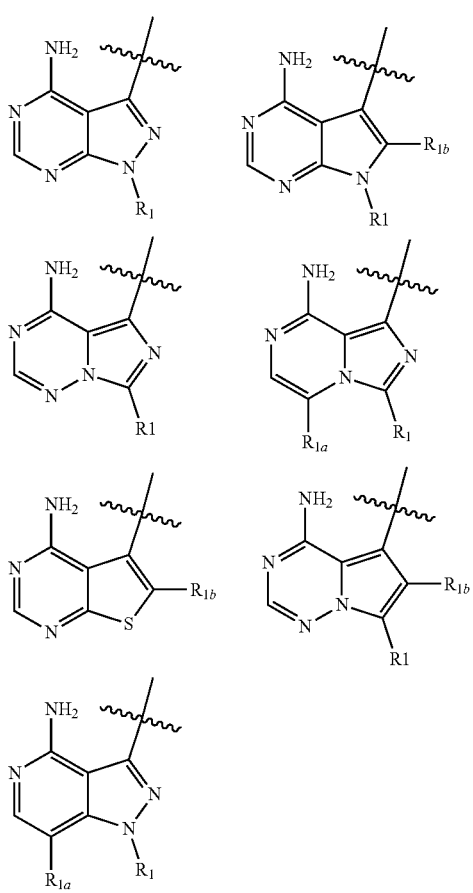
(4) HET is selected from one of the following:
(5) HET is selected from one of the following:
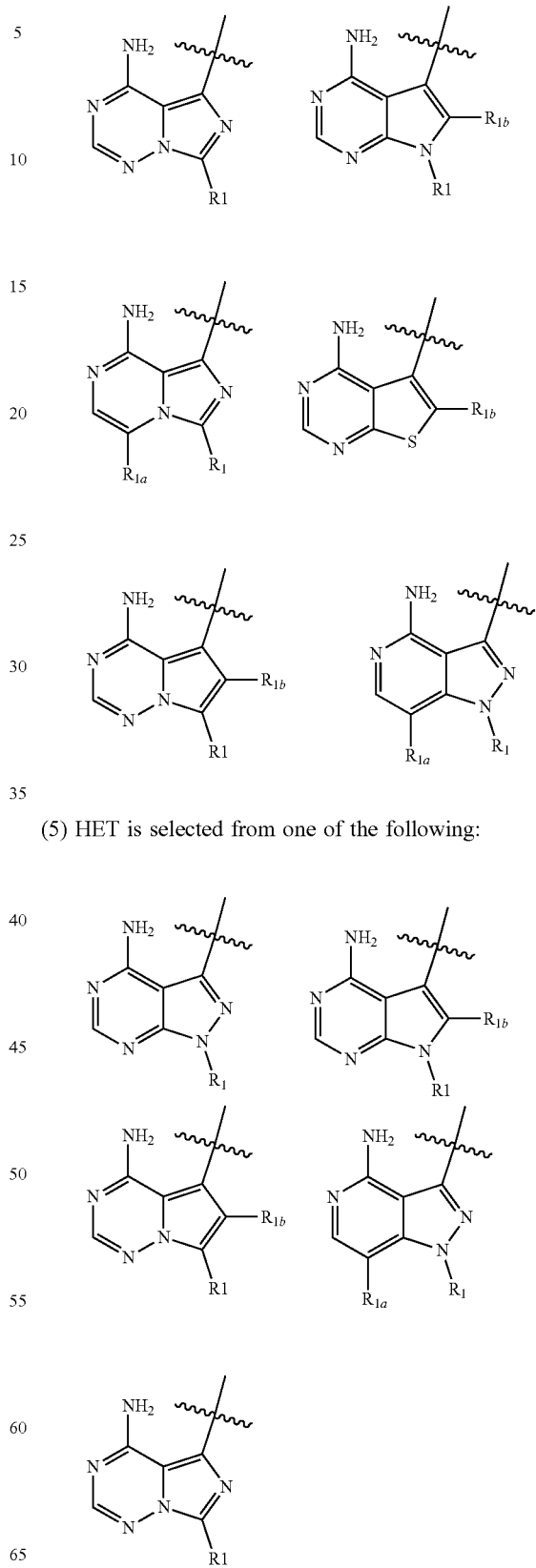

(6) HET is selected from one of the following:

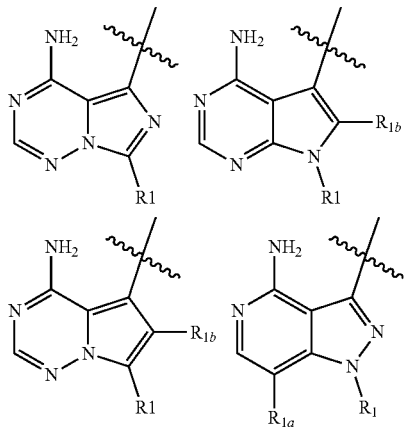

(7) HET is selected from one of the following:

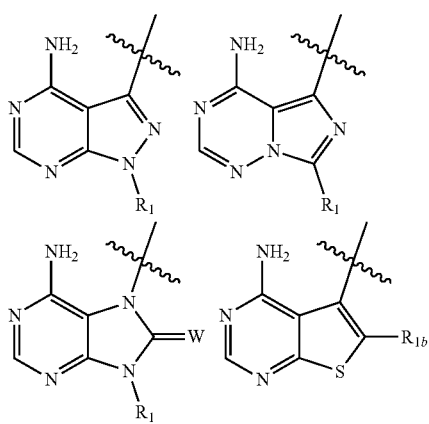

(8) HET is selected from one of the following:

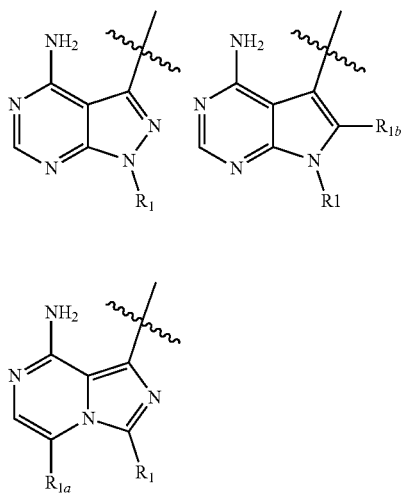

(9) HET is selected from one of the following:

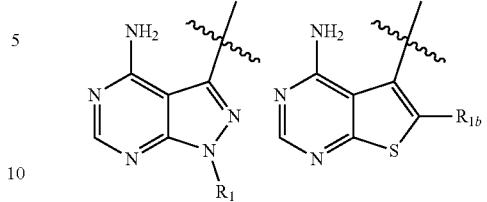

(10) HET is:

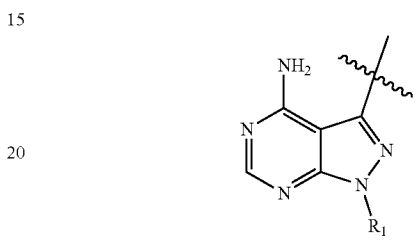

(11) R₁ is selected from hydrogen, (1-4C)haloalkyl, (1-4C)haloalkoxy or a group of the formula:

-L-Y-Q wherein:
L is absent or (1-5C)alkylene optionally substituted by one or more substituents selected from (1-2C)alkyl or oxo;
Y is absent or O, S, SO, SO₂, N(R$_a$), C(O), C(O)O, OC(O), C(O)N(R$_a$), N(R$_a$)C(O), S(O)₂N(R$_a$), or N(R$_a$)SO₂, wherein R$_a$ is selected from hydrogen or (1-4C)alkyl; and
Q is hydrogen, (1-6C)alkyl, (2-6C)alkenyl, (2-6C)alkynyl, aryl, (3-10C)cycloalkyl, (3-10C)cycloalkenyl, heteroaryl or heterocyclyl; wherein Q is optionally further substituted by one or more substituent groups independently selected from (1-4C)alkyl, halo, (1-4C)haloalkyl, (1-4C)haloalkoxy, amino, (1-4C)aminoalkyl, cyano, hydroxy, carboxy, carbamoyl, sulphamoyl, mercapto, ureido, NR$_c$R$_d$, OR$_c$, C(O)R$_c$, C(O)OR$_c$, OC(O)R$_c$, C(O)N(R$_d$)R$_c$, N(R$_d$)C(O)R$_c$, S(O)$_p$R$_c$ (where p is 0, 1 or 2), SO₂N(R$_d$)R$_c$, N(R$_d$)SO₂R$_c$, Si(R$_e$)(R$_d$)R$_c$ or (CH₂)$_q$NR$_c$R$_d$ (where q is 1, 2 or 3); wherein R$_c$, R$_d$ and R$_e$ are each independently selected from hydrogen, (1-6C)alkyl or (3-6C)cycloalkyl; or R$_c$ and R$_d$ are linked such that, together with the nitrogen atom to which they are attached, they form a 4-7 membered heterocyclic ring which is optionally substituted by one or more substituents selected from (1-4C)alkyl, halo, (1-4C)haloalkyl, (1-4C)haloalkoxy, (1-4C)alkoxy, (1-4C)alkylamino, amino, cyano or hydroxy; or
Q is optionally substituted by a group of the formula:

-L₁-L$_{Q1}$-W₁ wherein:
L₁ is absent or (1-3C)alkylene optionally substituted by one or more substituents selected from (1-2C)alkyl or oxo;
L$_{Q1}$ is absent or selected from or O, S, SO, SO₂, N(R$_f$), C(O), C(O)O, OC(O), C(O)N(R$_f$), N(R$_f$)C(O), N(R$_f$)C(O)O, OC(O)N(R$_f$), SO₂, S(O)₂N(R$_f$), or N(R$_f$)SO₂, wherein R$_f$ is selected from hydrogen or (1-2C)alkyl; and $W_1$ is hydrogen, (1-6C)alkyl, aryl, aryl(1-2C)alkyl, (3-8C)cycloalkyl, (3-8C)cycloalkenyl, heteroaryl or heterocyclyl; wherein $W_1$ is optionally substituted by one or more substituents selected from (1-4C)alkyl, halo, (1-4C)haloalkyl, (1-4C)haloalkoxy, (1-4C)alkoxy, (1-4C)alkylamino, amino, cyano, hydroxy, carboxy, carbamoyl, sulphamoyl, mercapto, ureido, aryl, heteroaryl, heterocycyl, (3-6C)cycloalkyl, $NR_hR_i$, $OR_h$, $C(O)R_h$, $C(O)OR_h$, $C(O)N(R_i)R_h$, or $(CH_2)_sNR_iR_h$ (where s is 1, 2 or 3); wherein $R_h$ and $R_i$ are each independently selected from hydrogen, (1-4C)alkyl or (3-6C)cycloalkyl;

(12) $R_1$ is selected from hydrogen, (1-4C)haloalkyl, (1-4C)haloalkoxy or a group of the formula:

-L-Y-Q wherein:
L is absent or (1-3C)alkylene optionally substituted by one or more substituents selected from (1-2C)alkyl or oxo;
Y is absent or O, $N(R_a)$, C(O), C(O)O, OC(O), C(O)N($R_a$) or $N(R_a)$C(O), wherein $R_a$ is selected from hydrogen or (1-4C)alkyl; and
Q is hydrogen, (1-6C)alkyl, (2-6C)alkenyl, (2-6C)alkynyl, aryl, (3-10C)cycloalkyl, (3-10C)cycloalkenyl, heteroaryl or heterocyclyl; wherein Q is optionally further substituted by one or more substituent groups independently selected from (1-4C)alkyl, halo, (1-4C)haloalkyl, (1-4C)haloalkoxy, amino, (1-4C)aminoalkyl, cyano, hydroxy, carboxy, carbamoyl, sulphamoyl, mercapto, ureido, $NR_cR_d$, $OR_c$, $C(O)R_c$, $C(O)OR_c$, $OC(O)R_c$, $C(O)N(R_d)R_c$, $N(R_d)C(O)R_c$, $S(O)_pR_c$ (where p is 0, 1 or 2), $SO_2N(R_d)R_c$, $N(R_d)SO_2R_G$, $Si(R_e)(R_d)R_c$ or $(CH_2)_qNR_cR_d$ (where q is 1, 2 or 3); wherein $R_c$, $R_d$ and $R_e$ are each independently selected from hydrogen, (1-6C)alkyl or (3-6C)cycloalkyl; or $R_c$ and $R_d$ are linked such that, together with the nitrogen atom to which they are attached, they form a 4-7 membered heterocyclic ring which is optionally substituted by one or more substituents selected from (1-4C)alkyl, halo, (1-4C)haloalkyl, (1-4C)haloalkoxy, (1-4C)alkoxy, (1-4C)alkylamino, amino, cyano or hydroxy; or
Q is optionally substituted by a group of the formula:

-$L_1$-$L_{Q1}$-$W_1$ wherein:
$L_1$ is absent or (1-3C)alkylene optionally substituted by one or more substituents selected from (1-2C)alkyl or oxo;
$L_{Q1}$ is absent or selected from or O, $N(R_f)$, C(O), C(O)O, OC(O), C(O)N($R_f$), $N(R_f)$C(O), $N(R_f)$C(O)O, $SO_2$, $S(O)_2N(R_f)$, or $N(R_f)SO_2$, wherein $R_f$ is selected from hydrogen or (1-2C)alkyl; and
$W_1$ is hydrogen, (1-6C)alkyl, aryl, aryl(1-2C)alkyl, (3-8C)cycloalkyl, (3-8C)cycloalkenyl, heteroaryl or heterocyclyl; wherein $W_1$ is optionally substituted by one or more substituents selected from (1-4C)alkyl, halo, (1-4C)haloalkyl, (1-4C)haloalkoxy, (1-4C)alkoxy, (1-4C)alkylamino, amino, cyano, hydroxy, carboxy, carbamoyl, sulphamoyl, mercapto, aryl, heteroaryl, heterocycyl, (3-6C)cycloalkyl, $NR_hR_i$, $OR_h$, $C(O)R_h$, $C(O)OR_h$, $C(O)N(R_i)R_h$, or $(CH_2)_sNR_iR_h$ (where s is 1,
2 or 3); wherein $R_h$ and $R_i$ are each independently selected from hydrogen, (1-4C)alkyl or (3-6C)cycloalkyl;

(13) $R_1$ is selected from hydrogen, (1-4C)haloalkyl, (1-4C)haloalkoxy or a group of the formula:

-L-Y-Q wherein:
L is absent or (1-3C)alkylene;
Y is absent or O, $N(R_a)$, C(O), C(O)O or C(O)N($R_a$), wherein $R_a$ is selected from hydrogen or (1-4C)alkyl; and
Q is hydrogen, (1-6C)alkyl, (2-6C)alkenyl, (2-6C)alkynyl, aryl, (3-10C)cycloalkyl, (3-10C)cycloalkenyl, heteroaryl or heterocyclyl; wherein Q is optionally further substituted by one or more substituent groups independently selected from (1-4C)alkyl, halo, (1-4C)haloalkyl, (1-4C)haloalkoxy, amino, (1-4C)aminoalkyl, cyano, hydroxy, carboxy, carbamoyl, sulphamoyl, mercapto, ureido, $NR_cR_d$, $OR_c$, $C(O)R_c$, $C(O)OR_c$, $OC(O)R_c$, $C(O)N(R_d)R_c$, $N(R_d)C(O)R_c$, $S(O)_pR_c$ (where p is 0, 1 or 2), $SO_2N(R_d)R_c$, $N(R_d)SO_2R_c$, $Si(R_e)(R_d)R_c$ or $(CH_2)_qNR_cR_d$ (where q is 1, 2 or 3); wherein $R_c$, $R_d$ and $R_e$ are each independently selected from hydrogen, (1-6C)alkyl or (3-6C)cycloalkyl; or $R_c$ and $R_d$ are linked such that, together with the nitrogen atom to which they are attached, they form a 4-7 membered heterocyclic ring which is optionally substituted by one or more substituents selected from (1-4C)alkyl, halo, (1-4C)haloalkyl, (1-4C)haloalkoxy, (1-4C)alkoxy, (1-4C)alkylamino, amino, cyano or hydroxy; or
Q is optionally substituted by a group of the formula:

-$L_1$-$L_{Q1}$-$W_1$ wherein:
$L_1$ is absent or (1-3C)alkylene optionally substituted by one or more substituents selected from (1-2C)alkyl or oxo;
$L_{Q1}$ is absent or selected from or O, $N(R_f)$, C(O), C(O)O, C(O)N($R_f$), $N(R_f)$C(O), $N(R_f)$C(O)O or $SO_2$, wherein $R_f$ is selected from hydrogen or (1-2C)alkyl; and
$W_1$ is hydrogen, (1-6C)alkyl, aryl, aryl(1-2C)alkyl, (3-8C)cycloalkyl, (3-8C)cycloalkenyl, heteroaryl or heterocyclyl; wherein $W_1$ is optionally substituted by one or more substituents selected from (1-4C)alkyl, halo, (1-4C)haloalkyl, (1-4C)haloalkoxy, (1-4C)alkoxy, (1-4C)alkylamino, amino, cyano, hydroxy, aryl, heteroaryl, heterocycyl, (3-6C)cycloalkyl, $NR_hR_i$, $OR_h$, $C(O)R_h$, $C(O)OR_h$, $C(O)N(R_i)R_h$, or $(CH_2)_sNR_iR_h$ (where s is 1, 2 or 3); wherein $R_h$ and $R_i$ are each independently selected from hydrogen, (1-4C)alkyl or (3-4C)cycloalkyl;

(14) $R_1$ is selected from hydrogen, (1-4C)haloalkyl, (1-4C)haloalkoxy or a group of the formula:

-L-Y-Q wherein:
L is absent or (1-3C)alkylene;
Y is absent or O, $N(R_a)$, C(O), C(O)O or C(O)N($R_a$), wherein $R_a$ is selected from hydrogen or (1-4C)alkyl; and
Q is hydrogen, (1-6C)alkyl, (2-6C)alkenyl, (2-6C)alkynyl, aryl, (3-10C)cycloalkyl, (3-10C)cycloalkenyl, heteroaryl or heterocyclyl; wherein Q is optionally further substituted by one or more substituent groups independently selected from (1-4C)alkyl, halo, (1-4C)haloalkyl, (1-4C)haloalkoxy, amino, (1-4C)aminoalkyl, cyano, hydroxy, $NR_cR_d$, $OR_c$, $C(O)R_c$, $C(O)OR_c$, $OC(O)R_c$, $C(O)N(R_d)R_c$, $N(R_d)C(O)R_c$, $S(O)_pR_c$ (where p is 0, 1 or 2), $N(R_d)SO_2R_c$, $Si(R_e)(R_d)R_c$ or $(CH_2)_qNR_cR_d$ (where q is 1 or 2); wherein $R_c$, $R_d$ and $R_e$ are each independently selected from hydrogen, (1-6C)alkyl or (3-6C)cycloalkyl; or $R_c$ and $R_d$ are linked such that, together with the nitrogen atom to which they are attached, they form a 4-6 membered heterocyclic ring which is optionally substituted by one or more substituents selected from (1-4C)alkyl, halo, (1-4C)alkoxy, amino, cyano or hydroxy; or Q is optionally substituted by a group of the formula:

-L₁-L_{Q1}-W₁ wherein:
L₁ is absent or (1-3C)alkylene;
$L_{Q1}$ is absent or selected from or $N(R_f)$, $N(R_f)C(O)$, $N(R_f)C(O)O$ or $SO_2$, wherein $R_f$ is selected from hydrogen or (1-2C)alkyl; and
W₁ is hydrogen, (1-6C)alkyl, aryl, aryl(1-2C)alkyl, (3-8C)cycloalkyl, (3-8C)cycloalkenyl, heteroaryl or heterocyclyl; wherein W₁ is optionally substituted by one or more substituents selected from (1-4C)alkyl, halo, (1-4C)haloalkyl, (1-4C)haloalkoxy, (1-4C)alkoxy, (1-4C)alkylamino, amino, cyano, hydroxy, aryl, heteroaryl, heterocycyl, (3-6C)cycloalkyl, $NR_hR_i$, $OR_h$, $C(O)R_h$, $C(O)OR_h$, $C(O)N(R_i)R_h$, or $(CH_2)_sNR_iR_h$ (where s is 1, 2 or 3); wherein $R_h$ and $R_i$ are each independently selected from hydrogen, (1-4C)alkyl or cyclopropyl;

(15) $R_1$ is selected from hydrogen, (1-4C)haloalkyl, (1-4C)haloalkoxy or a group of the formula:

-L-Y-Q wherein:
L is absent or (1-3C)alkylene optionally substituted by one or more substituents selected from (1-2C)alkyl or oxo;
Y is absent or O, $N(R_a)$, C(O), C(O)O, OC(O), C(O)N(R_a), $N(R_a)C(O)$, $S(O)_2N(R_a)$, or $N(R_a)SO_2$, wherein $R_a$ is selected from hydrogen or (1-4C)alkyl; and
Q is hydrogen, (1-6C)alkyl, (2-6C)alkenyl, (2-6C)alkynyl, aryl, (3-10C)cycloalkyl, (3-10C)cycloalkenyl, heteroaryl or heterocyclyl; wherein Q is optionally further substituted by one or more substituent groups independently selected from (1-4C)alkyl, halo, (1-4C)haloalkyl, (1-4C)haloalkoxy, amino, (1-4C)aminoalkyl, cyano, hydroxy, $NR_cR_d$, $OR_c$, $C(O)R_c$, $C(O)OR_c$, $OC(O)R_c$, $C(O)N(R_d)R_c$, $N(R_d)C(O)R_c$, $S(O)_pR_c$ (where p is 0, 1 or 2), $N(R_d)SO_2R_c$, $Si(R_e)(R_d)R_c$ or $(CH_2)_qNR_cR_d$ (where q is 1 or 2); wherein $R_c$, $R_d$ and $R_e$ are each independently selected from hydrogen, (1-6C)alkyl or (3-6C)cycloalkyl; or $R_c$ and $R_d$ are linked such that, together with the nitrogen atom to which they are attached, they form a 4-6 membered heterocyclic ring which is optionally substituted by one or more substituents selected from (1-4C)alkyl, halo, (1-4C)alkoxy, amino, cyano or hydroxy;

(16) $R_1$ is selected from hydrogen, (1-4C)haloalkyl, (1-4C)haloalkoxy or a group of the formula:

-L-Y-Q wherein:
L is absent or (1-3C)alkylene optionally substituted by one or more substituents selected from (1-2C)alkyl or oxo;
Y is absent or C(O), C(O)O, OC(O), $C(O)N(R_a)$ or $N(R_a)C(O)$, wherein $R_a$ and $R_b$ are each independently selected from hydrogen or (1-4C)alkyl; and
Q is hydrogen, (3-6C)alkyl, (2-6C)alkenyl, (2-6C)alkynyl, aryl, (3-10C)cycloalkyl, (3-10C)cycloalkenyl, heteroaryl or heterocyclyl; wherein Q is optionally further substituted by one or more substituent groups independently selected from (1-4C)alkyl, halo, (1-4C)haloalkyl, (1-4C)haloalkoxy, amino, (1-4C)aminoalkyl, cyano, hydroxy, $NR_cR_d$, $OR_c$, $C(O)R_c$, $C(O)OR_c$, $OC(O)R_c$, $C(O)N(R_d)R_c$, $N(R_d)C(O)R_c$, $S(O)_pR_c$ (where p is 0, 1 or 2), $N(R_d)SO_2R_c$, $Si(R_e)(R_d)R_c$ or $(CH_2)_qNR_cR_d$ (where q is 1 or 2); wherein $R_c$, $R_d$ and $R_e$ are each independently selected from hydrogen or (1-6C)alkyl;

(17) $R_1$ is selected from hydrogen, (1-4C)haloalkyl, (1-4C)haloalkoxy or Q
wherein:
Q is selected from hydrogen, (1-6C)alkyl, (2-6C)alkenyl, (2-6C)alkynyl, aryl, (3-10C)cycloalkyl, (3-10C)cycloalkenyl, heteroaryl or heterocyclyl; wherein Q is optionally further substituted by one or more substituent groups independently selected from (1-4C)alkyl, halo, (1-4C)haloalkyl, (1-4C)haloalkoxy, amino, (1-4C)aminoalkyl, cyano, hydroxy, carboxy, carbamoyl, sulphamoyl, mercapto, ureido, $NR_cR_d$, $OR_c$, $C(O)R_c$, $C(O)OR_c$, $OC(O)R_c$, $C(O)N(R_d)R_c$, $N(R_d)C(O)R_c$, $S(O)_pR_c$ (where p is 0, 1 or 2), $SO_2N(R_d)R_c$, $N(R_d)SO_2R_c$, $Si(R_e)(R_d)R_c$ or $(CH_2)_qNR_cR_d$ (where q is 1, 2 or 3); wherein $R_c$, $R_d$ and $R_e$ are each independently selected from hydrogen, (1-6C)alkyl or (3-6C)cycloalkyl; or $R_c$ and $R_d$ are linked such that, together with the nitrogen atom to which they are attached, they form a 4-7 membered heterocyclic ring which is optionally substituted by one or more substituents selected from (1-4C)alkyl, halo, (1-4C)haloalkyl, (1-4C)haloalkoxy, (1-4C)alkoxy, (1-4C)alkylamino, amino, cyano or hydroxy; or Q is optionally substituted by a group of the formula:

-L₁-L_{Q1}-W₁ wherein:
L₁ is absent or (1-3C)alkylene;
$L_{Q1}$ is absent or selected from or O, $N(R_f)$, C(O), C(O)O, $C(O)N(R_f)$, $N(R_f)C(O)$, $N(R_f)C(O)O$ or $SO_2$, wherein $R_f$ is selected from hydrogen or (1-2C)alkyl; and
W₁ is hydrogen, (1-6C)alkyl, aryl, aryl(1-2C)alkyl, (3-8C)cycloalkyl, (3-8C)cycloalkenyl, heteroaryl or heterocyclyl; wherein W₁ is optionally substituted by one or more substituents selected from (1-4C)alkyl, halo, (1-4C)haloalkyl, (1-4C)haloalkoxy, (1-4C)alkoxy, (1-4C)alkylamino, amino, cyano, hydroxy, aryl, heteroaryl, heterocycyl, (3-6C)cycloalkyl, $NR_hR_i$, $OR_h$, $C(O)R_h$, $C(O)OR_h$, $C(O)N(R_i)R_h$, or $(CH_2)_sNR_iR_h$ (where s is 1, 2 or 3); wherein $R_h$ and $R_i$ are each independently selected from hydrogen, (1-4C)alkyl or (3-4C)cycloalkyl;

(18) $R_1$ is selected from hydrogen, (1-4C)haloalkyl, (1-4C)haloalkoxy or Q
wherein:
Q is selected from hydrogen, (1-6C)alkyl, (2-6C)alkenyl, (2-6C)alkynyl, aryl, (3-10C)cycloalkyl, (3-10C)cycloalkenyl, 5- or 6-membered heteroaryl or heterocyclyl; wherein Q is optionally further substituted by one or more substituent groups independently selected from (1-4C)alkyl, halo, (1-4C)haloalkyl, (1-4C)haloalkoxy, amino, (1-4C)aminoalkyl, cyano, hydroxy, $NR_cR_d$, $OR_c$, $C(O)R_c$, $C(O)OR_c$, $OC(O)R_c$, $C(O)N(R_d)R_c$, $N(R_d)C(O)R_c$, $S(O)_pR_c$ (where p is 0, 1 or 2), $SO_2N(R_d)R_c$, $N(R_d)SO_2R_c$, $Si(R_e)(R_d)R_c$ or $(CH_2)_qNR_cR_d$ (where q is 1, 2 or 3); wherein $R_c$, $R_d$ and $R_e$ are each independently selected from hydrogen, (1-6C)alkyl or (3-6C)cycloalkyl; or $R_c$ and $R_d$ are linked such that, together with the nitrogen atom to which they are attached, they form a 4-7 membered heterocyclic ring which is optionally substituted by one or more substituents selected from (1-4C)alkyl, halo, (1-4C)alkoxy, amino, cyano or hydroxy; or
Q is optionally substituted by a group of the formula:

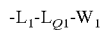

wherein:
$L_1$ is absent or (1-3C)alkylene;
$L_{Q1}$ is absent or selected from or $N(R_f)$, $N(R_f)C(O)$, $N(R_f)C(O)O$ or $SO_2$, wherein $R_f$ is selected from hydrogen or (1-2C)alkyl; and
$W_1$ is hydrogen, (1-6C)alkyl, phenyl, (3-6C)cycloalkyl, (3-6C)cycloalkenyl, 5- or 6-membered heteroaryl or heterocyclyl; wherein $W_1$ is optionally substituted by one or more substituents selected from (1-4C)alkyl, halo, (1-4C)haloalkyl, (1-4C)haloalkoxy, (1-4C)alkoxy, cyano, hydroxy, aryl, (3-6C)cycloalkyl, $NR_hR_i$, $C(O)R_h$, $C(O)OR_h$, $C(O)N(R_i)R_h$, or $(CH_2)_sNR_iR_h$ (where s is 1 or 2); wherein $R_h$ and $R_i$ are each independently selected from hydrogen, (1-2C)alkyl or cyclopropyl;

(19) $R_1$ is selected from hydrogen, (1-4C)haloalkyl, (1-4C)haloalkoxy or Q
wherein:
Q is selected from hydrogen, (1-6C)alkyl, (2-6C)alkenyl, (2-6C)alkynyl, aryl, (3-10C)cycloalkyl, (3-10C)cycloalkenyl, 5- or 6-membered heteroaryl or heterocyclyl; wherein Q is optionally further substituted by one or more substituent groups independently selected from (1-4C)alkyl, halo, (1-4C)haloalkyl, (1-4C)haloalkoxy, amino, (1-4C)aminoalkyl, cyano, hydroxy, $NR_cR_d$, $OR_c$, $C(O)R_c$, $C(O)OR_c$, $OC(O)R_c$, $C(O)N(R_d)R_c$, $N(R_d)C(O)R_c$, $S(O)_pR_c$ (where p is 0, 1 or 2), $SO_2N(R_d)R_c$, $N(R_d)SO_2R_c$, $Si(R_e)(R_d)R_c$ or $(CH_2)_qNR_cR_d$ (where q is 1, 2 or 3); wherein $R_c$, $R_d$ and $R_e$ are each independently selected from hydrogen, (1-6C)alkyl or (3-6C)cycloalkyl; or $R_c$ and $R_d$ are linked such that, together with the nitrogen atom to which they are attached, they form a 4-7 membered heterocyclic ring which is optionally substituted by one or more substituents selected from (1-4C)alkyl, halo, (1-4C)alkoxy, amino, cyano or hydroxy;

(20) $R_1$ is selected from hydrogen, (1-4C)haloalkyl, (1-4C)haloalkoxy or Q
wherein:
Q is selected from hydrogen, (1-6C)alkyl, aryl, (3-10C)cycloalkyl, (3-10C)cycloalkenyl, 5- or 6-membered heteroaryl or heterocyclyl; wherein Q is optionally further substituted by one or more substituent groups independently selected from (1-4C)alkyl, halo, (1-4C)haloalkyl, (1-4C)haloalkoxy, amino, (1-4C)aminoalkyl, cyano, hydroxy, $NR_cR_d$, $OR_c$, $C(O)R_c$, $C(O)OR_c$, $C(O)N(R_d)R_c$, $S(O)_pR_c$ (where p is 0, 1 or 2), or $(CH_2)_qNR_cR_d$ (where q is 1, 2 or 3); wherein $R_c$ and $R_d$ are each independently selected from hydrogen, (1-6C)alkyl or (3-6C)cycloalkyl;

(21) $R_1$ is selected from hydrogen, (1-4C)haloalkyl, (1-4C)haloalkoxy or Q
wherein:
Q is selected from hydrogen, (1-6C)alkyl, or heterocyclyl; wherein Q is optionally further substituted by one or more substituent groups independently selected from (1-4C)alkyl, halo, (1-4C)haloalkyl, amino, cyano, hydroxy, $NR_cR_d$, $OR_c$, $S(O)_pR_c$ (where p is 0, 1 or 2), or $(CH_2)_qNR_cR_d$ (where q is 1, 2 or 3); wherein $R_c$ and $R_d$ are each independently selected from hydrogen or (1-6C)alkyl;

(22) $R_1$ is selected from hydrogen, (4-6C)alkyl, 4-7 membered heterocyclyl or (3-10C)cycloalkyl; wherein each of said substituents is optionally further substituted by one or more substituent groups independently selected from (1-4C)alkyl, halo, amino, (1-4C)aminoalkyl, cyano, hydroxy, carboxy, $NR_cR_d$, $OR_c$, $S(O)_2R_c$ or $Si(R_d)(R_c)R_e$; wherein $R_c$, $R_d$ and $R_e$ are each independently selected from hydrogen or (1-4C)alkyl;

(23) $R_1$ is selected from hydrogen, (4-6C)alkyl or 4-7 membered heterocyclyl; wherein each of said substituents is optionally further substituted by one or more substituent groups independently selected from (1-4C)alkyl, halo, amino, (1-4C)aminoalkyl, cyano, hydroxy, carboxy, $NR_cR_d$, $OR_c$ or $S(O)_2R_c$; wherein $R_c$ and $R_d$ are each independently selected from hydrogen or (1-4C)alkyl;

(24) $R_1$ is selected from hydrogen, (1-6C)alkyl, or heterocyclyl; wherein said (1-6C)alkyl or heterocyclyl is optionally further substituted by one or more substituent groups independently selected from (1-4C)alkyl, halo, $NR_cR_d$, $OR_c$ or $S(O)_pR_c$ (where p is 0, 1 or 2), and wherein $R_c$ and $R_d$ are each independently selected from hydrogen or (1-2C)alkyl;

(25) $R_1$ is a (1-6C)alkyl or (3-6C)cycloalkyl;
(26) $R_1$ is a (4-6C)alkyl;
(27) $R_1$ is tert-butyl;
(28) $R_{1a}$ and $R_{1b}$ are each selected from H, (1-4C)alkyl, halo, (1-4C)haloalkyl, (1-4C)haloalkoxy, (1-4C)alkoxy, (1-4C)alkylamino, amino, cyano or hydroxy;
(29) $R_{1a}$ and $R_{1b}$ are each selected from H, (1-4C)alkyl, halo, (1-4C)haloalkyl, (1-4C)alkoxy, amino, cyano or hydroxy;
(30) $R_{1a}$ and $R_{1b}$ are each selected from H or (1-4C)alkyl;
(31) $R_{1a}$ and $R_{1b}$ are each H;
(32) W is selected from O or S;
(33) W is O;
(34) integer a is 0 or 1;
(35) integer a is 1;
(36) integer a is 0;
(37) $X_1$ is CH or N;
(38) $X_1$ is CH or $CR_2$;
(39) $X_1$ is CH;
(40) $X_1$ is N;
(41) $X_2$, $X_3$ and $X_4$ are independently selected from N or CH;

(42) $X_2$, $X_3$ and $X_4$ are independently selected from CH or $CR_2$;

(43) $X_2$, $X_3$ and $X_4$ are CH;

(44) $R_2$ is selected from hydrogen, halo, (1-4C)alkyl, (1-4C)alkoxy, (1-4C)haloalkyl, (1-4C)haloalkoxy, amino, cyano, nitro, phenyl, pyrindinyl, 5- or 6-membered heteroaryl, (2-4C)alkynyl, $NR_jR_k$, $OR_j$, $C(O)R_j$, $C(O)OR_j$, $OC(O)R_j$, $C(O)N(R_k)R_j$, $N(R_k)C(O)R_j$, $N(R_k)C(O)N(R_j)$, $S(O)_{r1}R_k$ (where $r_1$ is 0, 1 or 2), $SO_2N(R_j)R_k$, $N(R_j)SO_2R_k$ or $(CH_2)_vNR_jR_k$ (where v is 1, 2 or 3); wherein $R_j$ and $R_k$ are each independently selected from hydrogen or (1-4C)alkyl; and wherein said (1-4C)alkyl, phenyl, pyrindinyl or 5- or 6-membered heteroaryl is optionally substituted by one or more substituents selected from halo, (1-4C)alkyl, (1-4C)alkoxy, (1-4C)haloalkyl, (1-4C)haloalkoxy, cyano, nitro, phenyl, $NR_{j1}R_{k1}$, $C(O)R_{j1}$, $C(O)OR_{j1}$, $C(O)N(R_{k1})R_{j1}$, $SO_2N(R_{j1})R_{k1}$, $N(R_{j1})SO_2R_{k1}$ or $(CH_2)_{v1}NR_{j1}R_{k1}$ (where $v_1$ is 1, 2 or 3); and wherein $R_{j1}$ and $R_{k1}$ are each independently selected from hydrogen or (1-4C)alkyl;

(45) $R_2$ is selected from hydrogen, halo, (1-4C)alkyl, (1-4C)alkoxy, (1-4C)haloalkyl, (1-4C)haloalkoxy, cyano, 5-membered heteroaryl (e.g. triazolyl, thiazolyl, imidazolyl or thiadiazolyl), $NR_jR_k$, $C(O)R_j$, $C(O)OR_j$, $C(O)N(R_k)R_j$, or $(CH_2)_vNR_jR_k$ (where v is 1 or 2); wherein $R_j$ and $R_k$ are each independently selected from hydrogen or (1-4C)alkyl; and wherein said (1-4C)alkyl or 5-membered heteroaryl is optionally substituted by one or more substituents selected from halo, (1-4C)alkyl, (1-4C)alkoxy, (1-4C)haloalkyl, (1-4C)haloalkoxy, cyano, nitro, amino, phenyl, $C(O)N(R_{k1})R_{j1}$, $SO_2N(R_{j1})R_{k1}$ or $N(R_{j1})SO_2R_{k1}$; and wherein $R_{j1}$ and $R_{k1}$ are each independently selected from hydrogen or (1-4C)alkyl;

(46) $R_2$ is selected from hydrogen, halo, (1-4C)alkyl, (1-4C)alkoxy, (1-4C)haloalkyl, (1-4C)haloalkoxy, amino, cyano, nitro, (2-4C)alkynyl, $NR_jR_k$, $OR_j$, $C(O)R_j$, $C(O)OR_j$, $OC(O)R_j$, $C(O)N(R_k)R_j$, $N(R_k)C(O)R_j$, or $(CH_2)_vNR_jR_k$ (where v is 1, 2 or 3); wherein said (1-4C)alkyl is optionally substituted by one or more substituents selected from amino, hydroxy, (1-2C)alkoxy or halo; and wherein $R_j$ and $R_k$ are each independently selected from hydrogen or (1-4C)alkyl;

(47) $R_2$ is selected from hydrogen, halo, (1-4C)alkyl, (1-4C)alkoxy, (1-4C)haloalkyl, (1-4C)haloalkoxy, cyano, $NR_jR_k$, $OR_j$, $C(O)R_j$, $C(O)OR_j$, $C(O)N(R_k)R_j$, or $(CH_2)_vNR_jR_k$ (where v is 1 or 2); wherein said (1-4C)alkyl is optionally substituted by one or more substituents selected from amino, hydroxy, (1-2C)alkoxy or halo; and wherein $R_j$ and $R_k$ are each independently selected from hydrogen or (1-4C)alkyl;

(48) $R_2$ is selected from hydrogen, halo, (1-4C)alkyl, (1-4C)alkoxy, (1-4C)haloalkyl, cyano, $NR_jR_k$ or $OR_j$, wherein said (1-4C)alkyl is optionally substituted by one or more substituents selected from amino, hydroxy, (1-2C)alkoxy or halo; and wherein $R_j$ and $R_k$ are each independently selected from hydrogen or (1-2C)alkyl;

(49) $R_2$ is selected from hydrogen, halo, (1-4C)alkyl, (1-4C)alkoxy, $NR_jR_k$ or $OR_j$, wherein said (1-4C)alkyl is optionally substituted by one or two substituents selected from amino, hydroxy or (1-2C)alkoxy; and wherein $R_j$ and $R_k$ are each independently selected from hydrogen or (1-2C)alkyl;

(50) $R_2$ is selected from hydrogen, halo, (1-4C)alkyl or $OR_j$, wherein said (1-4C)alkyl is optionally substituted by one or two substituents selected from amino, hydroxy or (1-2C)alkoxy, and wherein R; is selected from hydrogen or (1-2C)alkyl;

(51) $R_2$ is selected from hydrogen, halo, (1-4C)alkyl or $OR_j$, wherein said (1-4C)alkyl is optionally substituted by one or two substituents selected from amino, hydroxy or (1-2C)alkoxy, and wherein $R_j$ is a (1-2C)alkyl;

(52) $R_2$ is selected from hydrogen, halo, (1-4C)alkyl or OH;

(53) $R_2$ is selected from hydrogen, halo or (1-4C)alkyl;

(54) $R_3$ is selected from hydrogen, halo, (1-4C)alkyl, (1-4C)alkoxy, (1-4C)haloalkyl, (1-4C)haloalkoxy, amino, cyano, (2-4C)alkynyl, $NR_lR_m$, $OR_l$, $C(O)R_l$, or $(CH_2)_yNR_lR_m$ (where y is 1, 2 or 3); wherein said (1-4C)alkyl is optionally substituted by one or more substituents selected from amino, hydroxy, (1-2C)alkoxy or halo; and wherein $R_l$ and $R_m$ are each independently selected from hydrogen or (1-4C)alkyl;

(55) $R_3$ is selected from halo, (1-4C)alkyl, (1-4C)alkoxy, (1-4C)haloalkyl, (1-4C)haloalkoxy, amino, cyano, (2-4C)alkynyl, $NR_lR_m$, $OR_l$, $C(O)R_l$, or $(CH_2)_yNR_lR_m$ (where y is 1, 2 or 3); wherein said (1-4C)alkyl is optionally substituted by one or more substituents selected from amino, hydroxy, (1-2C)alkoxy or halo; and wherein $R_l$ and $R_m$ are each independently selected from hydrogen or (1-4C)alkyl

(56) $R_3$ is selected from hydrogen, halo, (1-4C)alkyl, (1-4C)alkoxy, (1-4C)haloalkyl, cyano, $NR_lR_m$, $OR_l$, $C(O)R_l$, or $(CH_2)_yNR_lR_m$ (where y is 1, 2 or 3); wherein said (1-4C)alkyl is optionally substituted by one or more substituents selected from amino, hydroxy, (1-2C)alkoxy or halo; and wherein $R_l$ and $R_m$ are each independently selected from hydrogen or (1-4C)alkyl;

(57) $R_3$ is selected from hydrogen, halo, (1-4C)alkyl, (1-4C)alkoxy, $NR_lR_m$, $OR_l$, $C(O)R_l$, or $(CH_2)_yNR_lR_m$ (where y is 1, 2 or 3); wherein said (1-4C)alkyl is optionally substituted by one or two substituents selected from amino, hydroxy or (1-2C)alkoxy; and wherein $R_l$ and $R_m$ are each independently selected from hydrogen or (1-2C)alkyl;

(58) $R_3$ is selected from halo, (1-4C)alkyl, (1-4C)alkoxy, $NR_lR_m$, $OR_l$, $C(O)R_l$, or $(CH_2)_yNR_lR_m$ (where y is 1, 2 or 3); wherein said (1-4C)alkyl is optionally substituted by one or two substituents selected from amino, hydroxy or (1-2C)alkoxy; and wherein $R_l$ and $R_m$ are each independently selected from hydrogen or (1-2C)alkyl

(59) $R_3$ is selected from hydrogen, halo, (1-4C)alkyl, (1-4C)alkoxy, $NR_lR_m$ or $OR_l$, wherein $R_l$ and $R_m$ are each independently selected from hydrogen or (1-2C)alkyl;

(60) $R_3$ is selected from halo, (1-4C)alkyl, (1-4C)alkoxy, $NR_lR_m$ or $OR_l$, wherein $R_l$ and $R_m$ are each independently selected from hydrogen or (1-2C)alkyl;

(61) $R_3$ is selected from hydrogen or halo;

(62) $R_3$ is a halogen (e.g. chloro, bromo or fluoro, particularly chloro);

(63) $R_1$ is selected from (1-6C)alkyl, (3-6C)cyclcoalkyl, or heterocyclyl; wherein said (1-6C)alkyl, (3-6C)cyclcoalkyl or heterocyclyl is optionally further substituted by one or more substituent groups independently selected from (1-4C)alkyl, halo, $NR_cR_d$, $OR_c$ or $S(O)_pR_c$ (where p is 0, 1 or 2), and wherein $R_c$ and $R_d$ are each independently selected from hydrogen or (1-2C)alkyl;

(64) $R_1$ is selected from (4-6C)alkyl, (3-6C)cycloalkyl or 5-6 membered heterocyclyl; wherein said (1-6C)alkyl, (3-6C)cyclcoalkyl or 5-6 membered heterocyclyl is optionally further substituted by one or more substituent groups independently selected from (1-4C)alkyl, halo, $NR_cR_d$, $OR_c$ or $S(O)_pR_c$ (where p is 0, 1 or 2), and wherein $R_c$ and $R_d$ are each independently selected from hydrogen or (1-2C)alkyl;

(65) $R_1$ is selected from tert-butyl or piperidinyl; wherein said piperidinyl is optionally further substituted by one or more substituent groups independently selected from (1-4C)alkyl, halo, $NR_cR_d$, $OR_c$ or $S(O)_pR_c$ (where p is 0, 1 or 2), and wherein $R_c$ and $R_d$ are each independently selected from hydrogen or (1-2C)alkyl.

In the genus of compounds covered by Formula I, it will be appreciated that when integer a is 1 or 2, the substituent $R_3$ may be located at either or both the 3-position of the (aza)indole and/or on the nitrogen atom of the (aza)indole (i.e. the 1-position). Suitably, integer a is selected from 0 or 1 and thus the substitutent $R_3$ is either absent or present at the 3-position of the (aza)indole only.

In certain embodiments, the compound of the present invention is not one of the following:

2-(4-amino-1-isopropyl-pyrazolo[3,4-d]pyrimidin-3-yl)-1H-indol-5-ol; or (1r,4r)-4-(4-amino-5-(7-methoxy-1H-indol-2-yl)imidazo[1,5-f][1,2,4]triazin-7-yl)cyclohexanecarboxylic acid.

Suitably, a heteroaryl is a 5- or 6-membered heteroaryl ring comprising one, two or three heteroatoms selected from N, O or S.

Suitably, a heterocyclyl group is a 4-, 5- or 6-membered heterocyclyl ring comprising one, two or three heteroatoms selected from N, O or S. Most suitably, a heterocyclyl group is a 5-, 6- or 7-membered ring comprising one, two or three heteroatoms selected from N, O or S [e.g. morpholinyl (e.g. 4-morpholinyl), pyridinyl, piperazinyl, homopiperazinyl or pyrrolidinonyl].

Suitably an aryl group is phenyl.

Suitably, HET is as defined in any one of paragraphs (1) to (10). Most suitably, HET is as defined in paragraph (10).

Suitably, $R_1$ is as defined in any one of paragraphs (11) to (27) or (63) to (65). More suitably, $R_1$ is as defined in any one of paragraphs (14) to (27) or (63) to (65). Most suitably, $R_1$ is as defined in paragraph (65).

Suitably $R_{1a}$ and $R_{1b}$ are as defined in any one of paragraphs (28) to (31). Most suitably, $R_{1a}$ and $R_{1b}$ are as defined in paragraph (31).

Suitably, W is as defined in any one of paragraphs (32) to (33). Most suitably, W is as defined in paragraph (33).

Suitably, integer a is as defined in any one of paragraphs (34) to (36).

Suitably, $X_1$ is as defined in any one of paragraphs (37) to (40).

Suitably $X_2$, $X_3$ and $X_4$ are as defined in any one of paragraphs (41) to (43). Most suitably, $X_2$, $X_3$ and $X_4$ are as defined in paragraph (43).

Suitably, $R_2$ is as defined in any one of paragraphs (44) to (53). More suitably, $R_2$ is as defined in any one of paragraphs (49) to (53). Most suitably, $R_2$ is as defined in paragraph (53).

Suitably, $R_3$ is as defined in any one of paragraphs (54) to (62). Most suitably, $R_3$ is as defined in paragraph (62).

In a particular group of compounds of the invention, HET is as defined in paragraph (10) above, i.e. the compoundshave the structural formula Ia (a sub-definition of Formula (I)) shown below, or a pharmaceutically acceptable salt, hydrate and/or solvate thereof:

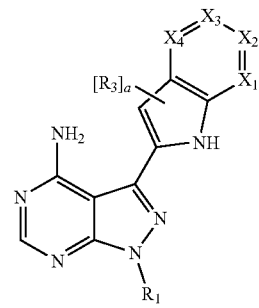

Ia wherein, $R_1$, integer a, $X_1$, $X_2$, $X_3$, $X_4$ and $R_3$ each have any one of the meanings defined herein.

In an embodiment of the compounds of Formula Ia:

$R_1$ is as defined in any one of paragraphs (11) to (27) or (63) to (65) above;

integer a is as defined in any one of paragraphs (34) to (36) above;

$X_1$ is as defined in any one of paragraphs (37) to (40) above;

$X_2$, $X_3$ and $X_4$ are as defined in any one of paragraphs (41) to (43) above;

$R_2$ is as defined in any one of paragraphs (44) to (53) above; and $R_3$ is as defined in any one of paragraphs (54) to (62) above.

In another embodiment of the compounds of Formula Ia:

$R_1$ is as defined in paragraph (65) above;

integer a is as defined in any one of paragraphs (34) to (36) above;

$X_1$ is as defined in any one of paragraphs (37) to (40) above;

$X_2$, $X_3$ and $X_4$ are as defined in any one of paragraphs (41) to (43) above;

$R_2$ is as defined in any one of paragraphs (44) to (53) above; and $R_3$ is as defined in any one of paragraphs (54) to (62) above.

In yet another embodiment of the compounds of Formula Ia:

$R_1$ is as defined in paragraphs (27) or (65) above;

integer a is as defined in any one of paragraphs (35) to (36) above;

$X_1$ is as defined in paragraph (40) above;

$X_2$, $X_3$ and $X_4$ are as defined in paragraph (43) above;

$R_2$ is as defined in paragraph (53) above; and $R_3$ is as defined in paragraph (62) above.

In a particular embodiment, the compounds of the present invention have the structural formula Ib shown below, or a pharmaceutically acceptable salt, hydrate and/or solvate thereof:

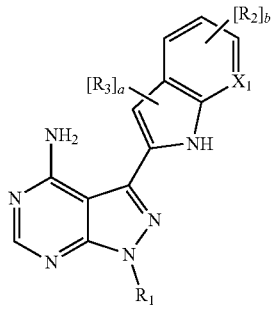

Ib wherein, $R_1$, integer a, $X_1$, $R_2$ and $R_3$ each have any one of the meanings defined herein; and b is an integer selected from 0, 1 or 2.

In an embodiment of the compounds of Formula Ib:

$R_1$ is as defined in any one of paragraphs (11) to (27) or (63) to (65) above;

integer a is as defined in any one of paragraphs (34) to (36) above;

$X_1$ is as defined in any one of paragraphs (37) to (40) above;

$R_2$ is as defined in any one of paragraphs (44) to (53) above;

$R_3$ is as defined in any one of paragraphs (54) to (62) above; and integer b is an integer selected from 0 or 1.

In another embodiment of the compounds of Formula Ib:

$R_1$ is as defined in paragraph (65) above;

integer a is as defined in any one of paragraphs (34) to (36) above;

$X_1$ is as defined in any one of paragraphs (37) to (40) above;

$R_2$ is as defined in any one of paragraphs (44) to (53) above;

$R_3$ is as defined in any one of paragraphs (54) to (62) above; and integer b is an integer selected from 0 or 1.

In yet another embodiment of the compounds of Formula Ib:

$R_1$ is as defined in paragraph (27) or (65) above;

integer a is as defined in any one of paragraphs (35) to (36) above;

$X_1$ is as defined in paragraph (40) above;

$R_2$ is as defined in paragraph (53) above;

$R_3$ is as defined in paragraphs (62) above; and integer b is an integer selected from 0 or 1.

In a further group of compounds of the invention, the compounds have the structural formula Ic (a sub-definition of formula (I)) shown below, or a pharmaceutically acceptable salt, hydrate and/or solvate thereof:

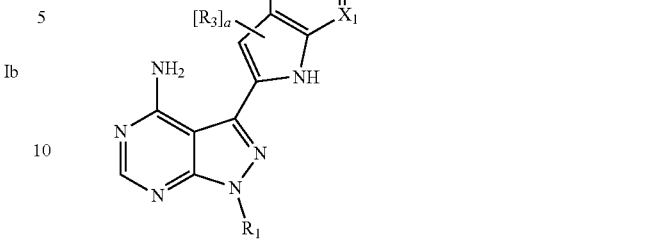

Ic wherein, $R_1$, integer a, $X_1$ and $R_3$ each have any one of the meanings defined herein.

In an embodiment of the compounds of Formula Ic:

$R_1$ is as defined in any one of paragraphs (11) to (27) or (63) to (65) above;

integer a is as defined in any one of paragraphs (34) to (37) above;

$X_1$ is as defined in any one of paragraphs (37) to (40) above; and $R_3$ is as defined in any one of paragraphs (54) to (62) above.

In another embodiment of the compounds of Formula Ic:

$R_1$ is as defined in paragraph (65) above;

integer a is as defined in any one of paragraphs (34) to (37) above;

$X_1$ is as defined in any one of paragraphs (37) to (40) above; and $R_3$ is as defined in any one of paragraphs (54) to (62) above.

In yet another embodiment of the compounds of Formula Ic:

$R_1$ is as defined in paragraph (27) or (65) above;

integer a is as defined in any one of paragraphs (35) to (36) above;

$X_1$ is as defined in paragraph (40) above; and $R_3$ is as defined in paragraph (62) above.

In a further group of compounds of the invention, the compounds have the structural formula Id (a sub-definition of formula (I)) shown below, or a pharmaceutically acceptable salt, hydrate and/or solvate thereof:

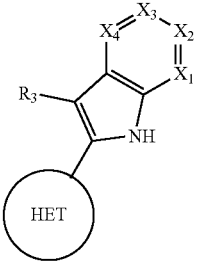

Id wherein HET, $X_1$, $X_2$, $X_3$, $X_4$ and $R_3$ each have any one of the meanings defined herein.

In an embodiment of the compounds of Formula Id:

HET is as defined in any one of paragraphs (1) to (10) above;

$X_1$ is as defined in any one of paragraphs (37) to (40) above;

$X_2$, $X_3$ and $X_4$ are as defined in any one of paragraphs (41) to (43) above; and $R_3$ is as defined in any one of paragraphs (54) to (62) above.

In another embodiment of the compounds of Formula Id:

HET is as defined in paragraph (10) above;

$X_1$ is as defined in paragraph (40) above;

$X_2$, $X_3$ and $X_4$ are as defined in paragraph (43) above; and $R_3$ is as defined in paragraph (62) above.

In a further group of compounds of the invention, the compounds have the structural formula Ie (a sub-definition of formula (I)) shown below, or a pharmaceutically acceptable salt, hydrate and/or solvate thereof:

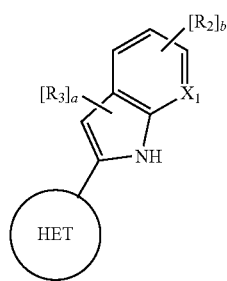

Ie wherein HET, $X_1$, $R_2$ and $R_3$ each have any one of the meanings defined herein and a and b are integers independently selected from 0 or 1.

In an embodiment of the compounds of Formula Ie:

HET is as defined in any one of paragraphs (1) to (10) above;

integer a is as defined in any one of paragraphs (34) to (36) above;

$X_1$ is as defined in any one of paragraphs (37) to (40) above;

$R_2$ is as defined in any one of paragraphs (44) to (53) above;

$R_3$ is as defined in any one of paragraphs (54) to (62) above; and b is an integer selected from 0 or 1.

In another embodiment of the compounds of Formula Ie:

HET is as defined in paragraph (10) above;

integer a is as defined in any one of paragraphs (35) to (36) above;

$X_1$ is as defined in paragraph (40) above;

$R_2$ is as defined in paragraph (53) above;

$R_3$ is as defined in paragraph (62) above; and b is an integer selected from 0 or 1.

In a further group of compounds of the invention, the compounds have the structural formula If (a sub-definition of formula (I)) shown below, or a pharmaceutically acceptable salt, hydrate and/or solvate thereof:

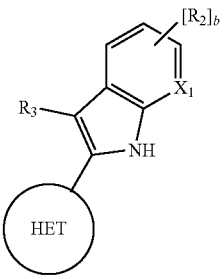

If wherein HET, $X_1$, $R_2$ and $R_3$ each have any one of the meanings defined herein, and b is an integer selected from 0 or 1.

In an embodiment of the compounds of Formula If:

HET is as defined in any one of paragraphs (1) to (10) above;

$X_1$ is as defined in any one of paragraphs (37) to (40) above;

$R_2$ is as defined in any one of paragraphs (44) to (53) above;

$R_3$ is as defined in any one of paragraphs (54) to (62) above; and b is an integer selected from 0 or 1.

In another embodiment of the compounds of Formula If:

HET is as defined in paragraph (10) above;

$X_1$ is as defined in paragraph (40) above;

$R_2$ is as defined in paragraph (53) above;

$R_3$ is as defined in paragraph (62) above; and b is an integer selected from 0 or 1.

In an alternative embodiment of the compounds of Formula If:

HET is as defined in paragraph (10) above;

$X_1$ is N;

$R_2$ is as defined in paragraph (53) above;

$R_3$ is as defined in paragraph (62) above; and b is an integer selected from 0 or 1.

In a further group of compounds of the invention, the compounds have the structural formula Ig (a sub-definition of formula (I)) shown below, or a pharmaceutically acceptable salt, hydrate and/or solvate thereof:

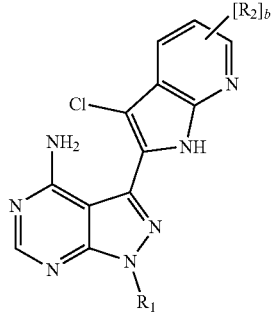

Ig wherein $R_1$ and $R_2$ each have any one of the meanings defined herein, and b is an integer selected from 0 or 1.

In an embodiment of the compounds of Formula Ig:

$R_1$ is as defined in any one of paragraphs (11) to (27) or (63) to (65) above;

R₂ is as defined in any one of paragraphs (44) to (53) above; and b is an integer selected from 0 or 1.

In another embodiment of the compounds of Formula Ig:
R₁ is as defined in paragraph (27) above;
R₂ is as defined in paragraph (53) above; and
b is an integer selected from 0 or 1.

In yet another embodiment of the compounds of Formula Ig:
R₁ is as defined in paragraph (65) above;
R₂ is as defined in paragraph (53) above; and
b is an integer selected from 0 or 1.

Particular compounds of the present invention include any of the compounds exemplified in the present application, or a pharmaceutically acceptable salt or solvate thereof, and, in particular, any of the following:

1-tert-butyl-3-(3-chloro-1H-indol-2-yl)-1H-pyrazolo[3,4-d]pyrimidin-4-amine;
1-tert-butyl-3-(1H-indol-2-yl)-1H-pyrazolo[3,4-d]pyrimidin-4-amine;
3-(1H-indol-2-yl)-1-(1-methanesulfonylpiperidin-4-yl)-1H-pyrazolo[3,4-d]pyrimidin-4-amine; or
3-(3-chloro-1H-indol-2-yl)-1-(1-methanesulfonylpiperidin-4-yl)-1H-pyrazolo[3,4-d]pyrimidin-4-amine.

Further compounds of the present invention include any of the compounds exemplified in the present application, or a pharmaceutically acceptable salt or solvate thereof, and, in particular, any of the following:

1-(tert-Butyl)-3-(1H-indol-2-yl)-1H-pyrazolo[3,4-d]pyrimidin-4-amine;
3-(1H-Indol-2-yl)-1-(1-methylsulfonyl-4-piperidyl)pyrazolo[3,4-d]pyrimidin-4-amine;
1-tert-Butyl-3-(3-chloro-1H-indol-2-yl)pyrazolo[3,4-d]pyrimidin-4-amine;
3-(3-Chloro-1H-indol-2-yl)-1-(1-methylsulfonyl-4-piperidyl)pyrazolo[3,4-d]pyrimidin-4-amine;
N-(trans-4-(4-Amino-3-(1H-indol-2-yl)-1H-pyrazolo[3,4-d]pyrimidin-1-yl)cyclohexyl)cyclopropanecarboxamide;
3-(1H-Indol-2-yl)-1-(trans-4-morpholinocyclohexyl)-1H-pyrazolo[3,4-d]pyrimidin-4-amine;
3-(3-Chloro-1H-indol-2-yl)-1-(trans-4-morpholinocyclohexyl)-1H-pyrazolo[3,4-d]pyrimidin-4-amine;
N-[4-[trans-4-Amino-3-(3-chloro-1H-indol-2-yl)pyrazolo[3,4-d]pyrimidin-1-yl]cyclohexyl]cyclopropanecarboxamide;
1-tert-Butyl-3-{1H-pyrrolo[2,3-b]pyridin-2-yl}-1H-pyrazolo[3,4-d]pyrimidin-4-amine;
1-tert-Butyl-3-{3-chloro-1H-pyrrolo[2,3-b]pyridin-2-yl}-1H-pyrazolo[3,4-d]pyrimidin-4-amine;
3-(1H-Indol-2-yl)-1-(propan-2-yl)-1H-pyrazolo[4,3-c]pyridin-4-amine;
3-(3-Chloro-1H-indol-2-yl)-1-(propan-2-yl)-1H-pyrazolo[4,3-c]pyridin-4-amine;
5-(1H-Indol-2-yl)-7-(propan-2-yl)pyrrolo[2,1-f][1,2,4]triazin-4-amine;
5-(3-Chloro-1H-indol-2-yl)-7-(propan-2-yl)pyrrolo[2,1-f][1,2,4]triazin-4-amine;
3-(6-Bromo-1H-indol-2-yl)-1-isopropyl-pyrazolo[3,4-d]pyrimidin-4-amine;
3-(6-Bromo-3-chloro-1H-indol-2-yl)-1-isopropyl-pyrazolo[3,4-d]pyrimidin-4-amine;
2-(4-Amino-1-(tert-butyl)-1H-pyrazolo[3,4-d]pyrimidin-3-yl)-1H-indole-6-carbonitrile;
2-(4-Amino-1-(tert-butyl)-1H-pyrazolo[3,4-d]pyrimidin-3-yl)-3-chloro-1H-indole-6-carbonitrile;
(2-(4-Amino-1-(tert-butyl)-1H-pyrazolo[3,4-d]pyrimidin-3-yl)-3-chloro-1H-indol-6-yl)methanol;
1-(tert-Butyl)-3-(6-chloro-1H-indol-2-yl)-1H-pyrazolo[3,4-d]pyrimidin-4-amine;
7-Isopropyl-5-(1H-pyrrolo[2,3-b]pyridin-2-yl)pyrrolo[2,3-d]pyrimidin-4-amine;
1-(1-Methanesulfonylpiperidin-4-yl)-3-{1H-pyrrolo[2,3-b]pyridin-2-yl}-1H-pyrazolo[3,4-d]pyrimidin-4-amine;
3-{3-Chloro-1H-pyrrolo[2,3-b]pyridin-2-yl}-1-(1-methanesulfonylpiperidin-4-yl)-1H-pyrazolo[3,4-d]pyrimidin-4-amine;
1-tert-Butyl-3-(3,6-dichloro-1H-indol-2-yl)-1H-pyrazolo[3,4-d]pyrimidin-4-amine;
1-tert-Butyl-3-{3-chloro-6-[(methylamino)methyl]-1H-indol-2-yl}-1H-pyrazolo[3,4-d]pyrimidin-4-amine;
1-tert-Butyl-3-[3-chloro-6-(methoxymethyl)-1H-indol-2-yl]-1H-pyrazolo[3,4-d]pyrimidin-4-amine; tert-Butyl N-[cis-4-(4-amino-3-{1H-pyrrolo[2,3-b]pyridin-2-yl}-1H-pyrazolo[3,4-d]pyrimidin-1-yl)cyclohexyl]carbamate;
tert-Butyl (trans-4-(4-amino-3-(1H-pyrrolo[2,3-b]pyridin-2-yl)-1H-pyrazolo[3,4-d]pyrimidin-1-yl)cyclohexyl)carbamate;
tert-Butyl N-[cis-4-(4-amino-3-{3-chloro-1H-pyrrolo[2,3-b]pyridin-2-yl}-1H-pyrazolo[3,4-d]pyrimidin-1-yl)cyclohexyl]carbamate;
tert-Butyl N-[trans-4-(4-amino-3-{3-chloro-1H-pyrrolo[2,3-b]pyridin-2-yl}-1H-pyrazolo[3,4-d]pyrimidin-1-yl)cyclohexyl]carbamate;
1-Methyl-3-{1H-pyrrolo[2,3-b]pyridin-2-yl}-1H-pyrazolo[3,4-d]pyrimidin-4-amine;
1-Isopropyl-3-(1H-pyrrolo[2,3-b]pyridin-2-yl)-1H-pyrazolo[4,3-c]pyridin-4-amine;
3-(3-Chloro-1H-pyrrolo[2,3-b]pyridin-2-yl)-1-isopropyl-1H-pyrazolo[4,3-c]pyridin-4-amine;
3-(3-bromo-1H-pyrrolo[2,3-b]pyridin-2-yl)-1-(tert-butyl)-1H-pyrazolo[3,4-d]pyrimidin-4-amine;
3-(6-(Aminomethyl)-3-chloro-1H-indol-2-yl)-1-(tert-butyl)-1H-pyrazolo[3,4-d]pyrimidin-4-amine;
N-(trans-4-(4-Amino-3-(1H-pyrrolo[2,3-b]pyridin-2-yl)-1H-pyrazolo[3,4-d]pyrimidin-1-yl)cyclohexyl)cyclopropanecarboxamide;
1-Isopropyl-3-(1H-pyrrolo[2,3-b]pyridin-2-yl)pyrazolo[3,4-d]pyrimidin-4-amine;
1-(cis-4-Aminocyclohexyl)-3-(3-chloro-1H-pyrrolo[2,3-b]pyridin-2-yl)-1H-pyrazolo[3,4-d]pyrimidin-4-amine dihydrochloride;
1-Cyclohexyl-3-(1H-indol-2-yl)pyrazolo[3,4-d]pyrimidin-4-amine;
3-[4-Amino-3-(1H-pyrrolo[2,3-b]pyridin-2-yl)pyrazolo[3,4-d]pyrimidin-1-yl]cyclopentanol;
1-Cyclohexyl-3-(1H-pyrrolo[2,3-b]pyridin-2-yl)pyrazolo[3,4-d]pyrimidin-4-amine;
1-Cyclobutyl-3-(1H-pyrrolo[2,3-b]pyridin-2-yl)pyrazolo[3,4-d]pyrimidin-4-amine;
1-Ethyl-3-(1H-pyrrolo[2,3-b]pyridin-2-yl)pyrazolo[3,4-d]pyrimidin-4-amine;
3-(1H-Indol-2-yl)-1-isopropyl-pyrazolo[3,4-d]pyrimidin-4-amine;
5-(3-Chloro-1H-pyrrolo[2,3-b]pyridin-2-yl)-7-isopropyl-pyrrolo[2,3-d]pyrimidin-4-amine;
3-(3-Chloro-1H-pyrrolo[2,3-b]pyridin-2-yl)-1-ethyl-pyrazolo[3,4-d]pyrimidin-4-amine;
5-(1H-Indol-2-yl)-7-isopropyl-pyrrolo[2,3-d]pyrimidin-4-amine;
5-(3-Chloro-1H-indol-2-yl)-7-isopropyl-pyrrolo[2,3-d]pyrimidin-4-amine;
3-(3-Bromo-1H-indol-2-yl)-1-(tert-butyl)-1H-pyrazolo[3,4-d]pyrimidin-4-amine;
1-(tert-Butyl)-3-(5-chloro-1H-pyrrolo[2,3-b]pyridin-2-yl)-1H-pyrazolo[3,4-d]pyrimidin-4-amine;

1-(tert-Butyl)-3-(3,5-dichloro-1H-pyrrolo[2,3-b]pyridin-2-yl)-1H-pyrazolo[3,4-d]pyrimidin-4-amine;
2-(2-(4-Amino-1-(tert-butyl)-1H-pyrazolo[3,4-d]pyrimidin-3-yl)-3-chloro-1H-indol-6-yl)propan-2-ol;
N-(2-(4-Amino-1-(tert-butyl)-1H-pyrazolo[3,4-d]pyrimidin-3-yl)-1H-indol-6-yl)methanesulfonamide;
1-(2-(4-Amino-1-(tert-butyl)-1H-pyrazolo[3,4-d]pyrimidin-3-yl)-1H-indol-6-yl)-3-methylurea;
3-(3-Chloro-1H-pyrrolo[2,3-b]pyridin-2-yl)-1-isopropyl-1H-pyrazolo[3,4-d]pyrimidin-4-amine;
3-(3-Chloro-1H-pyrrolo[2,3-b]pyridin-2-yl)-1-(tetrahydro-2H-pyran-4-yl)-1H-pyrazolo[3,4-d]pyrimidin-4-amine;
4-((4-Amino-3-(3-chloro-1H-pyrrolo[2,3-b]pyridin-2-yl)-1H-pyrazolo[3,4-d]pyrimidin-1-yl)methyl)benzonitrile;
1-(Azetidin-3-yl)-3-(3-chloro-1H-pyrrolo[2,3-b]pyridin-2-yl)-1H-pyrazolo[3,4-d]pyrimidin-4-amine;
3-(3-Chloro-1H-pyrrolo[2,3-b]pyridin-2-yl)-1-((tetrahydro-2H-pyran-4-yl)methyl)-1H-pyrazolo[3,4-d]pyrimidin-4-amine;
3-(3-Chloro-1H-pyrrolo[2,3-b]pyridin-2-yl)-1-((tetrahydro-2H-pyran-2-yl)methyl)-1H-pyrazolo[3,4-d]pyrimidin-4-amine;
3-(3-Chloro-1H-pyrrolo[2,3-b]pyridin-2-yl)-1-(2,2,2-trifluoroethyl)-1H-pyrazolo[3,4-d]pyrimidin-4-amine;
1-(sec-Butyl)-3-(3-chloro-1H-pyrrolo[2,3-b]pyridin-2-yl)-1H-pyrazolo[3,4-d]pyrimidin-4-amine;
3-(3-Chloro-1H-indol-2-yl)-1-cyclohexyl-pyrazolo[3,4-d]pyrimidin-4-amine;
3-(3-Chloro-1H-indol-2-yl)-1-isopropyl-pyrazolo[3,4-d]pyrimidin-4-amine;
3-(3-Chloro-1H-pyrrolo[2,3-b]pyridin-2-yl)-1-methyl-pyrazolo[3,4-d]pyrimidin-4-amine;
3-(3-Chloro-1H-pyrrolo[2,3-b]pyridin-2-yl)-1-cyclobutyl-pyrazolo[3,4-d]pyrimidin-4-amine;
3-(3-Chloro-1H-pyrrolo[2,3-b]pyridin-2-yl)-1-cyclohexyl-pyrazolo[3,4-d]pyrimidin-4-amine;
N-[trans-4-[4-Amino-3-(3-chloro-1H-pyrrolo[2,3-b]pyridin-2-yl)pyrazolo[3,4-d]pyrimidin-1-yl]cyclohexyl]cyclopropanecarboxamide;
3-[4-Amino-3-(3-chloro-1H-pyrrolo[2,3-b]pyridin-2-yl)pyrazolo[3,4-d]pyrimidin-1-yl]cyclopentanol;
1-tert-Butyl-3-(6-methyl-1H-indol-2-yl)pyrazolo[3,4-d]pyrimidin-4-amine;
1-tert-Butyl-3-(3-chloro-6-methyl-1H-indol-2-yl)pyrazolo[3,4-d]pyrimidin-4-amine;
1-(tert-Butyl)-3-(3-chloro-6-((dimethylamino)methyl)-1H-indol-2-yl)-1H-pyrazolo[3,4-d]pyrimidin-4-amine;
7-Chloro-1-isopropyl-3-(1H-pyrrolo[2,3-b]pyridin-2-yl)-1H-pyrazolo[4,3-c]pyridin-4-amine;
1-tert-Butyl-3-(5-fluoro-1H-indol-2-yl)pyrazolo[3,4-d]pyrimidin-4-amine;
1-tert-Butyl-3-(4-chloro-1H-indol-2-yl)pyrazolo[3,4-d]pyrimidin-4-amine;
1-(tert-Butyl)-3-(3-fluoro-1H-indol-2-yl)-1H-pyrazolo[3,4-d]pyrimidin-4-amine;
3-(3-Chloro-1H-pyrrolo[2,3-b]pyridin-2-yl)-1-(2-(4-(dimethylamino)piperidin-1-yl)ethyl)-1H-pyrazolo[3,4-d]pyrimidin-4-amine;
3-(3-Chloro-1H-pyrrolo[2,3-b]pyridin-2-yl)-1-(tetrahydrofuran-3-yl)-1H-pyrazolo[3,4-d]pyrimidin-4-amine;
3-(3-Chloro-1H-pyrrolo[2,3-b]pyridin-2-yl)-1-cyclopentyl-1H-pyrazolo[3,4-d]pyrimidin-4-amine;
3-(3-Chloro-1H-pyrrolo[2,3-b]pyridin-2-yl)-1-isopentyl-1H-pyrazolo[3,4-d]pyrimidin-4-amine;
3-(3-Chloro-1H-pyrrolo[2,3-b]pyridin-2-yl)-1-neopentyl-1H-pyrazolo[3,4-d]pyrimidin-4-amine;
3-(3-Chloro-1H-pyrrolo[2,3-b]pyridin-2-yl)-1-propyl-1H-pyrazolo[3,4-d]pyrimidin-4-amine;
1-tert-Butyl-3-(3-chloro-5-fluoro-1H-indol-2-yl)pyrazolo[3,4-d]pyrimidin-4-amine;
1-tert-Butyl-3-(5-methyl-1H-indol-2-yl)pyrazolo[3,4-d]pyrimidin-4-amine;
3-(3-Chloro-1H-indol-2-yl)-1-((tetrahydro-2H-pyran-4-yl)methyl)-1H-pyrazolo[3,4-d]pyrimidin-4-amine;
3-(3-Chloro-1H-indol-2-yl)-1-(tetrahydrofuran-3-yl)-1H-pyrazolo[3,4-d]pyrimidin-4-amine;
3-(3-Chloro-1H-pyrrolo[2,3-b]pyridin-2-yl)-1-(2-(piperidin-1-yl)ethyl)-1H-pyrazolo[3,4-d]pyrimidin-4-amine;
2-(4-Amino-1-(tert-butyl)-1H-pyrazolo[3,4-d]pyrimidin-3-yl)-1H-pyrrolo[2,3-b]pyridine-6-carbonitrile;
1-tert-Butyl-3-(3,4-dichloro-1H-indol-2-yl)pyrazolo[3,4-d]pyrimidin-4-amine; or
2-(4-Amino-1-tert-butyl-pyrazolo[3,4-d]pyrimidin-3-yl)-1H-indole-5-carbonitrile.

Further compounds of the present invention include any of the compounds exemplified in the present application, or a pharmaceutically acceptable salt or solvate thereof, and, in particular, any of the following:
1-tert-Butyl-3-(3-chloro-1H-indol-2-yl)pyrazolo[3,4-d]pyrimidin-4-amine;
3-(3-Chloro-1H-indol-2-yl)-1-(1-methylsulfonyl-4-piperidyl)pyrazolo[3,4-d]pyrimidin-4-amine;
3-(3-Chloro-1H-indol-2-yl)-1-(trans-4-morpholinocyclohexyl)-1H-pyrazolo[3,4-d]pyrimidin-4-amine;
N-[4-[trans-4-Amino-3-(3-chloro-1H-indol-2-yl)pyrazolo[3,4-d]pyrimidin-1-yl]cyclohexyl]cyclopropanecarboxamide;
1-tert-Butyl-3-{3-chloro-1H-pyrrolo[2,3-b]pyridin-2-yl}-1H-pyrazolo[3,4-d]pyrimidin-4-amine;
3-(3-Chloro-1H-indol-2-yl)-1-(propan-2-yl)-1H-pyrazolo[4,3-c]pyridin-4-amine;
5-(3-Chloro-1H-indol-2-yl)-7-(propan-2-yl)pyrrolo[2,1-f][1,2,4]triazin-4-amine;
3-(6-Bromo-3-chloro-1H-indol-2-yl)-1-isopropyl-pyrazolo[3,4-d]pyrimidin-4-amine;
2-(4-Amino-1-(tert-butyl)-1H-pyrazolo[3,4-d]pyrimidin-3-yl)-3-chloro-1H-indole-6-carbonitrile;
(2-(4-Amino-1-(tert-butyl)-1H-pyrazolo[3,4-d]pyrimidin-3-yl)-3-chloro-1H-indol-6-yl)methanol;
3-{3-Chloro-1H-pyrrolo[2,3-b]pyridin-2-yl}-1-(1-methanesulfonylpiperidin-4-yl)-1H-pyrazolo[3,4-d]pyrimidin-4-amine;
1-tert-Butyl-3-(3,6-dichloro-1H-indol-2-yl)-1H-pyrazolo[3,4-d]pyrimidin-4-amine;
1-tert-Butyl-3-{3-chloro-6-[(methylamino)methyl]-1H-indol-2-yl}-1H-pyrazolo[3,4-d]pyrimidin-4-amine;
1-tert-Butyl-3-[3-chloro-6-(methoxymethyl)-1H-indol-2-yl]-1H-pyrazolo[3,4-d]pyrimidin-4-amine;
tert-Butyl N-[cis-4-(4-amino-3-{3-chloro-1H-pyrrolo[2,3-b]pyridin-2-yl}-1H-pyrazolo[3,4-d]pyrimidin-1-yl)cyclohexyl]carbamate;
tert-Butyl N-[trans-4-(4-amino-3-{3-chloro-1H-pyrrolo[2,3-b]pyridin-2-yl}-1H-pyrazolo[3,4-d]pyrimidin-1-yl)cyclohexyl]carbamate;
3-(3-Chloro-1H-pyrrolo[2,3-b]pyridin-2-yl)-1-isopropyl-1H-pyrazolo[4,3-c]pyridin-4-amine;
3-(3-bromo-1H-pyrrolo[2,3-b]pyridin-2-yl)-1-(tert-butyl)-1H-pyrazolo[3,4-d]pyrimidin-4-amine;
3-(6-(Aminomethyl)-3-chloro-1H-indol-2-yl)-1-(tert-butyl)-1H-pyrazolo[3,4-d]pyrimidin-4-amine;
1-(cis-4-Aminocyclohexyl)-3-(3-chloro-1H-pyrrolo[2,3-b]pyridin-2-yl)-1H-pyrazolo[3,4-d]pyrimidin-4-amine dihydrochloride;

5-(3-Chloro-1H-pyrrolo[2,3-b]pyridin-2-yl)-7-isopropyl-pyrrolo[2,3-d]pyrimidin-4-amine;
3-(3-Chloro-1H-pyrrolo[2,3-b]pyridin-2-yl)-1-ethyl-pyrazolo[3,4-d]pyrimidin-4-amine;
5-(3-Chloro-1H-indol-2-yl)-7-isopropyl-pyrrolo[2,3-d]pyrimidin-4-amine;
3-(3-Bromo-1H-indol-2-yl)-1-(tert-butyl)-1H-pyrazolo[3,4-d]pyrimidin-4-amine;
1-(tert-Butyl)-3-(3,5-dichloro-1H-pyrrolo[2,3-b]pyridin-2-yl)-1H-pyrazolo[3,4-d]pyrimidin-4-amine;
2-(2-(4-Amino-1-(tert-butyl)-1H-pyrazolo[3,4-d]pyrimidin-3-yl)-3-chloro-1H-indol-6-yl)propan-2-ol;
3-(3-Chloro-1H-pyrrolo[2,3-b]pyridin-2-yl)-1-isopropyl-1H-pyrazolo[3,4-d]pyrimidin-4-amine;
3-(3-Chloro-1H-pyrrolo[2,3-b]pyridin-2-yl)-1-(tetrahydro-2H-pyran-4-yl)-1H-pyrazolo[3,4-d]pyrimidin-4-amine;
4-((4-Amino-3-(3-chloro-1H-pyrrolo[2,3-b]pyridin-2-yl)-1H-pyrazolo[3,4-c]pyrimidin-1-yl)methyl)benzonitrile;
1-(Azetidin-3-yl)-3-(3-chloro-1H-pyrrolo[2,3-b]pyridin-2-yl)-1H-pyrazolo[3,4-d]pyrimidin-4-amine;
3-(3-Chloro-1H-pyrrolo[2,3-b]pyridin-2-yl)-1-((tetrahydro-2H-pyran-4-yl)methyl)-1H-pyrazolo[3,4-d]pyrimidin-4-amine;
3-(3-Chloro-1H-pyrrolo[2,3-b]pyridin-2-yl)-1-((tetrahydro-2H-pyran-2-yl)methyl)-1H-pyrazolo[3,4-d]pyrimidin-4-amine;
3-(3-Chloro-1H-pyrrolo[2,3-b]pyridin-2-yl)-1-(2,2,2-trifluoroethyl)-1H-pyrazolo[3,4-d]pyrimidin-4-amine;
1-(sec-Butyl)-3-(3-chloro-1H-pyrrolo[2,3-b]pyridin-2-yl)-1H-pyrazolo[3,4-d]pyrimidin-4-amine;
3-(3-Chloro-1H-indol-2-yl)-1-cyclohexyl-pyrazolo[3,4-c]pyrimidin-4-amine;
3-(3-Chloro-1H-indol-2-yl)-1-isopropyl-pyrazolo[3,4-d]pyrimidin-4-amine;
3-(3-Chloro-1H-pyrrolo[2,3-b]pyridin-2-yl)-1-methyl-pyrazolo[3,4-d]pyrimidin-4-amine;
3-(3-Chloro-1H-pyrrolo[2,3-b]pyridin-2-yl)-1-cyclobutyl-pyrazolo[3,4-d]pyrimidin-4-amine;
3-(3-Chloro-1H-pyrrolo[2,3-b]pyridin-2-yl)-1-cyclohexyl-pyrazolo[3,4-d]pyrimidin-4-amine;
N-[trans-4-[4-Amino-3-(3-chloro-1H-pyrrolo[2,3-b]pyridin-2-yl)pyrazolo[3,4-d]pyrimidin-1-yl]cyclohexyl]cyclopropanecarboxamide;
3-[4-Amino-3-(3-chloro-1H-pyrrolo[2,3-b]pyridin-2-yl)pyrazolo[3,4-d]pyrimidin-1-yl]cyclopentanol;
1-tert-Butyl-3-(3-chloro-6-methyl-1H-indol-2-yl)pyrazolo[3,4-d]pyrimidin-4-amine;
1-(tert-Butyl)-3-(3-chloro-6-((di methylamino)methyl)-1H-indol-2-yl)-1H-pyrazolo[3,4-d]pyrimidin-4-amine;
1-(tert-Butyl)-3-(3-fluoro-1H-indol-2-yl)-1H-pyrazolo[3,4-d]pyrimidin-4-amine;
3-(3-Chloro-1H-pyrrolo[2,3-b]pyridin-2-yl)-1-(2-(4-(dimethylamino)piperidin-1-yl)ethyl)-1H-pyrazolo[3,4-d]pyrimidin-4-amine;
3-(3-Chloro-1H-pyrrolo[2,3-b]pyridin-2-yl)-1-(tetrahydrofuran-3-yl)-1H-pyrazolo[3,4-d]pyrimidin-4-amine;
3-(3-Chloro-1H-pyrrolo[2,3-b]pyridin-2-yl)-1-cyclopentyl-1H-pyrazolo[3,4-d]pyrimidin-4-amine;
3-(3-Chloro-1H-pyrrolo[2,3-b]pyridin-2-yl)-1-isopentyl-1H-pyrazolo[3,4-d]pyrimidin-4-amine;
3-(3-Chloro-1H-pyrrolo[2,3-b]pyridin-2-yl)-1-neopentyl-1H-pyrazolo[3,4-d]pyrimidin-4-amine;
3-(3-Chloro-1H-pyrrolo[2,3-b]pyridin-2-yl)-1-propyl-1H-pyrazolo[3,4-d]pyrimidin-4-amine;
1-tert-Butyl-3-(3-chloro-5-fluoro-1H-indol-2-yl)pyrazolo[3,4-d]pyrimidin-4-amine;
3-(3-Chloro-1H-indol-2-yl)-1-((tetrahydro-2H-pyran-4-yl)methyl)-1H-pyrazolo[3,4-d]pyrimidin-4-amine;
3-(3-Chloro-1H-indol-2-yl)-1-(tetrahydrofuran-3-yl)-1H-pyrazolo[3,4-d]pyrimidin-4-amine;
3-(3-Chloro-1H-pyrrolo[2,3-b]pyridin-2-yl)-1-(2-(piperidin-1-yl)ethyl)-1H-pyrazolo[3,4-d]pyrimidin-4-amine; or
1-tert-Butyl-3-(3,4-dichloro-1H-indol-2-yl)pyrazolo[3,4-d]pyrimidin-4-amine.

Additional compounds of the present invention include any of the compounds exemplified in the present application, or a pharmaceutically acceptable salt or solvate thereof, and, in particular, any of the following:
1-(tert-Butyl)-3-(1H-indol-2-yl)-1H-pyrazolo[3,4-d]pyrimidin-4-amine;
3-(1H-Indol-2-yl)-1-(1-methylsulfonyl-4-piperidyl)pyrazolo[3,4-d]pyrimidin-4-amine;
N-(trans-4-(4-Amino-3-(1H-indol-2-yl)-1H-pyrazolo[3,4-d]pyrimidin-1-yl)cyclohexyl)cyclopropanecarboxamide;
3-(1H-Indol-2-yl)-1-(trans-4-morpholinocyclohexyl)-1H-pyrazolo[3,4-d]pyrimidin-4-amine;
1-tert-Butyl-3-{1H-pyrrolo[2,3-b]pyridin-2-yl}-1H-pyrazolo[3,4-d]pyrimidin-4-amine;
3-(1H-Indol-2-yl)-1-(propan-2-yl)-1H-pyrazolo[4,3-c]pyridin-4-amine;
5-(1H-Indol-2-yl)-7-(propan-2-yl)pyrrolo[2,1-f][1,2,4]triazin-4-amine;
3-(6-Bromo-1H-indol-2-yl)-1-isopropyl-pyrazolo[3,4-d]pyrimidin-4-amine;
2-(4-Amino-1-(tert-butyl)-1H-pyrazolo[3,4-d]pyrimidin-3-yl)-1H-indole-6-carbonitrile;
1-(tert-Butyl)-3-(6-chloro-1H-indol-2-yl)-1H-pyrazolo[3,4-d]pyrimidin-4-amine;
7-Isopropyl-5-(1H-pyrrolo[2,3-b]pyridin-2-yl)pyrrolo[2,3-d]pyrimidin-4-amine;
1-(1-Methanesulfonylpiperidin-4-yl)-3-{1H-pyrrolo[2,3-b]pyridin-2-yl}-1H-pyrazolo[3,4-d]pyrimidin-4-amine;
tert-Butyl N-[cis-4-(4-amino-3-{1H-pyrrolo[2,3-b]pyridin-2-yl}-1H-pyrazolo[3,4-d]pyrimidin-1-yl)cyclohexyl]carbamate;
tert-Butyl (trans-4-(4-amino-3-(1H-pyrrolo[2,3-b]pyridin-2-yl)-1H-pyrazolo[3,4-d]pyrimidin-1-yl)cyclohexyl)carbamate;
1-Methyl-3-{1H-pyrrolo[2,3-b]pyridin-2-yl}-1H-pyrazolo[3,4-d]pyrimidin-4-amine;
1-Isopropyl-3-(1H-pyrrolo[2,3-b]pyridin-2-yl)-1H-pyrazolo[4,3-c]pyridin-4-amine;
N-(trans-4-(4-Amino-3-(1H-pyrrolo[2,3-b]pyridin-2-yl)-1H-pyrazolo[3,4-d]pyrimidin-1-yl)cyclohexyl)cyclopropanecarboxamide;
1-Isopropyl-3-(1H-pyrrolo[2,3-b]pyridin-2-yl)pyrazolo[3,4-d]pyrimidin-4-amine;
1-Cyclohexyl-3-(1H-indol-2-yl)pyrazolo[3,4-d]pyrimidin-4-amine;
3-[4-Amino-3-(1H-pyrrolo[2,3-b]pyridin-2-yl)pyrazolo[3,4-d]pyrimidin-1-yl]cyclopentanol;
1-Cyclohexyl-3-(1H-pyrrolo[2,3-b]pyridin-2-yl)pyrazolo[3,4-d]pyrimidin-4-amine;
1-Cyclobutyl-3-(1H-pyrrolo[2,3-b]pyridin-2-yl)pyrazolo[3,4-d]pyrimidin-4-amine;
1-Ethyl-3-(1H-pyrrolo[2,3-b]pyridin-2-yl)pyrazolo[3,4-d]pyrimidin-4-amine;
3-(1H-Indol-2-yl)-1-isopropyl-pyrazolo[3,4-d]pyrimidin-4-amine;
5-(1H-Indol-2-yl)-7-isopropyl-pyrrolo[2,3-d]pyrimidin-4-amine;
1-(tert-Butyl)-3-(5-chloro-1H-pyrrolo[2,3-b]pyridin-2-yl)-1H-pyrazolo[3,4-d]pyrimidin-4-amine;

N-(2-(4-Amino-1-(tert-butyl)-1H-pyrazolo[3,4-d]pyrimidin-3-yl)-1H-indol-6-yl)methanesulfonamide;
1-(2-(4-Amino-1-(tert-butyl)-1H-pyrazolo[3,4-d]pyrimidin-3-yl)-1H-indol-6-yl)-3-methylurea;
1-tert-Butyl-3-(6-methyl-1H-indol-2-yl)pyrazolo[3,4-d]pyrimidin-4-amine;
7-Chloro-1-isopropyl-3-(1H-pyrrolo[2,3-b]pyridin-2-yl)-1H-pyrazolo[4,3-c]pyridin-4-amine;
1-tert-Butyl-3-(5-fluoro-1H-indol-2-yl)pyrazolo[3,4-d]pyrimidin-4-amine;
1-tert-Butyl-3-(4-chloro-1H-indol-2-yl)pyrazolo[3,4-d]pyrimidin-4-amine;
1-tert-Butyl-3-(5-methyl-1H-indol-2-yl)pyrazolo[3,4-d]pyrimidin-4-amine;
2-(4-Amino-1-(tert-butyl)-1H-pyrazolo[3,4-d]pyrimidin-3-yl)-1H-pyrrolo[2,3-b]pyridine-6-carbonitrile; or
2-(4-Amino-1-tert-butyl-pyrazolo[3,4-d]pyrimidin-3-yl)-1H-indole-5-carbonitrile.

The various functional groups and substituents making up the compounds of the Formula (I), or sub-formulae Ia to If, are typically chosen such that the molecular weight of the compound of the formula (I) does not exceed 1000. More usually, the molecular weight of the compound will be less than 900, for example less than 800, or less than 750, or less than 700, or less than 650. More preferably, the molecular weight is less than 600 and, for example, is 550 or less.

A suitable pharmaceutically acceptable salt of a compound of the invention is, for example, an acid-addition salt of a compound of the invention which is sufficiently basic, for example, an acid-addition salt with, for example, an inorganic or organic acid, for example hydrochloric, hydrobromic, sulfuric, phosphoric, trifluoroacetic, formic, citric methane sulfonate or maleic acid. In addition, a suitable pharmaceutically acceptable salt of a compound of the invention which is sufficiently acidic is an alkali metal salt, for example a sodium or potassium salt, an alkaline earth metal salt, for example a calcium or magnesium salt, an ammonium salt or a salt with an organic base which affords a pharmaceutically acceptable cation, for example a salt with methylamine, dimethylamine, trimethylamine, piperidine, morpholine or tris-(2-hydroxyethyl)amine.

Compounds that have the same molecular formula but differ in the nature or sequence of bonding of their atoms or the arrangement of their atoms in space are termed "isomers". Isomers that differ in the arrangement of their atoms in space are termed "stereoisomers". Stereoisomers that are not mirror images of one another are termed "diastereomers" and those that are non-superimposable mirror images of each other are termed "enantiomers". When a compound has an asymmetric center, for example, it is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture".

The compounds of this invention may possess one or more asymmetric centers; such compounds can therefore be produced as individual (R)- or (S)-stereoisomers or as mixtures thereof. Unless indicated otherwise, the description or naming of a particular compound in the specification and claims is intended to include both individual enantiomers and mixtures, racemic or otherwise, thereof. The methods for the determination of stereochemistry and the separation of stereoisomers are well-known in the art (see discussion in Chapter 4 of "Advanced Organic Chemistry", 4th edition J. March, John Wiley and Sons, New York, 2001), for example by synthesis from optically active starting materials or by resolution of a racemic form. Some of the compounds of the invention may have geometric isomeric centres (E- and Z-isomers). It is to be understood that the present invention encompasses all optical, diastereoisomers and geometric isomers and mixtures thereof that possess antiproliferative activity.

The present invention also encompasses compounds of the invention as defined herein which comprise one or more isotopic substitutions. For example, H may be in any isotopic form, including 1H, 2H(D), and 3H (T); C may be in any isotopic form, including 12C, 13C, and 14C; and O may be in any isotopic form, including 16O and 18O; and the like.

It is also to be understood that certain compounds of the Formula (I), or sub-formulae Ia to If, may exist in solvated as well as unsolvated forms such as, for example, hydrated forms. It is to be understood that the invention encompasses all such solvated forms that possess antiproliferative activity.

It is also to be understood that certain compounds of the Formula I, or sub-formulae Ia to If, may exhibit polymorphism, and that the invention encompasses all such forms that possess antiproliferative activity.

Compounds of the Formula I, or sub-formulae Ia to If, may exist in a number of different tautomeric forms and references to compounds of the Formula I, or sub-formulae Ia to If, include all such forms. For the avoidance of doubt, where a compound can exist in one of several tautomeric forms, and only one is specifically described or shown, all others are nevertheless embraced by Formula I, or sub-formulae Ia to If. Examples of tautomeric forms include keto-, enol-, and enolate-forms, as in, for example, the following tautomeric pairs: keto/enol (illustrated below), imine/enamine, amide/imino alcohol, amidine/amidine, nitroso/oxime, thioketone/enethiol, and nitro/aci-nitro.

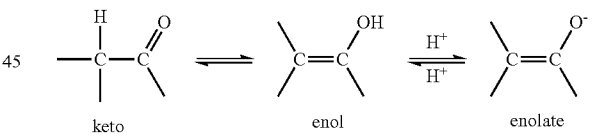

Compounds of the Formula I, or sub-formulae Ia to If, containing an amine function may also form N-oxides. A reference herein to a compound of the Formula I, or sub-formulae Ia to If, that contains an amine function also includes the N-oxide. Where a compound contains several amine functions, one or more than one nitrogen atom may be oxidised to form an N-oxide. Particular examples of N-oxides are the N-oxides of a tertiary amine or a nitrogen atom of a nitrogen-containing heterocycle. N-Oxides can be formed by treatment of the corresponding amine with an oxidizing agent such as hydrogen peroxide or a per-acid (e.g. a peroxycarboxylic acid), see for example Advanced Organic Chemistry, by Jerry March, 4th Edition, Wiley Interscience, pages. More particularly, N-oxides can be made by the procedure of L. W. Deady (Syn. Comm. 1977, 7, 509-514) in which the amine compound is reacted with m-chloroperoxybenzoic acid (mCPBA), for example, in an inert solvent such as dichloromethane.

The compounds of Formula (I), or sub-formulae Ia to If, may be administered in the form of a pro-drug which is broken down in the human or animal body to release a compound of the invention. A pro-drug may be used to alter the physical properties and/or the pharmacokinetic properties of a compound of the invention. A pro-drug can be formed when the compound of the invention contains a suitable group or substituent to which a property-modifying group can be attached. Examples of pro-drugs include in vivo cleavable ester derivatives that may be formed at a carboxy group or a hydroxy group in a compound of the Formula (I), or sub-formulae Ia to If, and in-vivo cleavable amide derivatives that may be formed at a carboxy group or an amino group in a compound of the Formula (I), or sub-formulae Ia to If.

Accordingly, the present invention includes those compounds of the Formula (I), or sub-formulae Ia to If, as defined hereinbefore, when made available by organic synthesis and when made available within the human or animal body by way of cleavage of a pro-drug thereof. Accordingly, the present invention includes those compounds of the Formula I, or sub-formulae Ia to If, that are produced by organic synthetic means and also such compounds that are produced in the human or animal body by way of metabolism of a precursor compound, that is a compound of the Formula (I), or sub-formulae Ia to If, may be a synthetically-produced compound or a metabolically-produced compound.

A suitable pharmaceutically acceptable pro-drug of a compound of the Formula (I), or sub-formulae Ia to If, is one that is based on reasonable medical judgement as being suitable for administration to the human or animal body without undesirable pharmacological activities and without undue toxicity.

Various forms of pro-drug have been described, for example in the following documents:—
a) Methods in Enzymology, Vol. 42, p. 309-396, edited by K. Widder, et al. (Academic Press, 1985);
b) Design of Pro-drugs, edited by H. Bundgaard, (Elsevier, 1985);
c) A Textbook of Drug Design and Development, edited by Krogsgaard-Larsen and H. Bundgaard, Chapter 5 "Design and Application of Pro-drugs", by H. Bundgaard p. 113-191 (1991);
d) H. Bundgaard, Advanced Drug Delivery Reviews, 8, 1-38 (1992);
e) H. Bundgaard, et al., Journal of Pharmaceutical Sciences, 77, 285 (1988);
f) N. Kakeya, et al., Chem. Pharm. Bull., 32, 692 (1984);
g) T. Higuchi and V. Stella, "Pro-Drugs as Novel Delivery Systems", A.C.S. Symposium Series, Volume 14; and
h) E. Roche (editor), "Bioreversible Carriers in Drug Design", Pergamon Press, 1987.

A suitable pharmaceutically acceptable pro-drug of a compound of the Formula I, or sub-formulae Ia to If, that possesses a carboxy group is, for example, an in vivo cleavable ester thereof. An in vivo cleavable ester of a compound of the Formula I, or sub-formulae Ia to If, containing a carboxy group is, for example, a pharmaceutically acceptable ester which is cleaved in the human or animal body to produce the parent acid. Suitable pharmaceutically acceptable esters for carboxy include C1-6alkyl esters such as methyl, ethyl and tert-butyl, C1-6alkoxymethyl esters such as methoxymethyl esters, C1-6alkanoyloxymethyl esters such as pivaloyloxymethyl esters, 3-phthalidyl esters, C3-8cycloalkylcarbonyloxy-C1-6alkyl esters such as cyclopentylcarbonyloxymethyl and 1-cyclohexylcarbonyloxyethyl esters, 2-oxo-1,3-dioxolenylmethyl esters such as 5-methyl-2-oxo-1,3-dioxolen-4-ylmethyl esters and C1-6alkoxycarbonyloxy-C1-6alkyl esters such as methoxycarbonyloxymethyl and 1-methoxycarbonyloxyethyl esters.

A suitable pharmaceutically acceptable pro-drug of a compound of the Formula (I), or sub-formulae Ia to If, that possesses a hydroxy group is, for example, an in vivo cleavable ester or ether thereof. An in vivo cleavable ester or ether of a compound of the Formula I, or sub-formulae Ia to If, containing a hydroxy group is, for example, a pharmaceutically acceptable ester or ether which is cleaved in the human or animal body to produce the parent hydroxy compound. Suitable pharmaceutically acceptable ester forming groups for a hydroxy group include inorganic esters such as phosphate esters (including phosphoramidic cyclic esters). Further suitable pharmaceutically acceptable ester forming groups for a hydroxy group include C1-10alkanoyl groups such as acetyl, benzoyl, phenylacetyl and substituted benzoyl and phenylacetyl groups, C1-10alkoxycarbonyl groups such as ethoxycarbonyl, N,N—(C1-6)2carbamoyl, 2-dialkylaminoacetyl and 2-carboxyacetyl groups. Examples of ring substituents on the phenylacetyl and benzoyl groups include aminomethyl, N-alkylaminomethyl, N,N-dialkylaminomethyl, morpholinomethyl, piperazin-1-ylmethyl and 4-(C1-4alkyl)piperazin-1-ylmethyl. Suitable pharmaceutically acceptable ether forming groups for a hydroxy group include α-acyloxyalkyl groups such as acetoxymethyl and pivaloyloxymethyl groups.

A suitable pharmaceutically acceptable pro-drug of a compound of the Formula (I), or sub-formulae Ia to If, that possesses a carboxy group is, for example, an in vivo cleavable amide thereof, for example an amide formed with an amine such as ammonia, a C1-4alkylamine such as methylamine, a (C1-4alkyl)2amine such as dimethylamine, N-ethyl-N-methylamine or diethylamine, a C1-4alkoxy-C2-4alkylamine such as 2-methoxyethylamine, a phenyl-C1-4alkylamine such as benzylamine and amino acids such as glycine or an ester thereof.

A suitable pharmaceutically acceptable pro-drug of a compound of the Formula I, or sub-formulae Ia to If, that possesses an amino group is, for example, an in vivo cleavable amide derivative thereof. Suitable pharmaceutically acceptable amides from an amino group include, for example an amide formed with C1-10alkanoyl groups such as an acetyl, benzoyl, phenylacetyl and substituted benzoyl and phenylacetyl groups. Examples of ring substituents on the phenylacetyl and benzoyl groups include aminomethyl, N-alkylaminomethyl, N,N-dialkylaminomethyl, morpholinomethyl, piperazin-1-ylmethyl and 4-(C1-4alkyl)piperazin-1-ylmethyl.

The in vivo effects of a compound of the Formula (I), or sub-formulae Ia to If, may be exerted in part by one or more metabolites that are formed within the human or animal body after administration of a compound of the Formula (I), or sub-formulae Ia to If. As stated hereinbefore, the in vivo effects of a compound of the Formula (I), or sub-formulae Ia to If, may also be exerted by way of metabolism of a precursor compound (a pro-drug).

Though the present invention may relate to any compound or particular group of compounds defined herein by way of optional, preferred or suitable features or otherwise in terms of particular embodiments, the present invention may also relate to any compound or particular group of compounds that specifically excludes said optional, preferred or suitable features or particular embodiments.

Suitably, the present invention excludes any individual compounds not possessing the biological activity defined herein.

Synthesis

The compounds of the present invention can be prepared by any suitable technique known in the art. Particular processes for the preparation of these compounds are described further in the accompanying examples.

In the description of the synthetic methods described herein and in any referenced synthetic methods that are used to prepare the starting materials, it is to be understood that all proposed reaction conditions, including choice of solvent, reaction atmosphere, reaction temperature, duration of the experiment and workup procedures, can be selected by a person skilled in the art.

It is understood by one skilled in the art of organic synthesis that the functionality present on various portions of the molecule must be compatible with the reagents and reaction conditions utilised.

It will be appreciated that during the synthesis of the compounds of the invention in the processes defined herein, or during the synthesis of certain starting materials, it may be desirable to protect certain substituent groups to prevent their undesired reaction. The skilled chemist will appreciate when such protection is required, and how such protecting groups may be put in place, and later removed.

For examples of protecting groups see one of the many general texts on the subject, for example, 'Protective Groups in Organic Synthesis' by Theodora Green (publisher: John Wiley & Sons). Protecting groups may be removed by any convenient method described in the literature or known to the skilled chemist as appropriate for the removal of the protecting group in question, such methods being chosen so as to effect removal of the protecting group with the minimum disturbance of groups elsewhere in the molecule.

Thus, if reactants include, for example, groups such as amino, carboxy or hydroxy it may be desirable to protect the group in some of the reactions mentioned herein.

By way of example, a suitable protecting group for an amino or alkylamino group is, for example, an acyl group, for example an alkanoyl group such as acetyl, an alkoxycarbonyl group, for example a methoxycarbonyl, ethoxycarbonyl or t-butoxycarbonyl group, an arylmethoxycarbonyl group, for example benzyloxycarbonyl, or an aroyl group, for example benzoyl. The deprotection conditions for the above protecting groups necessarily vary with the choice of protecting group. Thus, for example, an acyl group such as an alkanoyl or alkoxycarbonyl group or an aroyl group may be removed by, for example, hydrolysis with a suitable base such as an alkali metal hydroxide, for example lithium or sodium hydroxide. Alternatively an acyl group such as a tert-butoxycarbonyl group may be removed, for example, by treatment with a suitable acid as hydrochloric, sulfuric or phosphoric acid or trifluoroacetic acid and an arylmethoxycarbonyl group such as a benzyloxycarbonyl group may be removed, for example, by hydrogenation over a catalyst such as palladium-on-carbon, or by treatment with a Lewis acid for example boron tris(trifluoroacetate). A suitable alternative protecting group for a primary amino group is, for example, a phthaloyl group which may be removed by treatment with an alkylamine, for example dimethylaminopropylamine, or with hydrazine.

A suitable protecting group for a hydroxy group is, for example, an acyl group, for example an alkanoyl group such as acetyl, an aroyl group, for example benzoyl, or an arylmethyl group, for example benzyl. The deprotection conditions for the above protecting groups will necessarily vary with the choice of protecting group. Thus, for example, an acyl group such as an alkanoyl or an aroyl group may be removed, for example, by hydrolysis with a suitable base such as an alkali metal hydroxide, for example lithium, sodium hydroxide or ammonia. Alternatively an arylmethyl group such as a benzyl group may be removed, for example, by hydrogenation over a catalyst such as palladium-on-carbon.

A suitable protecting group for a carboxy group is, for example, an esterifying group, for example a methyl or an ethyl group which may be removed, for example, by hydrolysis with a base such as sodium hydroxide, or for example a t-butyl group which may be removed, for example, by treatment with an acid, for example an organic acid such as trifluoroacetic acid, or for example a benzyl group which may be removed, for example, by hydrogenation over a catalyst such as palladium-on-carbon.

Resins may also be used as a protecting group.

The methodology employed to synthesise a compound of Formula (I), or sub-formulae Ia to If, will vary depending on the nature of HET, $R_a$, $R_{1a}$, $R_{1b}$, W, $X_1$, $X_2$, $X_3$, $X_4$, $R_2$ and $R_3$ and any substituent groups associated therewith. Suitable processes for their preparation are described further in the accompanying Examples.

Once a compound of Formula (I), or sub-formulae Ia to If, has been synthesised by any one of the processes defined herein, the processes may then further comprise the additional steps of:
(i) removing any protecting groups present;
(ii) converting the compound Formula (I) into another compound of Formula (I);
(iii) forming a pharmaceutically acceptable salt, hydrate or solvate thereof; and/or
(iv) forming a prodrug thereof.

An example of (ii) above is when a compound of Formula (I) is synthesised and then one or more of the groups of HET, $R_1$, $R_{1a}$, $R_{1b}$, $R_{1b}$, $X_1$, $X_2$, $X_3$, $X_4$, $R_2$ and $R_3$ may be further reacted to change the nature of the group and provide an alternative compound of Formula (I). For example, the compound can be reacted to convert any R group into a substituent group other than hydrogen.

The resultant compounds of Formula (I), or sub-formulae Ia to If, can be isolated and purified using techniques well known in the art.

Biological Activity

The biological assays described in the Examples section herein may be used to measure the pharmacological effects of the compounds of the present invention.

Although the pharmacological properties of the compounds of Formula I vary with structural change, as expected, the compounds of the invention were found to be active in the RET assays described in the Examples section.

In general, the compounds of the invention demonstrate an $IC_{50}$ of 1 µM or less in the RET assay described in the Examples section, with preferred compounds of the invention demonstrating an $IC_{50}$ of 500 nM or less and the most preferred compounds of the invention demonstrating an $IC_{50}$ of 250 nM or less.

Suitably the ratio of RET activity to KDR activity measured in the RET and KDR assays set out in the Examples section herein is greater than 5, more suitably greater than 10, yet more suitably greater than 25, and most suitably greater than 50.

In the RET cell assay described herein in the Examples section, the compounds of Formula I suitably possess an activity of less than 1 µM, with the preferred compounds demonstrating an activity of 500 nM or less and the most preferred compounds of the invention demonstrating an IC$_{50}$ of 250 nM or less.

The following compound was tested but did not exhibit the desired activity in the assays described in the Examples section:

2-{4-amino-1-tert-butyl-1H-pyrazolo[3,4-d]pyrimidin-3-yl}-N-methyl-1H-indole-5-carboxamide;

1-tert-butyl-3-(1H-pyrrolo[3,2-b]pyridin-2-yl)pyrazolo[3,4-d]pyrimidin-4-amine;

2-(4-amino-3-(3-chloro-1H-pyrrolo[2,3-b]pyridin-2-yl)-1H-pyrazolo[3,4-d]pyrimidin-1-yl)acetic acid;

3-(3-chloro-1H-pyrrolo[2,3-b]pyridin-2-yl)-1-methyl-pyrazolo[3,4-d]pyrimidin-4-amine;

3-(3-chloro-1H-indol-2-yl)-1-isopentyl-1H-pyrazolo[3,4-d]pyrimidin-4-amine; and 3-(3-chloro-1H-indol-2-yl)-1-(pyrrolidin-3-ylmethyl)-1H-pyrazolo[3,4-d]pyrimidin-4-amine.

Pharmaceutical Compositions

According to a further aspect of the invention there is provided a pharmaceutical composition which comprises a compound of the invention as defined hereinbefore, or a pharmaceutically acceptable salt, hydrate or solvate thereof, in association with a pharmaceutically acceptable diluent or carrier.

The compositions of the invention may be in a form suitable for oral use (for example as tablets, lozenges, hard or soft capsules, aqueous or oily suspensions, emulsions, dispersible powders or granules, syrups or elixirs), for topical use (for example as creams, ointments, gels, or aqueous or oily solutions or suspensions), for administration by inhalation (for example as a finely divided powder or a liquid aerosol), for administration by insufflation (for example as a finely divided powder) or for parenteral administration (for example as a sterile aqueous or oily solution for intravenous, subcutaneous, intramuscular, intraperitoneal or intramuscular dosing or as a suppository for rectal dosing).

The compositions of the invention may be obtained by conventional procedures using conventional pharmaceutical excipients, well known in the art. Thus, compositions intended for oral use may contain, for example, one or more colouring, sweetening, flavouring and/or preservative agents.

An effective amount of a compound of the present invention for use in therapy is an amount sufficient to treat or prevent a proliferative condition referred to herein, slow its progression and/or reduce the symptoms associated with the condition.

The amount of active ingredient that is combined with one or more excipients to produce a single dosage form will necessarily vary depending upon the individual treated and the particular route of administration. For example, a formulation intended for oral administration to humans will generally contain, for example, from 0.5 mg to 0.5 g of active agent (more suitably from 0.5 to 100 mg, for example from 1 to 30 mg) compounded with an appropriate and convenient amount of excipients which may vary from about 5 to about 98 percent by weight of the total composition.

The size of the dose for therapeutic or prophylactic purposes of a compound of the formula I will naturally vary according to the nature and severity of the conditions, the age and sex of the animal or patient and the route of administration, according to well-known principles of medicine.

In using a compound of the invention for therapeutic or prophylactic purposes it will generally be administered so that a daily dose in the range, for example, 0.1 mg/kg to 75 mg/kg body weight is received, given if required in divided doses. In general lower doses will be administered when a parenteral route is employed. Thus, for example, for intravenous or intraperitoneal administration, a dose in the range, for example, 0.1 mg/kg to 30 mg/kg body weight will generally be used. Similarly, for administration by inhalation, a dose in the range, for example, 0.05 mg/kg to 25 mg/kg body weight will be used. Oral administration may also be suitable, particularly in tablet form. Typically, unit dosage forms will contain about 0.5 mg to 0.5 g of a compound of this invention.

Therapeutic Uses and Applications

The present invention provides compounds that function as inhibitors of RET or mutant forms thereof (e.g. RET$^{V804M}$). Furthermore, the compounds of the present invention demonstrate an improved selectivity for RET, or mutant forms thereof (e.g. RET$^{V804M}$), relative to KDR (i.e. they are potent inhibitors of RET and poor inhibitors of KDR).

The present invention therefore provides a method of inhibiting RET kinase enzyme activity, or mutant forms thereof (e.g. RET$^{V804M}$), in vitro or in vivo, said method comprising contacting a cell with an effective amount of a compound, or a pharmaceutically acceptable salt, hydrate or solvate thereof, as defined herein.

The present invention also provides a method of selectively inhibiting RET kinase enzyme activity, or mutant forms thereof (e.g. RET$^{V804M}$), over KDR enzyme activity in vitro or in vivo, said method comprising contacting a cell with an effective amount of a compound, or a pharmaceutically acceptable salt, hydrate or solvate thereof, as defined herein.

The present invention also provides a method of treating a disease or disorder in which RET kinase activity is implicated in a patient in need of such treatment, said method comprising administering to said patient a therapeutically effective amount of a compound, or a pharmaceutically acceptable salt, hydrate or solvate thereof, or a pharmaceutical composition as defined herein.

The present invention provides a method of inhibiting cell proliferation, in vitro or in vivo, said method comprising contacting a cell with an effective amount of a compound, or a pharmaceutically acceptable salt, hydrate or solvate thereof, as defined herein.

The present invention provides a method of treating a proliferative disorder in a patient in need of such treatment, said method comprising administering to said patient a therapeutically effective amount of a compound, or a pharmaceutically acceptable salt, hydrate or solvate thereof, or a pharmaceutical composition as defined herein.

The present invention provides a method of treating cancer in a patient in need of such treatment, said method comprising administering to said patient a therapeutically effective amount of a compound, or a pharmaceutically acceptable salt, hydrate or solvate thereof, or a pharmaceutical composition as defined herein.

The present invention provides a compound, or a pharmaceutically acceptable salt, hydrate or solvate thereof, or a pharmaceutical composition as defined herein for use in therapy.

The present invention provides a compound, or a pharmaceutically acceptable salt, hydrate or solvate thereof, or a pharmaceutical composition as defined herein for use in the treatment of a proliferative condition.

The present invention provides a compound, or a pharmaceutically acceptable salt, hydrate or solvate thereof, or a pharmaceutical composition as defined herein for use in the treatment of cancer. In a particular embodiment, the cancer is human cancer.

The present invention provides a compound, or a pharmaceutically acceptable salt, hydrate or solvate thereof, as defined herein for use in the inhibition of RET kinase enzyme activity, or mutant forms thereof (e.g. RET$^{V804M}$).

The present invention provides a compound, or a pharmaceutically acceptable salt, hydrate or solvate thereof, as defined herein for use in the selective inhibition of RET kinase enzyme activity, or mutant forms thereof (e.g. RET$^{V804M}$), over KDR enzyme activity.

The present invention provides a compound, or a pharmaceutically acceptable salt, hydrate or solvate thereof, as defined herein for use in the treatment of a disease or disorder in which RET kinase activity is implicated.

The present invention provides a use of a compound, or a pharmaceutically acceptable salt, hydrate or solvate thereof, as defined herein in the manufacture of a medicament for the treatment of a proliferative condition.

The present invention provides a use of a compound, or a pharmaceutically acceptable salt, hydrate or solvate thereof, as defined herein in the manufacture of a medicament for the treatment of cancer. Suitably, the medicament is for use in the treatment of human cancers.

The present invention provides a use of a compound, or a pharmaceutically acceptable salt, hydrate or solvate thereof, as defined herein in the manufacture of a medicament for the inhibition of RET kinase enzyme activity, or mutant forms thereof (e.g. RET$^{V804M}$).

The present invention provides a use of a compound, or a pharmaceutically acceptable salt, hydrate or solvate thereof, as defined herein in the manufacture of a medicament for the selective inhibition of RET kinase enzyme activity, or mutant forms thereof (e.g. RET$^{V804M}$), over KDR enzyme activity.

The present invention provides a use of a compound, or a pharmaceutically acceptable salt, hydrate or solvate thereof, as defined herein in the manufacture of a medicament for the treatment of a disease or disorder in which RET kinase activity is implicated.

The term "proliferative disorder" are used interchangeably herein and pertain to an unwanted or uncontrolled cellular proliferation of excessive or abnormal cells which is undesired, such as, neoplastic or hyperplastic growth, whether in vitro or in vivo. Examples of proliferative conditions include, but are not limited to, pre-malignant and malignant cellular proliferation, including but not limited to, malignant neoplasms and tumours, cancers, leukemias, psoriasis, bone diseases, fibroproliferative disorders (e.g., of connective tissues), and atherosclerosis. Any type of cell may be treated, including but not limited to, lung, colon, breast, ovarian, prostate, liver, pancreas, brain, and skin.

The anti-proliferative effects of the compounds of the present invention have particular application in the treatment of human cancers (by virtue of their inhibition of RET kinase enzyme activity, and/or the selective inhibition of RET kinase enzyme activity over KDR enzyme activity).

The anti-cancer effect may arise through one or more mechanisms, including but not limited to, the regulation of cell proliferation, the inhibition of angiogenesis (the formation of new blood vessels), the inhibition of metastasis (the spread of a tumour from its origin), the inhibition of invasion (the spread of tumour cells into neighbouring normal structures), or the promotion of apoptosis (programmed cell death).

In a particular embodiment of the invention, the proliferative condition to be treated is cancer, for example medullary thyroid cancer (MTC) or non-small cell lung cancer (NSCLC).

Routes of Administration

The compounds of the invention or pharmaceutical compositions comprising these compounds may be administered to a subject by any convenient route of administration, whether systemically/peripherally or topically (i.e., at the site of desired action).

Routes of administration include, but are not limited to, oral (e.g, by ingestion); buccal; sublingual; transdermal (including, e.g., by a patch, plaster, etc.); transmucosal (including, e.g., by a patch, plaster, etc.); intranasal (e.g., by nasal spray); ocular (e.g., by eye drops); pulmonary (e.g., by inhalation or insufflation therapy using, e.g., via an aerosol, e.g., through the mouth or nose); rectal (e.g., by suppository or enema); vaginal (e.g., by pessary); parenteral, for example, by injection, including subcutaneous, intradermal, intramuscular, intravenous, intra-arterial, intracardiac, intrathecal, intraspinal, intracapsular, subcapsular, intraorbital, intraperitoneal, intratracheal, subcuticular, intraarticular, subarachnoid, and intrasternal; by implant of a depot or reservoir, for example, subcutaneously or intramuscularly.

Combination Therapies

The antiproliferative treatment defined hereinbefore may be applied as a sole therapy or may involve, in addition to the compound of the invention, conventional surgery or radiotherapy or chemotherapy. Such chemotherapy may include one or more of the following categories of anti-tumour agents:—

(i) other antiproliferative/antineoplastic drugs and combinations thereof, as used in medical oncology, such as alkylating agents (for example cis-platin, oxaliplatin, carboplatin, cyclophosphamide, nitrogen mustard, melphalan, chlorambucil, busulphan, temozolamide and nitrosoureas); antimetabolites (for example gemcitabine and antifolates such as fluoropyrimidines like 5-fluorouracil and tegafur, raltitrexed, methotrexate, cytosine arabinoside, and hydroxyurea); antitumour antibiotics (for example anthracyclines like adriamycin, bleomycin, doxorubicin, daunomycin, epirubicin, idarubicin, mitomycin-C, dactinomycin and mithramycin); antimitotic agents (for example vinca alkaloids like vincristine, vinblastine, vindesine and vinorelbine and taxoids like taxol and taxotere and polokinase inhibitors); and topoisomerase inhibitors (for example epipodophyllotoxins like etoposide and teniposide, amsacrine, topotecan and camptothecin);

(ii) cytostatic agents such as antioestrogens (for example tamoxifen, fulvestrant, toremifene, raloxifene, droloxifene and iodoxyfene), antiandrogens (for example bicalutamide, flutamide, nilutamide and cyproterone acetate), LHRH antagonists or LHRH agonists (for example goserelin, leuprorelin and buserelin), progestogens (for example megestrol acetate), aromatase inhibitors (for example as anastrozole, letrozole, vorazole and exemestane) and inhibitors of 5α-reductase such as finasteride;

(iii) anti-invasion agents [for example c-Src kinase family inhibitors like 4-(6-chloro-2,3-methylenedioxyanilino)-7-[2-(4-methylpiperazin-1-yl)ethoxy]-5-tetrahydropyran-4-yloxyquinazoline (AZD0530; International Patent Application WO 01/94341), N-(2-chloro-6-methylphenyl)-2-{6-[4-(2-hydroxyethyl)piperazin-1-yl]-2-methylpyrimidin-4-ylamino}thiazole-5-carboxamide (dasatinib, BMS-354825; *J. Med. Chem.*, 2004, 47, 6658-6661) and bosutinib (SKI-606), and metalloproteinase inhibitors like marimastat, inhibitors of urokinase plasminogen activator receptor function or antibodies to Heparanase];

(iv) inhibitors of growth factor function: for example such inhibitors include growth factor antibodies and growth factor receptor antibodies (for example the anti-erbB2 antibody trastuzumab [Herceptin™], the anti-EGFR antibody panitumumab, the anti-erbB1 antibody cetuximab [Erbitux, C225] and any growth factor or growth factor receptor antibodies disclosed by Stern et al. (Critical reviews in oncology/haematology, 2005, Vol. 54, pp 11-29); such inhibitors also include tyrosine kinase inhibitors, for example inhibitors of the epidermal growth factor family (for example EGFR family tyrosine kinase inhibitors such as N-(3-chloro-4-fluorophenyl)-7-methoxy-6-(3-morpholinopropoxy)quinazolin-4-amine (gefitinib, ZD1839), N-(3-ethynylphenyl)-6,7-bis(2-methoxyethoxy)quinazolin-4-amine (erlotinib, OSI-774) and 6-acrylamido-N-(3-chloro-4-fluorophenyl)-7-(3-morpholinopropoxy)-quinazolin-4-amine (CI 1033), erbB2 tyrosine kinase inhibitors such as lapatinib); inhibitors of the hepatocyte growth factor family; inhibitors of the insulin growth factor family; inhibitors of the platelet-derived growth factor family such as imatinib and/or nilotinib (AMN107); inhibitors of serine/threonine kinases (for example Ras/Raf signalling inhibitors such as farnesyl transferase inhibitors, for example sorafenib (BAY 43-9006), tipifarnib (R115777) and lonafarnib (SCH66336)), inhibitors of cell signalling through MEK and/or AKT kinases, c-kit inhibitors, abl kinase inhibitors, PI3 kinase inhibitors, Plt3 kinase inhibitors, CSF-1R kinase inhibitors, IGF receptor (insulin-like growth factor) kinase inhibitors; aurora kinase inhibitors (for example AZD1152, PH739358, VX-680, MLN8054, R763, MP235, MP529, VX-528 AND AX39459) and cyclin dependent kinase inhibitors such as CDK2 and/or CDK4 inhibitors;

(v) antiangiogenic agents such as those which inhibit the effects of vascular endothelial growth factor, [for example the anti-vascular endothelial cell growth factor antibody bevacizumab (Avastin™) and for example, a VEGF receptor tyrosine kinase inhibitor such as vandetanib (ZD6474), vatalanib (PTK787), sunitinib (SU11248), axitinib (AG-013736), pazopanib (GW 786034) and 4-(4-fluoro-2-methylindol-5-yloxy)-6-methoxy-7-(3-pyrrolidin-1-ylpropoxy) quinazoline (AZD2171; Example 240 within WO 00/47212), compounds such as those disclosed in International Patent Applications WO97/22596, WO 97/30035, WO 97/32856 and WO 98/13354 and compounds that work by other mechanisms (for example linomide, inhibitors of integrin αvβ3 function and angiostatin)];

(vi) vascular damaging agents such as Combretastatin A4 and compounds disclosed in International Patent Applications WO 99/02166, WO 00/40529, WO 00/41669, WO 01/92224, WO 02/04434 and WO 02/08213;

(vii) an endothelin receptor antagonist, for example zibotentan (ZD4054) or atrasentan;

(viii) antisense therapies, for example those which are directed to the targets listed above, such as ISIS 2503, an anti-ras antisense;

(ix) gene therapy approaches, including for example approaches to replace aberrant genes such as aberrant p53 or aberrant BRCA1 or BRCA2, GDEPT (gene-directed enzyme pro-drug therapy) approaches such as those using cytosine deaminase, thymidine kinase or a bacterial nitroreductase enzyme and approaches to increase patient tolerance to chemotherapy or radiotherapy such as multi-drug resistance gene therapy; and (x) immunotherapy approaches, including for example ex-vivo and in-vivo approaches to increase the immunogenicity of patient tumour cells, such as transfection with cytokines such as interleukin 2, interleukin 4 or granulocyte-macrophage colony stimulating factor, approaches to decrease T-cell anergy, approaches using transfected immune cells such as cytokine-transfected dendritic cells, approaches using cytokine-transfected tumour cell lines and approaches using anti-idiotypic antibodies.

In a particular embodiment, the antiproliferative treatment defined hereinbefore may involve, in addition to the compound of the invention, conventional surgery or radiotherapy or chemotherapy, wherein the chemotherapy may include one or more anti-tumour agents selected from procarbazine, carmustine, lomustine, irinotecan, temozolomide, cisplatin, carboplatin, methotrexate, etoposide, cyclophosphamide, ifosfamide, and vincristine.

Such conjoint treatment may be achieved by way of the simultaneous, sequential or separate dosing of the individual components of the treatment. Such combination products employ the compounds of this invention within the dosage range described hereinbefore and the other pharmaceutically-active agent within its approved dosage range.

According to this aspect of the invention there is provided a combination for use in the treatment of a cancer (for example a cancer involving a solid tumour) comprising a compound of the invention as defined hereinbefore, or a pharmaceutically acceptable salt, hydrate or solvate thereof, and another anti-tumour agent.

According to this aspect of the invention there is provided a combination for use in the treatment of a proliferative condition, such as cancer (for example a cancer involving a solid tumour), comprising a compound of the invention as defined hereinbefore, or a pharmaceutically acceptable salt, hydrate or solvate thereof, and any one of the anti-tumour agents listed herein above.

In a further aspect of the invention there is provided a compound of the invention or a pharmaceutically acceptable salt, hydrate or solvate thereof, for use in the treatment of cancer in combination with another anti-tumour agent, optionally selected from one listed herein above.

Herein, where the term "combination" is used it is to be understood that this refers to simultaneous, separate or sequential administration. In one aspect of the invention "combination" refers to simultaneous administration. In another aspect of the invention "combination" refers to separate administration. In a further aspect of the invention "combination" refers to sequential administration. Where the administration is sequential or separate, the delay in administering the second component should not be such as to lose the beneficial effect of the combination.

According to a further aspect of the invention there is provided a pharmaceutical composition which comprises a compound of the invention, or a pharmaceutically acceptable salt, hydrate or solvate thereof, in combination with an anti-tumour agent (optionally selected from one listed herein above), in association with a pharmaceutically acceptable diluent or carrier.

EXAMPLES

Abbreviations

Boc tert-butyloxycarbonyl
br s broad singlet
d doublet
dd doublet of doublets
$CDCl_3$ Chloroform
$CsCO_3$ Caesium carbonate DCM Dichloromethane (methylene chloride)
DMF N,N-dimethylformamide
DMSO Dimethylsulfoxide.
EtOAc Ethyl acetate
EtOH Ethanol (ethyl alcohol)
fcc flash column chromatography
HCl Hydrochloric acid
HPLC High Pressure Liquid Chromatography
Hz Hertz
J Coupling constant
LCMS Liquid Chromatography-Mass Spectrometry
m multiplet
MeOH Methanol (methyl alcohol)
MHz Mega hertz
MW microwave reactor
$N_2$ Nitrogen
$NaHCO_3$ Sodium Bicarbonate
$Na_2SO_4$ Sodium sulphate
NBS N-Bromosuccinimide
NCS N-Chlorosuccinimide
NMR Nuclear Magnetic Resonance
$Pd(dppf)Cl_2$ 1,1'-Bis(diphenylphosphino)ferrocene-palladium(II)dichloride
q quartet
s singlet
t triplet
TFA trifluoroacetic acid
Methods
General Experimental Flash column chromatography refers to automated chromatography using pre-packed silica cartridges.

Generally, in the experimental procedures described hereinbelow, flash chromatography was performed using pre-packed silica gel cartridge and thin layer chromatography was conducted with 5×10 cm plates coated with Merck Type 60 $F_{254}$ silica gel to a thickness of 0.25 mm. Typically, reagents obtained from commercial sources were used without further purification unless stated otherwise. Anhydrous solvents were commonly obtained from the Sigma-Aldrich Chemical Company Ltd. or Fisher Chemicals Ltd., and used without further drying. HPLC grade solvents were predominately obtained from Fisher Chemicals Ltd.

$^1$H NMR spectroscopy was carried out using various spectrometers in the stated solvent at room temperature unless stated otherwise. In all cases, NMR data were consistent with the proposed structure. Characteristic chemical shifts (δ) are given in parts-per-million using conventional abbreviations for designation of major peaks e.g. s, singlet; d, doublet; t, triplet; q, quartet; dd, doublet of doublets; br, broad. LCMS was run using various spectrometers to generate low resolution mass spectra under electron spray ionisation (ESI) conditions.

Generally, in the experimental procedures described hereinbelow, proton ($^1$H) NMR spectra were recorded on a 300 MHz or 400 MHz Bruker spectrometer. Solutions were typically prepared in either deuterochloroform ($CDCl_3$) or deuterated dimethylsulfoxide (DMSO-$d_6$) with chemical shifts referenced to tetramethylsilane (TMS) or deuterated solvent as an internal standard. Furthermore, deuterated solvents were typically obtained from the Sigma-Aldrich Chemical Company, Goss or Fluorochem.

LCMS Methods
Analytical LC-MS.

It will be appreciated that various LC-MS conditions may be used in the analysis of the compounds of the present invention. Examples of some non-limiting LC-MS conditions are provided below.

Illustrative LC-MS Conditions

LC-MS analyses may be performed on, for example, a Waters Acquity UPLC system fitted with BEH C18 1.7 μM columns (2.1×50 mm or 2.1×100 mm), with UV diode array detection (210-400 nm). Positive and negative mass ion detection may also be performed using, for example, a Waters SQD detector. Analyses may then be performed with either buffered acidic or basic solvents, using gradients such as those detailed below.

Examples of Suitable Solvent Gradients
Low pH:
Solvent A—Water+10 mM ammonium formate+0.1% formic acid
Solvent B—Acetonitrile+5% water+0.1% formic acid
High pH:
Solvent A—Water+10 mM ammonium hydrogen carbonate+0.1% ammonia solution
Solvent B—Acetonitrile+0.1% ammonia solution
An Example of a Standard LC-MS Solvent Gradient:

| Time | Flow rate (mL/min) | % Solvent A | % Solvent B |
| --- | --- | --- | --- |
| 0 | 0.6 | 95 | 5 |
| 1.2 | 0.6 | 5 | 95 |
| 1.7 | 0.6 | 5 | 95 |
| 1.8 | 0.6 | 95 | 5 |

Preparative HPLC

Preparative HPLC refers to mass-directed reverse-phase chromatography using various water:MeCN eluent gradients. It will be appreciated that various preparative HPLC machines and/or conditions may be used to purify the compounds of the present invention, and the person skilled in the art will be well versed in selecting appropriate conditions for each respective compound. Nonetheless, details of some non-limiting examples of suitable HPLC conditions are provided below.

Illustrative Preparative HPLC Conditions

Compounds may be purified by preparative HPLC on, for example, a Waters FractionLynx MS autopurification system, with a column such as a Waters XBridge 5 μm C18, 100 mm×19 mm i.d. column, running at a typical flow rate of 20 mL/min with UV diode array detection (210-400 nm) and mass-directed collection using both positive and negative mass ion detection.

Purifications may also be performed using buffered acidic or basic solvent systems, as appropriate. Compound retention times on such systems may then be assessed using a 30-50 μL test injection and a standard gradient, and then purified using an appropriately chosen focused gradient as detailed below, based upon observed retention time.

Some typically examples of suitable solvent gradients include:
Low pH:
Solvent A—Water+10 mM ammonium formate+0.1% formic acid
Solvent B—Acetonitrile+5% water+0.1% formic acid
High pH:
Solvent A—Water+10 mM ammonium formate+0.1% ammonia solution
Solvent B—Acetonitrile+5% water+0.1% ammonia solution An Example of a Standard HPLC Gradient:

| Time | Flow rate (mL/min) | % Solvent A | % Solvent B |
|---|---|---|---|
| 0 | 20 | 90 | 10 |
| 0.3 | 20 | 90 | 10 |
| 8.5 | 20 | 2 | 98 |
| 12 | 20 | 2 | 98 |
| 12.5 | 0 | 2 | 98 |

Examples of Some Focused HPLC Gradients:

| | | % Solvent B Retention time on standard gradient (min.) | | | | |
|---|---|---|---|---|---|---|
| Time | Flow rate (mL/min) | 0-5.2 | 4.9-6.6 | 6.3-7.5 | 7.3-9.5 | 9.3-12 |
| 0 | 20 | 10 | 10 | 10 | 10 | 10 |
| 0.25 | 20 | 10 | 10 | 10 | 10 | 10 |
| 0.35 | 20 | 10 | 20 | 35 | 45 | 60 |
| 10 | 20 | 45 | 55 | 65 | 75 | 98 |
| 12 | 20 | 98 | 98 | 98 | 98 | 98 |
| 12.5 | 0 | 98 | 98 | 98 | 98 | 98 |

Synthetic Methods

Several methods for the chemical synthesis of the compounds of the present invention are described herein. These and/or other well-known methods may be modified and/or adapted in known ways in order to facilitate the synthesis of additional compounds within the scope of the present invention.

Where the preparation of starting materials is not described, these are commercially available, known in the literature, or readily obtained by those skilled in the art using standard procedures. Where it is stated that compounds were prepared analogously to earlier examples or intermediates, using General Methods, it will be appreciated by the skilled person that the reaction time, number of equivalents of reagents and temperature can be modified for each specific reaction and that it may be desirable or necessary to employ different reagents, catalysts, work-up or purification techniques.

General Synthetic Schemes

Scheme 1 - Preparation of pyrazolopyrimidines D and E

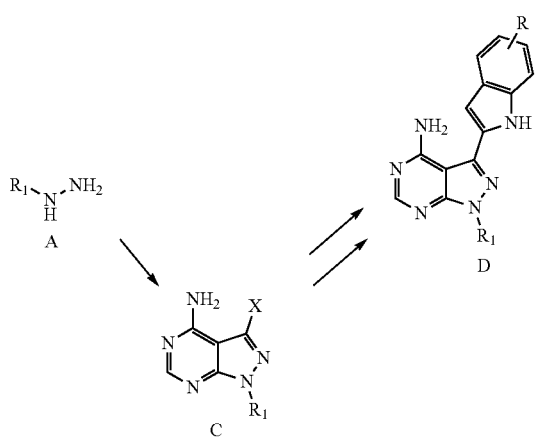

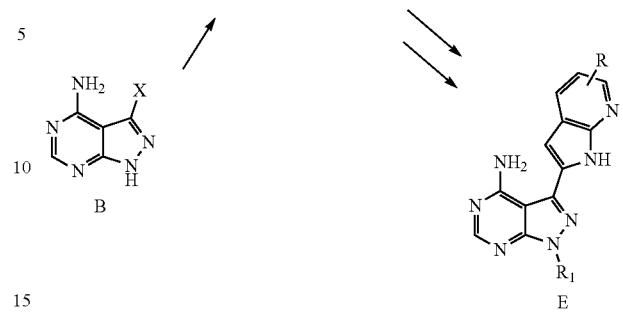

Substituted pyrazolopyrimidines C were prepared either via the known 3-step procedure from an appropriately substituted hydrazine A (General Method 1) or via elaboration of the unsubstituted pyrazolopyrimidine B (General Method 2). X is Br or I. Suzuki coupling of intermediate C with (aza)indolyl boronic acid derivatives (General Method 3) returned products D or E. In cases where the Suzuki coupling partner was Boc-protected, either the Boc group was lost during the Suzuki step or was formally deprotected using with HCl or TFA if mixtures of protected and deprotected products were obtained. Where necessary, further elaboration was conducted, such as chlorination using 1,3-dichloro-5,5-dimethylhydantoin (General Method 4) or NCS (General Method 5).

Scheme 2 - Preparation of 3-Cl azaindolyl pyrazolopyrimidines G

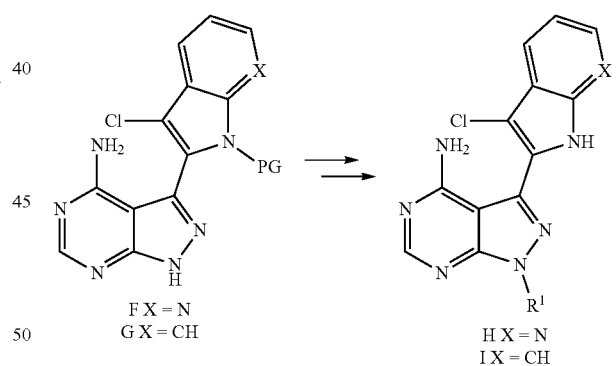

Advanced intermediates F and G were prepared as described below, then alkylated and deprotected (General Method 6 or 7) as an alternative synthesis to 3-Cl azaindoles H and 3-Cl indoles I.

General Methods

Representative procedures are provided to all General Methods although it will be appreciated that modifications to the procedures, work-up and isolation will be employed in individual preparations. In particular, in cases where Boc-protected intermediates are employed in Suzuki couplings, an additional treatment with HCl or TFA was included if deprotection did not occur thermally under the reaction conditions.

Synthesis of Intermediates
General Method 1—Representative Procedure

3-Bromo-1-cyclohexyl-1H-pyrazolo[3,4-d]pyrimidin-4-amine (Intermediate 1)

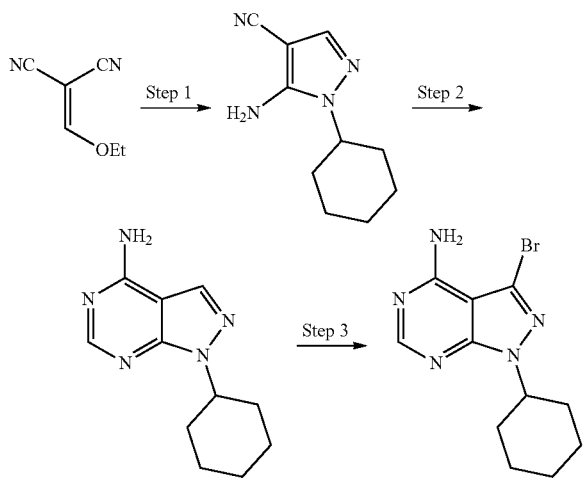

Step 1

To a mixture of Et$_3$N (1.39 mL, 10 mmol) and cyclohexylhydrazine hydrochloride (1.51 g, 10 mmol) in EtOH (35 mL) was added ethoxymethylenemalononitrile (1.22 g, 10 mmol) portion wise. The reaction mixture was heated at reflux for 5 h, then cooled to room temperature and concentrated in vacuo. The residue was taken up in EtOAc (50 mL) and washed with water (2×25 mL). The organic phase was dried over MgSO$_4$, filtered and concentrated in vacuo to return 5-amino-1-cyclohexyl-pyrazole-4-carbonitrile (1.95 g, 103%) as an orange solid which was used without further purification. $^1$H NMR (300 MHz, CDCl$_3$) δ 7.49 (s, 1H), 4.45 (s, 2H), 3.77 (tt, =J=11.2, 4.2 Hz, 1H), 1.88 (ddt, =J=17.4, 11.4, 5.4 Hz, 6H), 1.83-1.65 (m, 1H), 1.49-1.32 (m, 1H), 1.38-1.15 (m, 2H).

Step 2

A suspension of 5-amino-1-cyclohexyl-pyrazole-4-carbonitrile (1.95 g, 10 mmol) in formamide (15 mL) was heated at 180° C. for 1 h in the MW. The reaction was cooled to room temperature then diluted with water (50 mL) and extracted with EtOAc (3×50 mL). The combined organics were washed with brine (50 mL), dried over MgSO$_4$, filtered and concentrated in vacuo to return 1-cyclohexylpyrazolo[3,4-d]pyrimidin-4-amine (2.01 g, 90%) as a light brown solid which was used without further purification. $^1$H NMR (300 MHz, DMSO-d$_6$) δ 8.15 (s, 1H), 8.06 (s, 1H), 7.64 (br s, 1H), 4.57 (tt, =J=9.5, 4.9 Hz, 1H), 2.0-1.78 (m, 6H), 1.69 (d, =J=13.0 Hz, 1H), 1.48-1.13 (m, 3H).

Step 3

To a suspension of 1-cyclohexylpyrazolo[3,4-d]pyrimidin-4-amine (2.01 g, 9.3 mmol) in water (50 mL) was added bromine (0.95 mL, 18.5 mmol). The reaction was heated at reflux for 4 h then cooled to room temperature and extracted with EtOAc (3×50 mL). The combined organics were washed sequentially with 5% aq. sodium bisulfite (25 mL), sat. aq. NaHCO$_3$ (25 mL) and brine (25 mL), dried over MgSO$_4$, filtered and concentrated in vacuo to return the title compound (1.58 g, 58%) as an orange solid which was used without further purification. LCMS [M+H]$^+$ 296 and 298; $^1$H NMR (300 MHz, DMSO-d$_6$) δ 8.19 (s, 1H), 7.92 (s, 2H), 4.57 (dt, =J=9.5, 5.2 Hz, 1H), 1.92-1.72 (m, 5H), 1.67 (d, =J=12.9 Hz, 1H), 1.52-1.31 (m, 2H), 1.31-1.12 (m, 1H).

Also prepared by this method:

3-Bromo-1-ethyl-1H-pyrazolo[3,4-d]pyrimidin-4-amine (Intermediate 2)

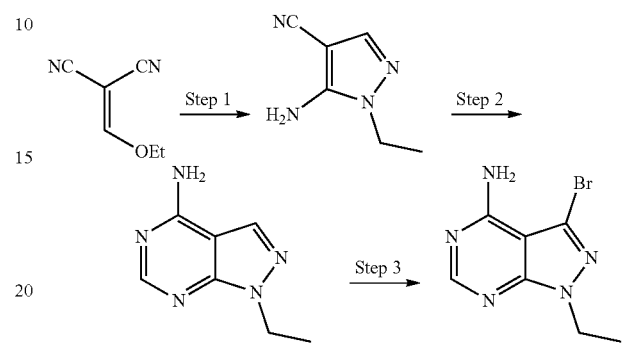

Step 1

1.8 g (16%) as a white solid. $^1$H NMR (300 MHz, DMSO-d$_6$) δ 7.52 (s, 1H), 6.54 (s, 2H), 3.89 (q, =J=7.2 Hz, 2H), 1.20 (t, =J=7.2 Hz, 3H).

Step 2

850 mg (39%) as a yellow solid. LCMS [M−H]$^-$ 162.0; 1H NMR (300 MHz, DMSO-d$_6$) δ 8.16 (s, 1H), 8.07 (s, 1H), 7.70 (s, 2H), 4.30 (q, J=7.2 Hz, 2H), 1.36 (t, J=7.2 Hz, 3H).

Step 3

870 mg (62%) as a solid. LCMS [M+H]$^+$ 242.0 and 244.0; $^1$H NMR (300 MHz, DMSO-d$_6$) δ 8.21 (s, 1H), 7.88 (s, 1H), 6.99 (s, 1H), 4.28 (q, J=7.2 Hz, 2H), 1.36 (t, J=7.2 Hz, 3H).

General Method 2—Representative Procedure

Common alkylating agents to prepare other intermediates were usually the requisite mesylate or halide.

3-Bromo-1-(1-(methylsulfonyl)piperidin-4-yl)-1H-pyrazolo[3,4-d]pyrimidin-4-amine (Intermediate 3)

A mixture of 3-bromo-1H-pyrazolo[3,4-d]pyrimidin-4-amine (1.0 g, 4.67 mmol), 1-(methylsulfonyl)piperidin-4-yl methanesulfonate (1.26 g, 4.90 mmol) and Cs$_2$CO$_3$ (3.04 g, 9.34 mmol) in DMF (22 mL) was heated at 80° C. under N$_2$ for 24 hours. The reaction was cooled to room temperature, diluted with water and extracted with EtOAc (3×). The combined organic extracts were dried over Na$_2$SO$_4$, filtered and concentrated in vacuo. The residue was triturated with DCM/MeOH and the resultant solid was isolated by filtration, washed with DCM and dried in vacuo to return the title compound (838 mg, 48%) as a white solid. LCMS [M+H]$^+$ 375 and 377; $^1$H NMR (300 MHz, DMSO-d$_6$) δ 8.22 (s, 1H), 4.71-4.84 (m, 1H), 3.69 (br d, =J=12.06 Hz, 2H), 2.99 (dt, =J=3.01, 12.06 Hz, 2H), 2.93 (s, 3H), 1.97-2.18 (m, 4H).

General Method 3—Representative Procedure

Coupling partners were typically the requisite heteroaryl bromide although iodides were used on some occasions. In cases where the heteroaryl partner was not the pyrazolopyrimidine, the corresponding heteroaryl was either prepared as detailed below, or by the reported literature methods, or employed in the Suzuki coupling.

The requisite boronic acids or esters were employed according to commercial availability or route of synthesis and variably bore a protecting group on the (aza)indole NH e.g. Boc or SEM.

Example 1—1-(tert-Butyl)-3-(1H-indol-2-yl)-1H-pyrazolo[3,4-d]pyrimidin-4-amine A mixture of 3-bromo-1-(tert-butyl)-1H-pyrazolo[3,4-d]pyrimidin-4-amine (200 mg, 0.74 mmol), (1-(tert-butoxycarbonyl)-1H-indol-2-yl)boronic acid (232 mg, 0.89 mmol), Pd(dppf)Cl$_2$.DCM (6 mg, 0.01 mmol) and aq. Na$_2$CO$_3$ (1M, 1.48 mL, 1.48 mmol) in 1,4-dioxane (2 mL) was heated to 100° C. in the microwave for 30 min. The reaction mixture was diluted with water and extracted with EtOAc (3×). The combined organic phases were filtered through celite and concentrated in vacuo to return a residue which was a mixture of the Boc-protected and the deprotected material. The residue was dissolved in DCM (2 mL), cooled in an ice bath and treated with TFA (1.0 mL, 13.46 mmol). The reaction was stirred at room temperature for 18 h, concentrated in vacuo and partitioned between EtOAc and sat. aq. NaHCO$_3$. The aqueous was further extracted with EtOAc (2×). The combined organic phases were concentrated to give a residue which was purified by preparative HPLC to return the title compound (35 mg, 15%) as a white solid. LCMS [M+H]$^+$ 307.2; $^1$H NMR (300 MHz, DMSO-d$_6$) δ 11.54 (br s, 1H), 8.26 (s, 1H), 7.62 (d, J=7.82 Hz, 1H), 7.48 (d, J=8.01 Hz, 1H), 7.13-7.21 (m, 1H), 7.05 (t, J=7.02 Hz, 1H), 6.82 (s, 1H), 1.79 (s, 9H).

General Method 4—Representative Procedure

Example 3—1-tert-Butyl-3-(3-chloro-1H-indol-2-yl)pyrazolo[3,4-d]pyrimidin-4-amine To a solution of 1-tert-butyl-3-(1H-indol-2-yl)pyrazolo[3,4-d]pyrimidin-4-amine (63 mg, 0.21 mmol) in 1,4-dioxane (2 mL) was added 1,3-dichloro-5,5-dimethylhydantoin (20 mg, 0.10 mmol) at room temperature. After 30 min, a further charge of 1,3-dichloro-5,5-dimethylhydantoin (10 mg, 0.05 mmol) was added. The reaction was stirred at room temperature for 30 min then diluted with sat. aq. NaHCO$_3$ and extracted with EtOAc (3×). The combined organics were concentrated in vacuo to give a residue which was purified by preparative HPLC to return the title compound (16 mg, 23%) as a white solid. LCMS [M−H]$^-$ 339.1; $^1$H NMR (300 MHz, DMSO-d$_6$) δ 11.87 (br s, 1H), 8.26 (s, 1H), 7.57 (d, J=7.54 Hz, 1H), 7.48 (d, J=8.10 Hz, 1H), 7.26 (br t, J=8.10 Hz, 1H), 7.19 (t, J=7.54 Hz, 1H), 1.78 (s, 9H).

General Method 5—Representative Procedure

Stoichiometric charge of chlorinating agents usually resulted in mixture of desired product, unreacted starting material and bischlorinated product in varying proportions. Occasionally the ratio could be improved by treating the crude product with NaBH$_4$ in MeOH or by including DI PEA at the end of the reaction. Often, the crude was purified without further manipulation.

Example 7—3-(3-Chloro-1H-indol-2-yl)-1-(trans-4-morpholinocyclohexyl)-1H-pyrazolo[3,4-d]pyrimidin-4-amine To a solution of 3-(1H-indol-2-yl)-1-(trans-4-morpholinocyclohexyl)-1H-pyrazolo[3,4-d]pyrimidin-4-amine (79 mg, 0.19 mmol) in DMF (2.5 mL) was added NCS (25 mg, 0.19 mmol) and the mixture stirred for 3 h at room temperature then at 70° C. for 2.5 h. The reaction mixture was cooled to room temperature, diluted with EtOAc (20 mL) and washed with brine (20 mL). The organic phase was filtered through a hydrophobic frit and the concentrated in vacuo to return the crude product which was purified by preparative HPLC to return the title compound (28 mg, 33%) as a white solid. LCMS [M−H]$^-$ 450.1 and 452.2; $^1$H NMR (300 MHz, DMSO-d$_6$) δ 11.87 (s, 1H), 8.26 (s, 1H), 7.57 (d, J=7.67 Hz, 1H), 7.48 (d, J=8.00 Hz, 1H), 7.27 (ddd, J=1.35, 6.99, 8.22 Hz, 1H), 7.19 (ddd, J=1.10, 7.02, 8.04 Hz, 1H), 6.96 (br s, 2H), 4.79-4.62 (m, 1H), 3.58 (t, J=4.54 Hz, 4H), 2.36 (t, J=11.39 Hz, 1H), 2.08-1.94 (m, 6H), 1.58-1.38 (m, 2H). 2×CH$_2$ under DMSO peak.

General Method 6—Representative Procedure

Example 55—3-(3-Chloro-1H-pyrrolo[2,3-b]pyridin-2-yl)-1-isopropyl-1H-pyrazolo[3,4-d]pyrimidin-4-amine Step 1

A suspension of 3-(3-chloro-1-((2-(trimethylsilyl)ethoxy)methyl)-1H-pyrrolo[2,3-b]pyridin-2-yl)-1H-pyrazolo[3,4-d]pyrimidin-4-amine (100 mg, 0.24 mmol), 2-iodopropane (25 μL, 0.25 mmol) and K$_2$CO$_3$ (134 mg, 0.97 mmol) in DMF (15 mL) was heated at 80° C. for 3 h. The reaction mixture was then cooled to room temperature and diluted with water (10 mL). The resulting precipitate was filtered, washed with further water (50 mL) and dried to return 3-(3-chloro-1-((2-(trimethylsilyl) ethoxy)methyl)-1H-pyrrolo[2,3-b]pyridin-2-yl)-1-isopropyl-1H-pyrazolo[3,4-d]pyrimidin-4-amine (67 mg, 76% pure by HPLC, 61%) as a beige solid. LCMS [M+H]$^+$ 458. This material was used in the subsequent step without additional purification.

Step 2

To a solution 3-(3-chloro-1-((2-(trimethylsilyl)ethoxy)methyl)-1H-pyrrolo[2,3-b]pyridin-2-yl)-1-isopropyl-1H-pyrazolo[3,4-d]pyrimidin-4-amine (67 mg, 0.15 mmol) in EtOH (5 mL) was added conc. HCl (0.14 mL) and the resulting mixture heated at 50° C. for 20 h. The solvent was concentrated in vacuo and the residue was treated with sat aq NaHCO$_3$ (5 mL) then extracted with EtOAc (3×10 mL). The combined organic extracts were washed with brine (20 mL), dried and concentrated in vacuo to return the crude product which was purified by fcc (0-10% MeOH in DCM) to return the title compound (8 mg, 17%) as a beige solid. LCMS [M+H]$^+$ 328; $^1$H NMR (400 MHz, DMSO-d$_6$) δ 12.42 (br, 1H), 8.37 (br d, J=5.0 Hz, 1H), 8.26 (s, 1H), 8.01 (br dd, J=7.9, 1.6 Hz, 1H), 7.24 (dd, J=7.9, 5.0 Hz, 1H), 7.05 (br, 2H), 5.10 (hept, J=6.6 Hz, 1H), 1.52 (d, J=6.6 Hz, 6H).

General Method 7—Representative Procedure 3-(3-Chloro-1H-indol-2-yl)-1-isopentyl-1H-pyrazolo[3,4-d]pyrimidin-4-amine

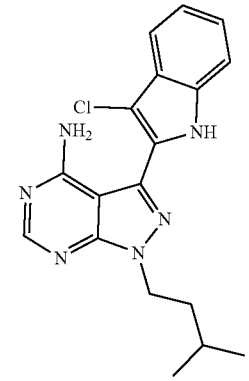 [SMILES: CC(C)CCn1nc(-c2[nH]c3ccccc3c2Cl)c2c(N)ncnc21]

Step 1

To a solution of 3-(3-chloro-1-((2-(trimethylsilyl)ethoxy)methyl)-1H-indol-2-yl)-1H-pyrazolo [3,4-d]pyrimidin-4-amine (86 mg, 0.20 mmol) in DMF (1 mL) was added 1-bromo-3-methyl-butane (25 μL, 0.21 mmol) and $K_2CO_3$ (81 mg, 0.59 mmol) and the resulting mixture heated at 80° C. for 18 h. The crude mixture was then cooled to room temperature and partitioned between EtOAc (10 mL) and water (10 mL). The organic layer was separated and retained and the aq phase was extracted with further EtOAc (2×10 mL). The combined organic extracts were washed with brine (5×10 mL), dried and concentrated in vacuo to return 3-(3-chloro-1-((2-(trimethylsilyl)ethoxy)methyl)-1H-indol-2-yl)-1-isopentyl-1H-pyrazolo [3,4-d]pyrimidin-4-amine (126 mg, 83% pure by HPLC) as a red oil. LCMS [M+H]+ 485. This material was used in the subsequent step without additional purification.

Step 2

To a solution of 3-(3-chloro-1-((2-(trimethylsilyl)ethoxy)methyl)-1H-indol-2-yl)-1-isopentyl-1H-pyrazolo [3,4-d]pyrimidin-4-amine (95 mg, 0.20 mmol) in 1,4-dioxane (2 mL) was added conc. HCl (0.19 mL) and the resulting mixture heated at 90° C. for 1.25 h. After cooling to room temperature, the reaction was concentrated in vacuo and the crude product was purified by fcc (0-10% MeOH/$NH_3$ (1%) in DCM) to return the title compound (30 mg, 43% yield over 2 steps) as a pale yellow solid. LCMS [M+H]+ 355; $^1$H NMR (400 MHz, DMSO-$d_6$) δ 11.98 (s, 1H), 8.45 (s, 1H), 7.59 (app d, 1H), 7.50 (app d, 1H), 7.30 (ddd, J=8.2, 7.0, 1.2 Hz, 1H), 7.21 (ddd, J=7.9, 7.0, 1.0 Hz, 1H), 4.46 (t, J=7.2 Hz, 2H), 1.80 (app q, 2H), 1.56 (hept, J=6.6 Hz, 1H), 0.94 (d, J=6.6 Hz 6H). $NH_2$ signals not observed.

TABLE A

| | | List of Intermediates and their method of synthesis | | |
|---|---|---|---|---|
| Intermediate | Name | | Structure | General Method |
| 1 | 3-Bromo-1-cyclohexyl-1H-pyrazolo[3,4-d]pyrimidin-4-amine | | | 1 |
| 2 | 3-Bromo-1-ethyl-1H-pyrazolo[3,4-d]pyrimidin-4-amine | | | 1 |
| 3 | 3-Bromo-1-(1-(methylsulfonyl)piperidin-4-yl)-1H-pyrazolo[3,4-d]pyrimidin-4-amine | | | 2 |
| 4 | 3-Bromo-1-cyclobutyl-1H-pyrazolo[3,4-d]pyrimidin-4-amine | | | 2 |

TABLE A-continued

List of Intermediates and their method of synthesis

| Intermediate | Name | Structure | General Method |
|---|---|---|---|
| 5 | tert-Butyl (trans-4-(4-amino-3-bromo-1H-pyrazolo[3,4-d]pyrimidin-1-yl)cyclohexyl)carbamate | 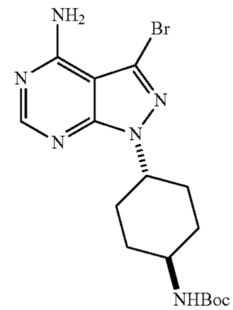 | 2 |
| 6 | tert-Butyl (cis-4-(4-amino-3-bromo-1H-pyrazolo[3,4-d]pyrimidin-1-yl)cyclohexyl)carbamate | 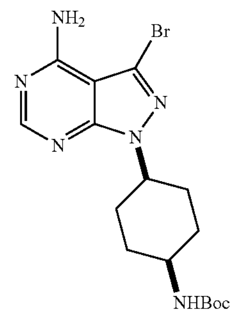 | 2 |
| 7 | 3-(4-Amino-3-bromo-1H-pyrazolo[3,4-d]pyrimidin-1-yl)cyclopentan-1-ol | 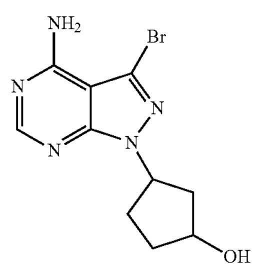 [SMILES: Nc1ncnc2c1c(Br)nn2C1CCC(O)C1] | See Below |
| 8 | 3-Bromo-1-methyl-1H-pyrazolo[3,4-c]pyrimidin-4-amine | 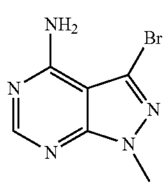 | See Below |
| 9 | 1-(trans-4-Aminocyclohexyl)-3-bromo-1H-pyrazolo[3,4-d]pyrimidin-4-amine trifluoroacetate | 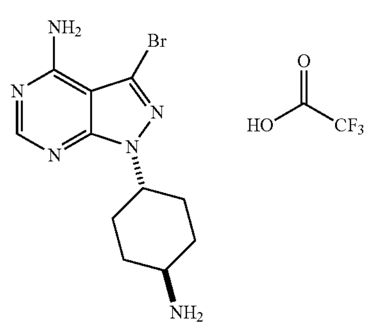 | See Below |

TABLE A-continued

List of Intermediates and their method of synthesis

| Intermediate | Name | Structure | General Method |
|---|---|---|---|
| 10 | N-(trans-4-(4-Amino-3-bromo-1H-pyrazolo[3,4-c]pyrimidin-1-yl)cyclohexyl)cyclopropanecarboxamide | 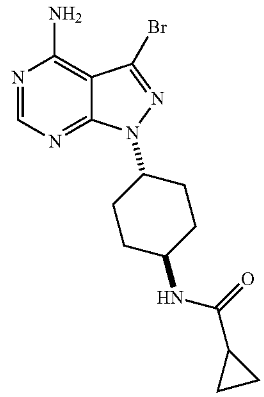 | See Below |
| 11 | N-(trans-4-(4-Amino-3-bromo-1H-pyrazolo[3,4-d]pyrimidin-1-yl)cyclohexyl)cyclopropanecarboxamide | 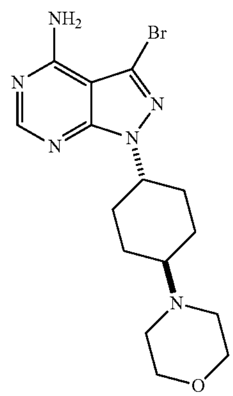 | See Below |
| 12 | Methyl 2-(4-amino-1-(tert-butyl)-1H-pyrazolo[3,4-d]pyrimidin-3-yl)-1H-indole-6-carboxylate | 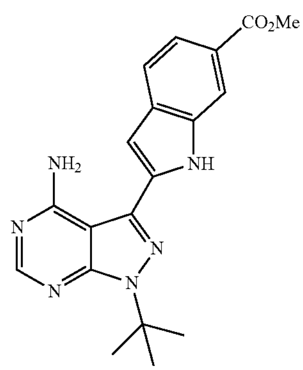 [SMILES: COC(=O)c1ccc2cc(-c3nn(C(C)(C)C)c4ncnc(N)c34)[nH]c2c1] | 3 |
| 13 | Methyl 2-(4-amino-1-(tert-butyl)-1H-pyrazolo[3,4-d]pyrimidin-3-yl)-3-chloro-1H-indole-6-carboxylate | 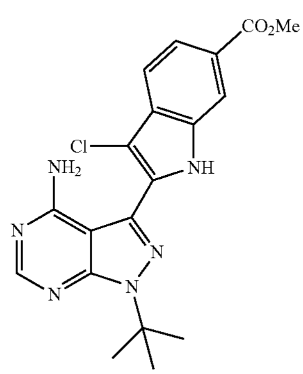 [SMILES: COC(=O)c1ccc2c(Cl)c(-c3nn(C(C)(C)C)c4ncnc(N)c34)[nH]c2c1] | 5 |

TABLE A-continued

List of Intermediates and their method of synthesis

| Intermediate | Name | Structure | General Method |
|---|---|---|---|
| 14 | 2-(4-Amino-1-(tert-butyl)-1H-pyrazolo[3,4-d]pyrimidin-3-yl)-3-chloro-1H-indole-6-carbaldehyde | 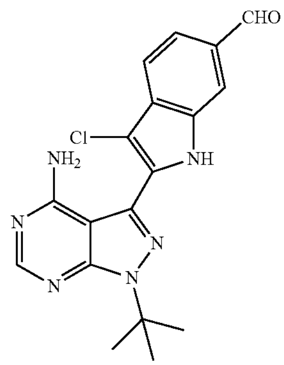 [SMILES: CC(C)(C)n1nc(-c2[nH]c3cc(C=O)ccc3c2Cl)c2c(N)ncnc21] | See Below |
| 15 | 2-(4-Amino-1-(tert-butyl)-1H-pyrazolo[3,4-d]pyrimidin-3-yl)-3-chloro-N,N-dimethyl-1H-indole-6-carboxamide | 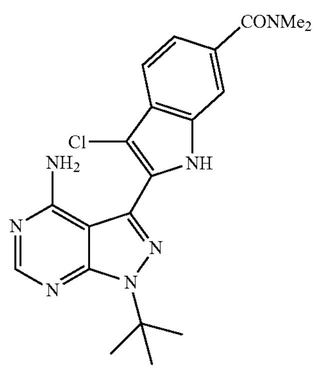 | See Below |
| 16 | 4-Chloro-3-iodo-1-isopropyl-1H-pyrazolo[4,3-c]pyridine | 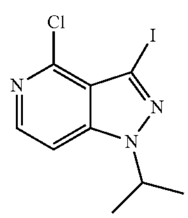 | See Below |
| 17 | 3-Iodo-1-isopropyl-1H-pyrazolo[4,3-c]pyridin-4-amine | 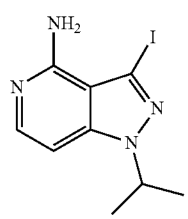 | See Below |
| 18 | 7-Chloro-3-iodo-1-isopropyl-1H-pyrazolo[4,3-c]pyridin-4-amine | 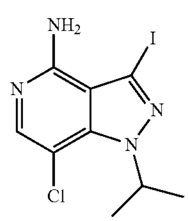 | See Below |
| 19 | (5-Chloro-1H-pyrrolo[2,3-b]pyridin-2-yl)boronic acid | 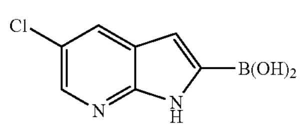 [SMILES: OB(O)c1cc2cc(Cl)cnc2[nH]1] | See Below |

TABLE A-continued

List of Intermediates and their method of synthesis

| Intermediate | Name | Structure | General Method |
|---|---|---|---|
| 20 | 3-(1-((2-(Trimethylsilyl)ethoxy)methyl)-1H-pyrrolo[2,3-b]pyridin-2-yl)-1H-pyrazolo[3,4-d]pyrimidin-4-amine | 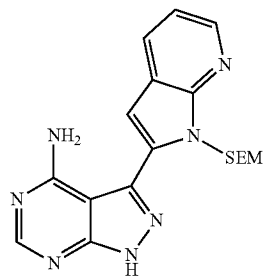 [SMILES: C[Si](C)(C)CCOCn1c(-c2n[nH]c3ncnc(N)c23)cc2cccnc21] | 3 |
| 21 | 3-(3-Chloro-1-((2-(trimethylsilyl)ethoxy)methyl)-1H-pyrrolo[2,3-b]pyridin-2-yl)-1H-pyrazolo[3,4-d]pyrimidin-4-amine | 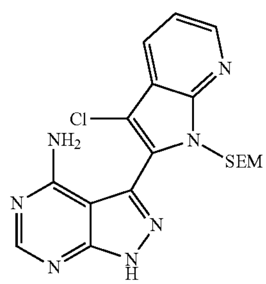 [SMILES: C[Si](C)(C)CCOCn1c(-c2n[nH]c3ncnc(N)c23)c(Cl)c2cccnc21] | 5 |
| 22 | 3-(3-Chloro-1-((2-(trimethylsilyl)ethoxy)methyl)-1H-pyrrolo[2,3-b]pyridin-2-yl)-1-(2,2-diethoxyethyl)-1H-pyrazolo[3,4-d]pyrimidin-4-amine | 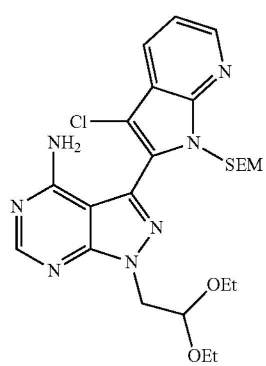 [SMILES: CCOC(Cn1nc(-c2c(Cl)c3cccnc3n2COCC[Si](C)(C)C)c2c(N)ncnc21)OCC] | See Below |
| 23 | 3-(3-Chloro-1H-pyrrolo[2,3-b]pyridin-2-yl)-1-(2,2-diethoxyethyl)-1H-pyrazolo[3,4-d]pyrimidin-4-amine | 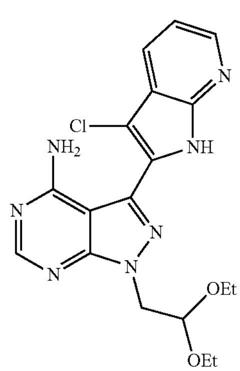 [SMILES: CCOC(Cn1nc(-c2[nH]c3ncccc3c2Cl)c2c(N)ncnc21)OCC] | See Below |

TABLE A-continued

List of Intermediates and their method of synthesis

| Intermediate | Name | Structure | General Method |
|---|---|---|---|
| 24 | 2-(4-Amino-3-(3-chloro-1H-pyrrolo[2,3-b]pyridin-2-yl)-1H-pyrazolo[3,4-d]pyrimidin-1-yl)acetaldehyde trifluoroacetate | 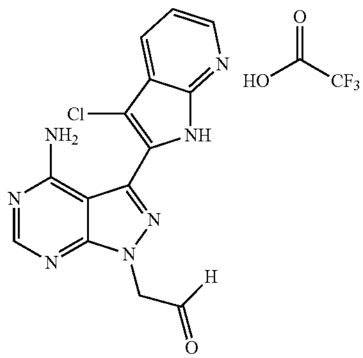 | See Below |
| 25 | (1-((2-(Trimethylsilyl)ethoxy)methyl)-1H-indol-2-yl)boronic acid | 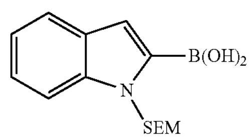 [SMILES: C[Si](C)(C)CCOCn1c(B(O)O)cc2ccccc21] | See Below |
| 26 | 3-(1-((2-(Trimethylsilyl)ethoxy)methyl)-1H-indol-2-yl)-1H-pyrazolo[3,4-d]pyrimidin-4-amine | 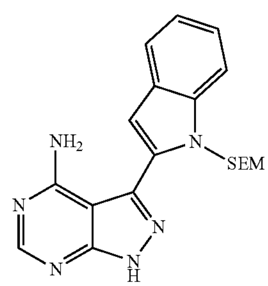 [SMILES: C[Si](C)(C)CCOCn1c(-c2n[nH]c3ncnc(N)c23)cc2ccccc21] | 3 |
| 27 | 3-(3-Chloro-1-((2-(trimethylsilyl)ethoxy)methyl)-1H-indol-2-yl)-1H-pyrazolo[3,4-d]pyrimidin-4-amine | 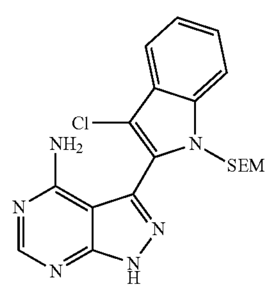 [SMILES: C[Si](C)(C)CCOCn1c(-c2n[nH]c3ncnc(N)c23)c(Cl)c2ccccc21] | 5 |
| 28 | tert-Butyl 6-cyano-2-tributylstannyl-pyrrolo[2,3-b]pyridine-1-carboxylate | 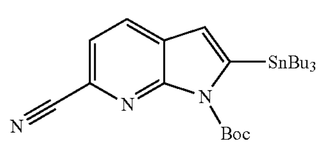 | See Below |

TABLE B

List of intermediates Prepared Using General Methods

| Intermediate | (%) | Adduct | m/z | $^1$H NMR (300 or 400 MHz, DMSO-$d_6$) δ |
|---|---|---|---|---|
| 4 | 48 | [M − H]⁻ | 266 and 268 | 8.20 (s, 1H), 7.87 (s, 1H), 6.97 (s, 1H), 5.24 (p, =J = 8.5 Hz, 1H), 2.60 (m, 2H), 2.47-2.28 (m, 2H), 1.85 (td, =J = 10.1, 5.6 Hz, 2H). |
| 5 | 20 | [M − H]⁻ | 409 and 411 | 8.20 (s, 1H), 6.83 (d, J = 7.9 Hz, 1H), 4.59-4.47 (m, 1H), 1.97-1.84 (m, 4H), 1.39 (s, 13H). CH obscured under HOD peak. |

TABLE B-continued

List of intermediates Prepared Using General Methods

| Intermediate | (%) | Adduct | m/z | $^1$H NMR (300 or 400 MHz, DMSO-$d_6$) δ |
|---|---|---|---|---|
| 6 | 41 | [M − H]$^-$ | 409 and 411 | ND |
| 12 | 31 | [M + H]$^+$ | 365 | *9.09 (br s, 1H), 8.40 (s, 1H), 8.22 (s, 1H), 7.86 (dd, =J = 1.40, 8.36 Hz, 1H), 7.69 (d, =J = 8.36 Hz, 1H), 6.93 (dd, =J = 0.85, 2.08 Hz, 1H), 5.78 (s, 2H), 3.96 (s, 3H), 1.86 (s, 9H). |
| 13 | 24 | [M − H]$^-$ | 397.1 | 12.28 (s, 1H), 8.27 (s, 1H), 8.11 (dd, J = 1.5, 0.7 Hz, 1H), 7.84-7.74 (m, 1H), 7.67 (d, J = 8.4 Hz, 1H), 7.01 (s, 2H), 3.89 (s, 3H), 1.79 (s, 9H). |
| 20 | 56 | [M + H]$^+$ | 382 | ND |
| 21 | 74 | [M + H]$^+$ | 416 | ND |
| 26 | 37 | [M + H]$^+$ | 381 | ND |
| 27 | 30 | [M + H]$^+$ | 415 | ND |

ND = no data
*$^1$H NMR (400 MHz, CDCl$_3$) δ

Synthesis of Other Intermediates 3-(4-Amino-3-bromo-1H-pyrazolo[3,4-d]pyrimidin-1-yl)cyclopentan-1-ol (Intermediate 7)

Step 1

To a solution of 3-bromo-1H-pyrazolo[3,4-d]pyrimidin-4-amine (2.00 g, 9.34 mmol) and 2-cyclopenten-1-one (1.53 g, 18.69 mmol) in THF (20 mL) was added HfCl$_4$ (111 mg, 0.3 mmol). The reaction was heated at reflux for 15 h, then cooled to room temperature and concentrated in vacuo. The residue was treated with water and extracted with EtOAc. The combined organic extracts were dried over Na$_2$SO$_4$, filtered and concentrated in vacuo to return the crude product which was purified by fcc to return 3-(4-amino-3-bromo-1H-pyrazolo[3,4-d]pyrimidin-1-yl)cyclopentan-1-one (750 mg, 27%) which was used without further purification.

Step 2

To a solution of 3-(4-amino-3-bromo-1H-pyrazolo[3,4-d]pyrimidin-1-yl)cyclopentan-1-one (750 mg, 2.5 mmol) in MeOH (30 mL) was added NaBH$_4$ (105 mg, 2.8 mmol). The reaction was stirred at room temperature for 2 h then concentrated in vacuo. The residue was treated with water and extracted with EtOAc. The combined organic extracts were dried over Na$_2$SO$_4$, filtered and concentrated in vacuo to return the title compound (750 mg, 100%). LCMS [M−H]$^-$ 298.6; $^1$H NMR (300 MHz, DMSO-$d_6$) δ 8.19 (s, 1H), 8.00 (s, 1H), 6.87 (s, 1H), 5.07 (p, =J=8.2 Hz, 1H), 4.86 (d, =J=4.8 Hz, 1H), 4.17 (h, =J=6.0 Hz, 1H), 2.36 (ddd, =J=13.0, 8.4, 6.5 Hz, 1H), 2.19-1.63 (m, 5H). Approx 9:1 ratio of isomers but unassigned whether cis or trans is the major isomer.

3-Bromo-1-methyl-1H-pyrazolo[3,4-d]pyrimidin-4-amine (Intermediate 8)

To a suspension of 3-bromo-1H-pyrazolo[3,4-d]pyrimidin-4-amine (1.75 g, 8.18 mmol), triphenylphosphine (4.29 g, 16.35 mmol) and MeOH (1 mL) in THF (50 mL) at 0° C. was added DIAD (3.22 mL, 16.35 mmol) dropwise at room temperature. The reaction was stirred for 5 days (for convenience) then concentrated in vacuo. The residue was dissolved in aq. HCl (1M, 50 mL) and washed with EtOAc (2×50 mL). The aqueous phase was basified with aq. NaOH (1M, 50 mL) then extracted with 20% MeOH:DCM (3×50 mL). The combined organics were filtered through a hydrophobic frit and then concentrated in vacuo to return the title compound (1.16 g, 62%) as a yellow powder which was used without further purification. LCMS [M+H]$^+$ 228.0 and 230.0; $^1$H NMR (300 MHz, DMSO-$d_6$) δ 8.22 (s, 1H), 3.86 (s, 3H).

1-(trans-4-Aminocyclohexyl)-3-bromo-1H-pyrazolo[3,4-d]pyrimidin-4-amine Trifluoroacetate (Intermediate 9)

To a solution of tert-butyl (trans-4-(4-amino-3-bromo-1H-pyrazolo[3,4-d]pyrimidin-1-yl)cyclohexyl)carbamate (850 mg, 2.07 mmol) in DCM (30 mL) was added trifluoroacetic acid (10.0 mL) dropwise. The mixture was stirred at 0° C. for 3 hours then concentrated in vacuo to return the title compound (900 mg, 98%) which was used without further purification.

N-(trans-4-(4-Amino-3-bromo-1H-pyrazolo[3,4-d]pyrimidin-1-yl)cyclohexyl) cyclopropanecarboxamide (Intermediate 10)

To a solution of 1-(trans-4-aminocyclohexyl)-3-bromo-1H-pyrazolo[3,4-d]pyrimidin-4-amine trifluoroacetate (900 mg, 2.03 mmol) in DCM (20 mL) was added Et$_3$N (1.41 mL, 10.15 mmol) and cyclopropanecarbonyl chloride (233 mg, 2.23 mmol). The reaction was stirred at room temperature for 3 hours then poured into water (50 mL) and extracted with EtOAc (4×60 mL). The combined organic phases were washed with brine (150 mL), dried and concentrated in vacuo to return the crude product which was purified by fcc to return the title product (513 mg, 67%).

3-Bromo-1-(trans-4-morpholinocyclohexyl)-1H-pyrazolo[3,4-d]pyrimidin-4-amine (Intermediate 11)

To a solution of 1-(trans-4-aminocyclohexyl)-3-bromo-1H-pyrazolo[3,4-d]pyrimidin-4-amine trifluoroacetate (715 mg, 1.33 mmol) in DMF (10 mL) was added K$_2$CO$_3$ (916 mg, 6.63 mmol). The mixture was heated to 80° C. and held for 0.5 h. Bis(2-bromoethyl) ether (923 mg, 3.98 mmol) was added dropwise and the mixture heated at 80° C. for 2 hours. The reaction mixture was cooled to room temperature and diluted with water (50 mL), stirred for 30 min then extracted with EtOAc (3×50 mL). The combined organic extracts were washed with brine (100 mL), filtered through a hydrophobic frit then concentrated in vacuo. The residue was purified by fcc (0-10% MeOH in DCM) to return the title compound (272 mg, 54%) as an off-white solid. LCMS [M−H]⁻ 379.1 and 381.1; ¹H NMR (300 MHz, DMSO-d₆) δ 8.20 (s, 1H), 7.96 (s, 1H), 6.88 (s, 1H), 4.58 (dt, J=10.5, 5.1 Hz, 1H), 3.57 (t, J=4.5 Hz, 4H), 2.32 (t, J=11.6 Hz, 1H), 1.94 (d, J=8.7 Hz, 6H), 1.48-1.31 (m, 2H). 4×H obscured under DMSO and HOD peaks.

2-(4-Amino-1-(tert-butyl)-1H-pyrazolo[3,4-d]pyrimidin-3-yl)-3-chloro-1H-indol-6-carbaldehyde (Intermediate 14)

To a solution of (2-(4-amino-1-(tert-butyl)-1H-pyrazolo[3,4-d]pyrimidin-3-yl)-3-chloro-1H-indol-6-yl)methanol (200 mg, 0.539 mmoL) in DCM (3 mL) was added a suspension of DMP (274 mg, 0.647 mmol) in DCM (3 mL) dropwise. The resulting mixture was stirred at room temperature for 45 min, then diluted with aq NaOH (1.0 M, 30 mL) and stirred for a further 15 min. EtOAc (30 mL) was added and the biphasic mixture separated. The organic layer was washed with water (30 mL), brine (30 mL), then dried and concentrated in vacuo to return the title compound as a brown solid (146 mg, 80% pure by HPLC, 74% yield); LCMS [M+H]⁺ 369. This material was used in the subsequent step without additional purification.

2-(4-Amino-1-(tert-butyl)-1H-pyrazolo[3,4-d]pyrimidin-3-yl)-3-chloro-N,N-dimethyl-1H-indole-6-carboxamide (Intermediate 15)

To a solution of methyl 2-(4-amino-1-tert-butyl-pyrazolo[3,4-d]pyrimidin-3-yl)-3-chloro-1H-indole-6-carboxylate (100 mg, 0.21 mmol) in THF (5 mL) was added dimethylamine solution (2M in THF, 0.43 mL, 0.8500 mmol) followed by AlMe₃ solution (2.0 M in hexane, 0.43 mL, 0.85 mmol) dropwise at room temperature. The mixture was heated to 45° C. for 5.5 h. Further dimethylamine solution (2M in THF, 0.43 mL, 0.8500 mmol) was added and the mixture heated for a further 0.5 h. The mixture was cooled to 0° C., then 20% aq. Rochelle's salt (10 mL) was added dropwise (caution: initial effervescence). The mixture was stirred for 15 min, then extracted with EtOAc (3×20 mL). The combined extracts were washed with water (25 mL) and brine (25 mL), filtered through a hydrophobic frit then concentrated in vacuo. The crude product was purified by fcc (0-10% MeOH in EtOAc). The crude product was further purified by preparative HPLC to return the title compound (57 mg, 65%) as a white powder. LCMS [M−H]⁻ 410.3; ¹H NMR (300 MHz, DMSO-d₆) δ 12.05 (s, 1H), 8.27 (s, 1H), 7.60 (dd, J=0.71, 8.21 Hz, 1H), 7.50 (d, J=0.67 Hz, 1H), 7.22 (dd, J=1.39, 8.21 Hz, 1H), 6.97 (br s, 2H), 3.00 (s, 6H), 1.79 (s, 9H).

4-Chloro-3-iodo-1-isopropyl-1H-pyrazolo[4,3-c]pyridine (Intermediate 16)

To a suspension of 4-chloro-3-iodo-1H-pyrazolo[4,3-c]pyridine (859 mg, 2.92 mmol) and K₂CO₃ (605 mg, 4.38 mmol) in acetonitrile (45 mL) was added 2-iodopropane (0.292 mL, 2.92 mmol) and the resulting mixture heated at 60° C. for 18 h. After cooling to room temperature, the mixture was partitioned between sat aq NH₄Cl (20 mL) and EtOAc (20 mL). The organic layer was separated and retained and the aq phase was extracted with further EtOAc (2×20 mL). The combined organic extracts were washed with brine (50 mL), dried and concentrated in vacuo. The residue obtained was purified by fcc (0-100% EtOAc in isohexane) to return the title compound (478 mg, 51%) as an off-white solid. LCMS [M+H]+ 322; ¹H NMR (400 MHz, CDCl₃) δ 8.15 (d, =J=6.0 Hz, 1H), 7.31 (d, =J=6.0 Hz, 1H), 4.78 (hept, =J=6.7 Hz, 1H), 1.60 (d, =J=6.7 Hz, 6H).

3-Iodo-1-isopropyl-1H-pyrazolo[4,3-c]pyridin-4-amine (Intermediate 17)

To a solution of 4-chloro-3-iodo-1-isopropyl-1H-pyrazolo[4,3-c]pyridine (4.56 g, 13.9 mmol) in 1,4-dioxane (30 mL) was added NH₄OH (28% NH₃, 205 mL) and the resulting suspension was heated in a sealed 500 mL pressure vessel at 140° C. for 19 h. Further NH₄OH (28% NH₃, 100 mL) was added and the mixture heated at 120° C. for 18 h. After cooling to room temperature the reaction was concentrated in vacuo and the resulting solid was slurried with EtOAc, filtered, washed with further EtOAc (20 mL) and dried to return the title compound (4.10 g, 98%) as an yellow solid. LCMS [M+H]⁺ 302; ¹H NMR (400 MHz, DMSO-d₆) δ 7.71 (d, =J=6.3 Hz, 1H), 7.35 (br, 2H), 6.99 (d, =J=6.3 Hz, 1H), 4.84 (hept, =J=6.6 Hz, 1H), 1.42 (d, =J=6.6 Hz, 6H).

7-Chloro-3-iodo-1-isopropyl-1H-pyrazolo[4,3-c]pyridin-4-amine (Intermediate 18)

To 3-iodo-1-isopropyl-pyrazolo[4,3-c]pyridin-4-amine (200 mg, 0.66 mmol) in MeCN (5 mL) was added NCS (89 mg, 0.66 mmol) and the resulting solution was stirred at 70° C. for 3 h. The solvent was concentrated in vacuo and the residue obtained purified by fcc (0-20% MeOH in DCM) to return the title compound (80 mg, 36%) as a brown solid. LCMS [M+H]⁺ 336; ¹H NMR (400 MHz, DMSO-d₆) δ 7.72 (s, 1H), 6.53 (br, 2H), 5.46 (hept, =J=6.5 Hz, 1H), 1.46 (d, =J=6.5 Hz, 6H).

(5-Chloro-1H-pyrrolo[2,3-b]pyridin-2-yl)boronic Acid (Intermediate 19)

To a solution of tert-butyl 5-chloropyrrolo[2,3-b]pyridine-1-carboxylate (200 mg, 0.784 mmol) and triisopropyl borate (240 μL, 0.784 mmol) in THF (5 mL) at 0° C. was added LDA (1.0 M, 1.0 mL). The resulting mixture was maintained at 0° C. for 1.5 h then quenched through the addition of AcOH:water (1:2, 3 mL) and allowed to warm to room temperature over 30 min. The mixture was neutralised through the addition of sat. aq NaHCO₃ and diluted with EtOAc (20 mL). The organic layer was separated and retained and the aq phase was extracted with further EtOAc (2×20 mL). The combined organic extracts were washed with water (2×10 mL), brine (2×10 mL), dried and concentrated in vacuo to the title compound (184 mg) as a brown solid. This material was used in subsequent steps without purification or analysis.

3-(3-Chloro-1-((2-(trimethylsilyl)ethoxy)methyl)-1H-pyrrolo[2,3-b]pyridin-2-yl)-1-(2,2-diethoxyethyl)-1H-pyrazolo[3,4-d]pyrimidin-4-amine (Intermediate 22)

To a solution of 3-(3-chloro-1-((2-(trimethylsilyl)ethoxy)methyl)-1H-pyrrolo[2,3-b]pyridin-2-yl)-1H-pyrazolo[3,4-d]pyrimidin-4-amine (200 mg, 0.48 mmol) and K₂CO₃ (268 mg, 1.94 mmol) in DMF (15 mL) was added 2-bromo-1,1-diethoxy-ethane (73.9 μL, 0.529 mmol) and the resulting mixture heated at 80° C. for 18 h. The crude mixture was cooled to room temperature and partitioned between EtOAc (50 mL) and brine (50 mL). The organic layer was separated, washed with further brine (3×50 mL), dried and concentrated in vacuo. The crude product was purified by fcc (0-100% EtOAc in DCM) to return the title compound (143 mg, 55% yield) as a white solid. LCMS [M+H]⁺ 532; $^1$H NMR (400 MHz, DMSO-$d_6$) δ 8.48 (dd, J=4.7, 1.6 Hz, 1H), 8.29 (s, 1H), 8.08 (dd, J=7.9, 1.6 Hz, 1H), 7.35 (dd, J=7.9, 4.7 Hz, 1H), 5.76 (d, J=11.1 Hz, 1H), 5.65 (d, J=11.1 Hz, 1H), 5.03 (t, J=5.7 Hz, 1H), 4.53-4.43 (m, 2H), 3.72-3.62 (m, 2H), 3.49-3.41 (m, 2H), 3.32-3.25 (m, 1H), 3.17-3.11 (m, 1H), 1.03 (t, J=7.0 Hz, 6H), 0.68-0.55 (m, 2H), −0.25 (s, 9H). NH$_2$ signals not observed.

3-(3-Chloro-1H-pyrrolo[2,3-b]pyridin-2-yl)-1-(2,2-diethoxyethyl)-1H-pyrazolo[3,4-d]pyrimidin-4-amine (Intermediate 23)

To a solution of 3-(3-chloro-1-((2-(trimethylsilyl)ethoxy)methyl)-1H-pyrrolo[2,3-b]pyridin-2-yl)-1-(2,2-diethoxyethyl)-1H-pyrazolo[3,4-d]pyrimidin-4-amine (130 mg, 0.244 mmol) in EtOH (5 mL) was added conc. HCl (0.23 mL) and the resulting mixture heated at 50° C. for 73 h. Na$_2$CO$_3$ (500 mg, 4.76 mmol) was added, the resulting mixture was filtered and the filtrate concentrated in vacuo. The solid obtained was triturated with DCM (15 mL), filtered and dried to return the title compound (77 mg, 76% pure by HPLC, 79% yield) as a yellow solid. LCMS [M+H]⁺ 402. This material was used in the subsequent step without additional purification.

2-(4-Amino-3-(3-chloro-1H-pyrrolo[2,3-b]pyridin-2-yl)-1H-pyrazolo[3,4-d]pyrimidin-1-yl)acetaldehyde Trifluoroacetate (Intermediate 24)

To a suspension of 3-(3-chloro-1H-pyrrolo[2,3-b]pyridin-2-yl)-1-(2,2-diethoxyethyl)-1H-pyrazolo[3,4-d]pyrimidin-4-amine (77 mg, 0.19 mmol) in water (1.5 mL) was added 2,2,2-trifluoroacetic acid (1.5 mL, 0.19 mmol) and the resulting mixture was heated at 100° C. in a sealed tube in the microwave for 1 h. The solvent was concentrated in vacuo to return the title compound (180 mg, 88% yield) as a yellow oil. LCMS [M+H$_3$O]⁺ 346. This material was used in the subsequent step without additional purification.

(1-((2-(Trimethylsilyl)ethoxy)methyl)-1H-indol-2-yl)boronic Acid (Intermediate 25)

To a solution of 2-(indol-1-ylmethoxy)ethyl-trimethylsilane (3.60 g, 14.3 mmol) in THF (30 mL) at −78° C. was added tert-butyl lithium (1.7 M in pentane, 12.0 mL) dropwise. The resulting mixture was maintained at −78° C. for 5 min, warmed to room temperature over 30 min then re-cooled −78° C. and treated with triisopropyl borate (6.00 mL, 25.8 mmol). The mixture that formed was maintained at −78° C. for 10 min, then warmed to room temperature and stirred for 2.5 h. Sat aq NH$_4$Cl (150 mL) was added carefully, followed by EtOAc (100 mL) and the biphasic mixture separated. The organic layer was separated and retained and the aq phase was extracted with further EtOAc (2×100 mL). The combined organic extracts were washed with brine (100 mL), dried and concentrated in vacuo to return the title compound (4.10 g, 50% pure by HPLC) as a red gum. LCMS [M+H]⁺ 292. This material was used in the subsequent step without additional purification.

tert-Butyl 6-cyano-2-tributylstannyl-pyrrolo[2,3-b]pyridine-1-carboxylate (Intermediate 28)

To a solution of tert-butyl 6-cyanopyrrolo[2,3-b]pyridine-1-carboxylate (1.25 g, 5.14 mmol) and tributyl(chloro)stannane (1.70 mL, 6.27 mmol) in THF (10 mL) at 0° C. was added LDA (2.0 M in THF, 3.7 mL) dropwise over 10 min. The resulting mixture was stirred at 0° C. for 1 h, then warmed to room temperature and stirred for 15 h. Water (50 mL) and MTBE (50 mL) were added and the biphasic mixture separated. The organic extracts were then washed with aq NaF (10 wt %, 50 mL), brine (50 mL), dried and concentrated in vacuo. The crude product was purified by fcc (0-25% DCM in isohexane) to return the title compound (1.17 g, 90% pure by $^1$H NMR, 43% yield) as a colourless oil. $^1$H NMR (400 MHz, CDCl$_3$) δ 7.85 (d, J=8.0 Hz, 1H), 7.52 (d, J=8.0 Hz, 1H), 6.72 (s, 1H), 1.72 (s, 9H), 1.57-1.46 (m, 6H), 1.37-1.26 (m, 6H), 1.21-1.02 (m, 6H), 0.89 (t, J=7.3 Hz, 9H).

Final Compounds

TABLE C

| | List of Examples and their method of synthesis | | |
|---|---|---|---|
| | Example Name | Structure | General Method |
| 1 | 1-(tert-Butyl)-3-(1H-indol-2-yl)-1H-pyrazolo[3,4-d]pyrimidin-4-amine | 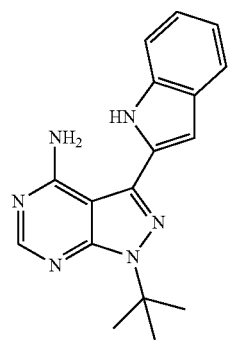 [SMILES: CC(C)(C)n1nc(-c2cc3ccccc3[nH]2)c2c(N)ncnc21] | 3 |

TABLE C-continued

List of Examples and their method of synthesis

| Example | Name | Structure | General Method |
|---------|------|-----------|----------------|
| 2 | 3-(1H-Indol-2-yl)-1-(1-methylsulfonyl-4-piperidyl)pyrazolo[3,4-d]pyrimidin-4-amine | 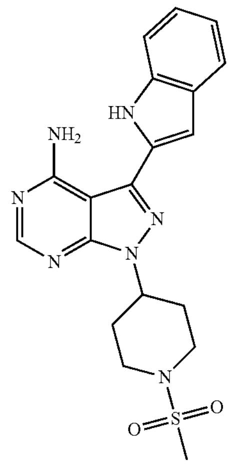 [SMILES: CS(=O)(=O)N1CCC(n2nc(-c3cc4ccccc4[nH]3)c3c(N)ncnc32)CC1] | 3 |
| 3 | 1-tert-Butyl-3-(3-chloro-1H-indol-2-yl)pyrazolo[3,4-d]pyrimidin-4-amine | 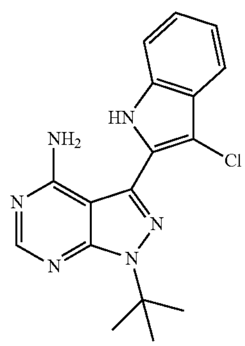 [SMILES: CC(C)(C)n1nc(-c2[nH]c3ccccc3c2Cl)c2c(N)ncnc21] | 4 |
| 4 | 3-(3-Chloro-1H-indol-2-yl)-1-(1-methylsulfonyl-4-piperidyl)pyrazolo[3,4-d]pyrimidin-4-amine | 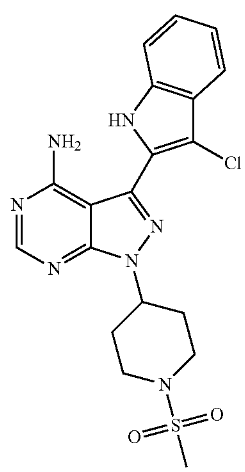 [SMILES: CS(=O)(=O)N1CCC(n2nc(-c3[nH]c4ccccc4c3Cl)c3c(N)ncnc32)CC1] | 4 |

TABLE C-continued
List of Examples and their method of synthesis
| Example | Name | Structure | General Method |
|---|---|---|---|
| 5 | N-(trans-4-(4-Amino-3-(1H-indol-2-yl)-1H-pyrazolo[3,4-d]pyrimidin-1-yl)cyclohexyl)cyclopropanecarboxamide | 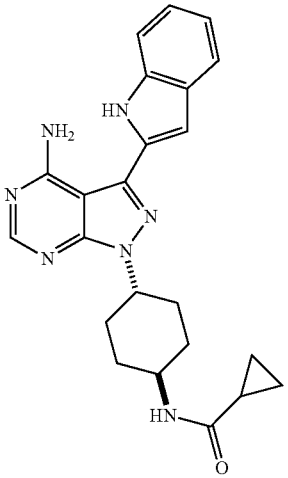 | 3 |
| 6 | 3-(1H-Indol-2-yl)-1-(trans-4-morpholinocyclohexyl)-1H-pyrazolo[3,4-d]pyrimidin-4-amine | 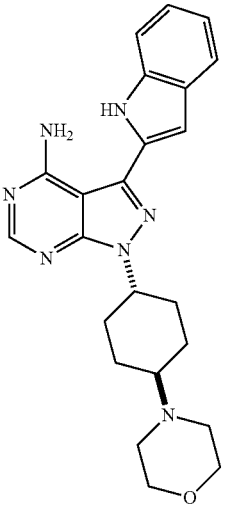 | 3 |
| 7 | 3-(3-Chloro-1H-idol-2-yl)-1-(trans-4-morpholinocyclohexyl)-1H-pyrazolo[3,4-d]pyrimidin-4-amine | 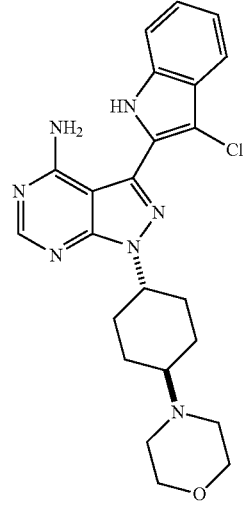 | 5 |

TABLE C-continued

List of Examples and their method of synthesis

| Example | Name | Structure | General Method |
|---|---|---|---|
| 8 | N-[4-[trans-4-Amino-3-(3-chloro-1H-indol-2-yl)pyrazolo[3,4-d]pyrimidin-1-yl]cyclohexyl]cyclopropanecarboxamide | 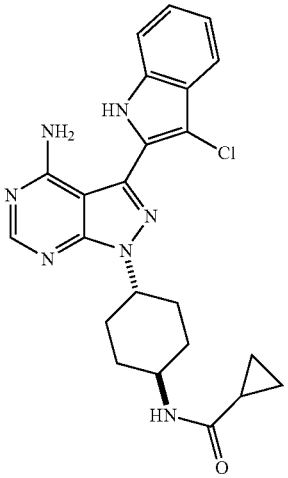 | 5 |
| 9 | 1-tert-Butyl-3-{1H-pyrrolo[2,3-b]pyridin-2-yl}-1H-pyrazolo[3,4-d]pyrimidin-4-amine | 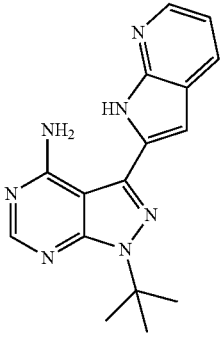 [SMILES: CC(C)(C)n1nc(-c2cc3cccnc3[nH]2)c2c(N)ncnc21] | 3 |
| 10 | 1-tert-Butyl-3-{3-chloro-1H-pyrrolo[2,3-b]pyridin-2-yl}-1H-pyrazolo[3,4-d]pyrimidin-4-amine | 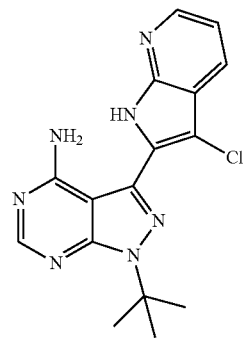 [SMILES: CC(C)(C)n1nc(-c2[nH]c3ncccc3c2Cl)c2c(N)ncnc21] | 5 |
| 11 | 3-(1H-Indol-2-yl)-1-(propan-2-yl)-1H-pyrazolo[4,3-c]pyridin-4-amine | 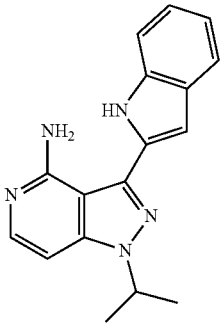 | 3 |

TABLE C-continued
List of Examples and their method of synthesis
| Example | Name | Structure | General Method |
|---|---|---|---|
| 12 | 3-(3-Chloro-1H-indol-2-yl)-1-(propan-2-yl)-1H-pyrazolo[4,3-c]pyridin-4-amine | 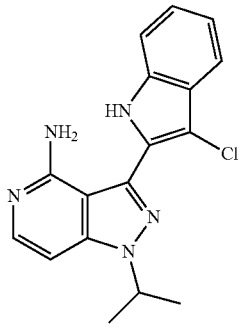 [SMILES: CC(C)n1nc(-c2[nH]c3ccccc3c2Cl)c2c(N)nccc21] | 5 |
| 13 | 5-(1H-Indol-2-yl)-7-(propan-2-yl)pyrrolo[2,1-f][1,2,4]triazin-4-amine | 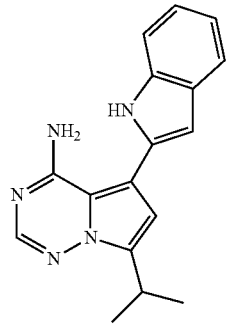 [SMILES: CC(C)c1cc(-c2cc3ccccc3[nH]2)c2c(N)ncnn12] | 3 |
| 14 | 5-(3-Chloro-1H-indol-2-yl)-7-(propan-2-yl)pyrrolo[2,1-f][1,2,4]triazin-4-amine | 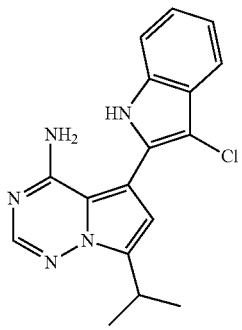 [SMILES: CC(C)c1cc(-c2[nH]c3ccccc3c2Cl)c2c(N)ncnn12] | 5 |
| 15 | 3-(6-Bromo-1H-indol-2-yl)-1-isopropyl-pyrazolo[3,4-d]pyrimidin-4-amine | 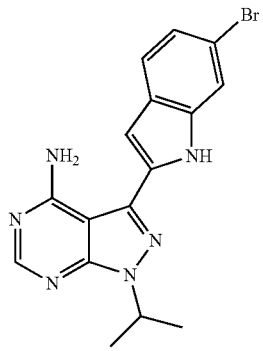 [SMILES: CC(C)n1nc(-c2cc3ccc(Br)cc3[nH]2)c2c(N)ncnc21] | 3 |

TABLE C-continued

List of Examples and their method of synthesis

| Example | Name | Structure | General Method |
|---|---|---|---|
| 16 | 3-(6-Bromo-3-chloro-1H-indol-2-yl)-1-isopropyl-pyrazolo[3,4-d]pyrimidin-4-amine | 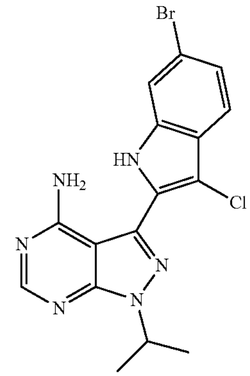 [SMILES: CC(C)n1nc(-c2[nH]c3cc(Br)ccc3c2Cl)c2c(N)ncnc21] | 5 |
| 17 | 2-(4-Amino-1-(tert-butyl)-1H-pyrazolo[3,4-d]pyrimidin-3-yl)-1H-indole-6-carbonitrile | 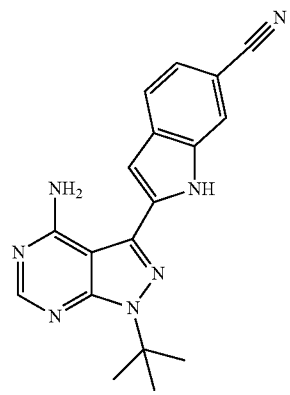 [SMILES: CC(C)(C)n1nc(-c2cc3ccc(C#N)cc3[nH]2)c2c(N)ncnc21] | 3 |
| 18 | 2-(4-Amino-1-(tert-butyl)-1H-pyrazolo[3,4-d]pyrimidin-3-yl)-3-chloro-1H-indole-6-carbonitrile | 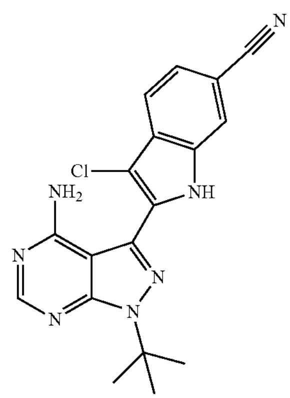 [SMILES: CC(C)(C)n1nc(-c2[nH]c3cc(C#N)ccc3c2Cl)c2c(N)ncnc21] | 5 |
| 19 | (2-(4-Amino-1-(tert-butyl)-1H-pyrazolo[3,4-d]pyrimidin-3-yl)-3-chloro-1H-indol-6-yl)methanol | 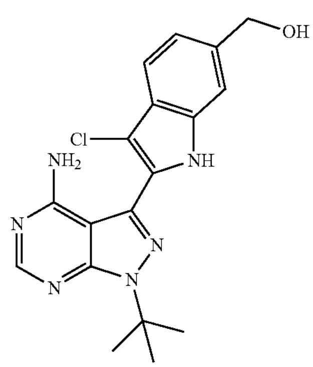 [SMILES: CC(C)(C)n1nc(-c2[nH]c3cc(CO)ccc3c2Cl)c2c(N)ncnc21] | See Below |

TABLE C-continued

List of Examples and their method of synthesis

| Example | Name | Structure | General Method |
|---|---|---|---|
| 20 | 1-(tert-Butyl)-3-(6-chloro-1H-indol-2-yl)-1H-pyrazolo[3,4-d]pyrimidin-4-amine | 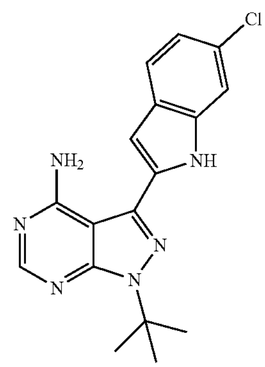 [SMILES: CC(C)(C)n1nc(-c2cc3ccc(Cl)cc3[nH]2)c2c(N)ncnc21] | 3 |
| 21 | 7-Isopropyl-5-(1H-pyrrolo[2,3-b]pyridin-2-yl)pyrrolo[2,3-d]pyrimidin-4-amine | 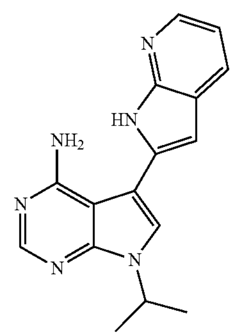 [SMILES: CC(C)n1cc(-c2cc3cccnc3[nH]2)c2c(N)ncnc21] | 3 |
| 22 | 1-(1-Methanesulfonylpiperidin-4-yl)-3-{1H-pyrrolo[2,3-b]pyridin-2-yl}-1H-pyrazolo[3,4-d]pyrimidin-4-amine | 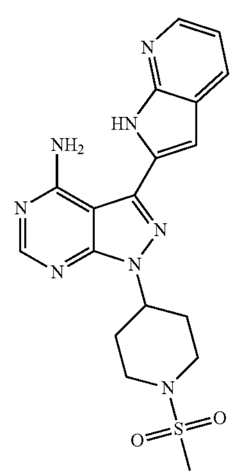 [SMILES: CS(=O)(=O)N1CCC(n2nc(-c3cc4cccnc4[nH]3)c3c(N)ncnc32)CC1] | 3 |

TABLE C-continued

List of Examples and their method of synthesis

| Example | Name | Structure | General Method |
|---|---|---|---|
| 23 | 3-{3-Chloro-1H-pyrrolo[2,3-b]pyridin-2-yl}-1-(1-methanesulfonylpiperidin-4-yl)-1H-pyrazolo[3,4-d]pyrimidin-4-amine | 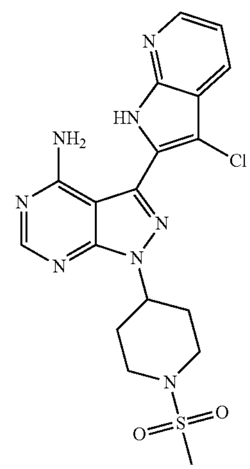 [SMILES: CS(=O)(=O)N1CCC(n2nc(-c3[nH]c4ncccc4c3Cl)c3c(N)ncnc32)CC1] | 5 |
| 24 | 1-tert-Butyl-3-(3,6-dichloro-1H-indol-2-yl)-1H-pyrazolo[3,4-d]pyrimidin-4-amine | 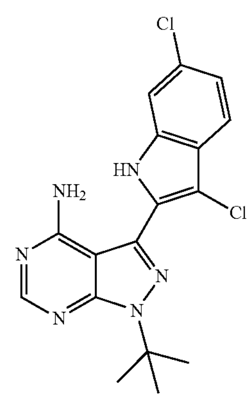 [SMILES: CC(C)(C)n1nc(-c2[nH]c3cc(Cl)ccc3c2Cl)c2c(N)ncnc21] | 5 |
| 25 | 1-tert-Butyl-3-{3-chloro-6-[(methylamino)methyl]-1H-indol-2-yl}-1H-pyrazolo[3,4-d]pyrimidin-4-amine | 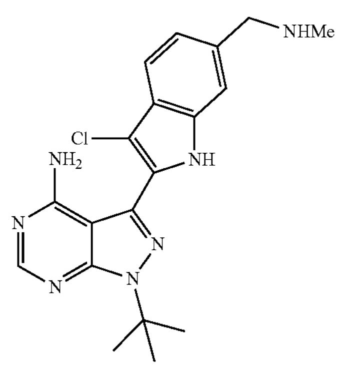 [SMILES: CNCc1ccc2c(Cl)c(-c3nn(C(C)(C)C)c4ncnc(N)c34)[nH]c2c1] | See Below |

TABLE C-continued

List of Examples and their method of synthesis

| Example | Name | Structure | General Method |
|---|---|---|---|
| 26 | 1-tert-Butyl-3-[3-chloro-6-(methoxymethyl)-1H-indol-2-yl]-1H-pyrazolo[3,4-d]pyrimidin-4-amine | 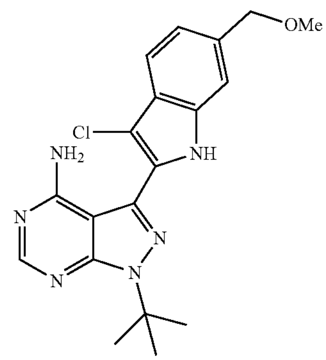 [SMILES: COCc1ccc2c(Cl)c(-c3nn(C(C)(C)C)c4ncnc(N)c34)[nH]c2c1] | See Below |
| 27 | tert-Butyl N-[cis-4-(4-amino-3-{1H-pyrrolo[2,3-b]pyridin-2-yl}-1H-pyrazolo[3,4-d]pyrimidin-1-yl)cyclohexyl]carbamate | 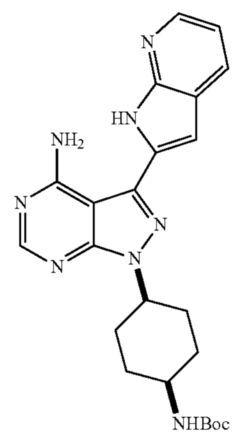 | 3 |
| 28 | tert-Butyl (trans-4-(4-amino-3-(1H-pyrrolo[2,3-b]pyridin-2-yl)-1H-pyrazolo[3,4-d]pyrimidin-1-yl)cyclohexyl)carbamate | 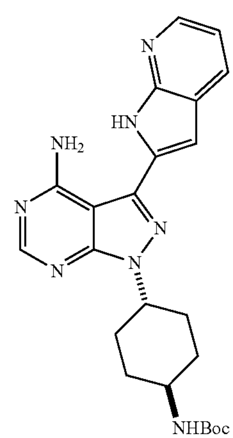 | 3 |

TABLE C-continued

List of Examples and their method of synthesis

| Example | Name | Structure | General Method |
|---|---|---|---|
| 29 | tert-Butyl N-[cis-4-(4-amino-3-{3-chloro-1H-pyrrolo[2,3-b]pyridin-2-yl}-1H-pyrazolo[3,4-d]pyrimidin-1-yl)cyclohexyl]carbamate | 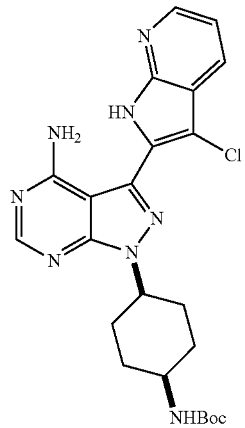 | 5 |
| 30 | tert-Butyl N-[trans-4-(4-amino-3-{3-chloro-1H-pyrrolo[2,3-b]pyridin-2-yl}-1H-pyrazolo[3,4-d]pyrimidin-1-yl)cyclohexyl]carbamate | 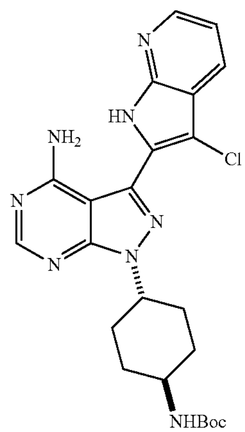 | 5 |
| 31 | 1-Methyl-3-{1H-pyrrolo[2,3-b]pyridin-2-yl}-1H-pyrazolo[3,4-d]pyrimidin-4-amine | 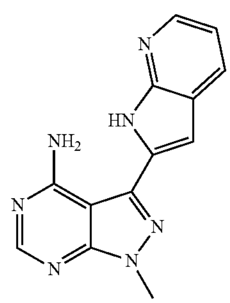 [SMILES: Cn1nc(-c2cc3cccnc3[nH]2)c2c(N)ncnc21] | 3 |
| 32 | 1-Isopropyl-3-(1H-pyrrolo[2,3-b]pyridin-2-yl)-1H-pyrazolo[4,3-c]pyridin-4-amine | 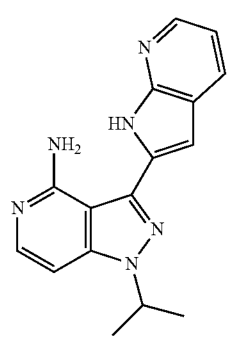 [SMILES: CC(C)n1nc(-c2cc3cccnc3[nH]2)c2c(N)nccc21] | 3 |

TABLE C-continued

List of Examples and their method of synthesis

| Example | Name | Structure | General Method |
|---|---|---|---|
| 33 | 3-(3-Chloro-1H-pyrrolo[2,3-b]pyridin-2-yl)-1-isopropyl-1H-pyrazolo[4,3-c]pyridin-4-amine | 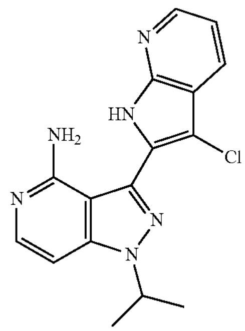 [SMILES: CC(C)n1nc(-c2[nH]c3ncccc3c2Cl)c2c(N)nccc21] | 3 |
| 34 | 3-(3-bromo-1H-pyrrolo[2,3-b]pyridin-2-yl)-1-(tert-butyl)-1H-pyrazolo[3,4-d]pyrimidin-4-amine | 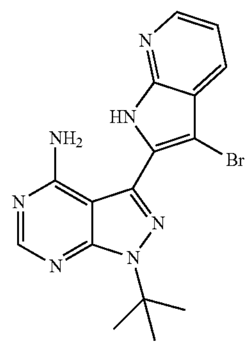 [SMILES: CC(C)(C)n1nc(-c2[nH]c3ncccc3c2Br)c2c(N)ncnc21] | See Below |
| 35 | 3-(6-(Aminomethyl)-3-chloro-1H-indol-2-yl)-1-(tert-butyl)-1H-pyrazolo[3,4-d]pyrimidin-4-amine | 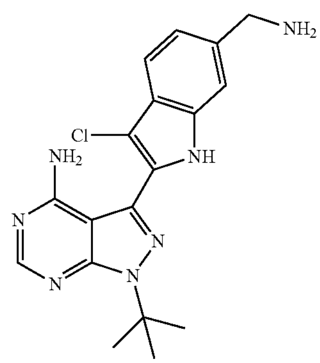 [SMILES: CC(C)(C)n1nc(-c2[nH]c3cc(CN)ccc3c2Cl)c2c(N)ncnc21] | See Below |
| 36 | N-(trans-4-(4-Amino-3-(1H-pyrrolo[2,3-b]pyridin-2-yl)-1H-pyrazolo[3,4-d]pyrimidin-1-yl)cyclohexyl)cyclopropanecarboxamide | 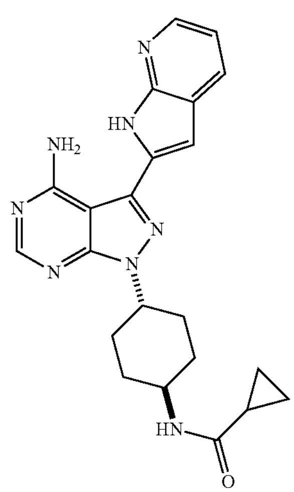 | 3 |

TABLE C-continued

List of Examples and their method of synthesis

| Example | Name | Structure | General Method |
|---|---|---|---|
| 37 | 1-Isopropyl-3-(1H-pyrrolo[2,3-b]pyridin-2-yl)pyrazolo[3,4-d]pyrimidin-4-amine | 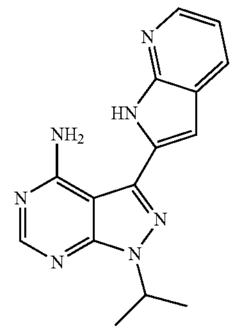 [SMILES: CC(C)n1nc(-c2cc3cccnc3[nH]2)c2c(N)ncnc21] | 3 |
| 38 | 1-(cis-4-Aminocyclohexyl)-3-(3-chloro-1H-pyrrolo[2,3-b]pyridin-2-yl)-1H-pyrazolo[3,4-d]pyrimidin-4-amine dihydrochloride | 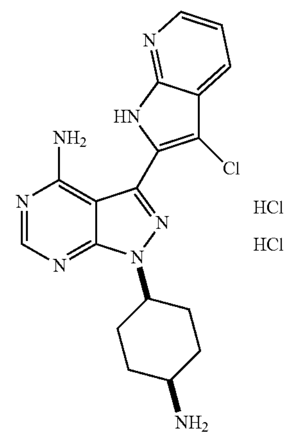 | See below |
| 39 | 1-Cyclohexyl-3-(1H-indol-2-yl)pyrazolo[3,4-d]pyrimidin-4-amine | 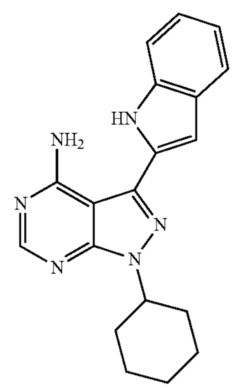 [SMILES: Nc1ncnc2c1c(-c1cc3ccccc3[nH]1)nn2C1CCCCC1] | 3 |
| 40 | 3-[4-Amino-3-(1H-pyrrolo[2,3-b]pyridin-2-yl)pyrazolo[3,4-d]pyrimidin-1-yl]cyclopentanol | 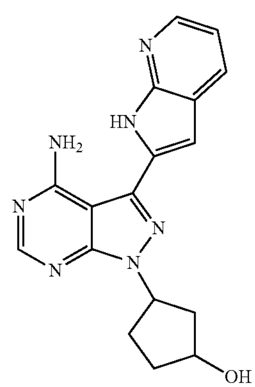 [SMILES: Nc1ncnc2c1c(-c1cc3cccnc3[nH]1)nn2C1CCC(O)C1] | 3 |

TABLE C-continued

List of Examples and their method of synthesis

| Example | Name | Structure | General Method |
|---|---|---|---|
| 41 | 1-Cyclohexyl-3-(1H-pyrrolo[2,3-b]pyridin-2-yl)pyrazolo[3,4-d]pyrimidin-4-amine | 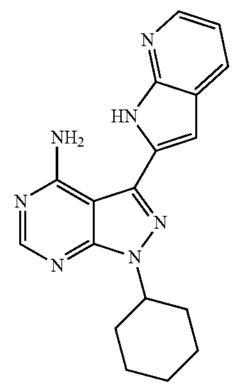 [SMILES: Nc1ncnc2c1c(-c1cc3cccnc3[nH]1)nn2C1CCCCC1] | 3 |
| 42 | 1-Cyclobutyl-3-(1H-pyrrolo[2,3-b]pyridin-2-yl)pyrazolo[3,4-d]pyrimidin-4-amine | 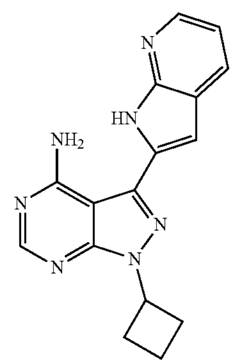 [SMILES: Nc1ncnc2c1c(-c1cc3cccnc3[nH]1)nn2C1CCC1] | 3 |
| 43 | 1-Ethyl-3-(1H-pyrrolo[2,3-b]pyridin-2-yl)pyrazolo[3,4-d]pyrimidin-4-amine | 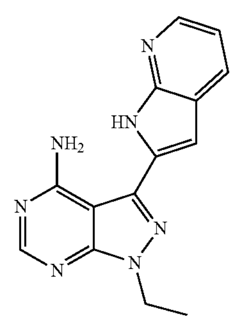 [SMILES: CCn1nc(-c2cc3cccnc3[nH]2)c2c(N)ncnc21] | 3 |
| 44 | 3-(1H-Indol-2-yl)-1-isopropyl-pyrazolo[3,4-d]pyrimidin-4-amine | 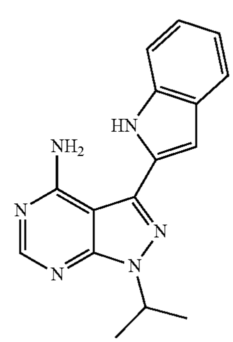 [SMILES: CC(C)n1nc(-c2cc3ccccc3[nH]2)c2c(N)ncnc21] | 3 |

TABLE C-continued

List of Examples and their method of synthesis

| Example | Name | Structure | General Method |
|---|---|---|---|
| 45 | 5-(3-Chloro-1H-pyrrolo[2,3-b]pyridin-2-yl)-7-isopropyl-pyrrolo[2,3-d]pyrimidin-4-amine | 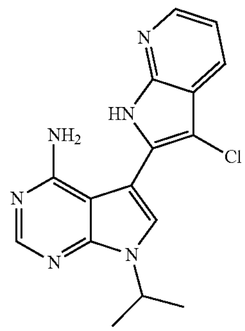 [SMILES: CC(C)n1cc(-c2[nH]c3ncccc3c2Cl)c2c(N)ncnc21] | 5 |
| 46 | 3-(3-Chloro-1H-pyrrolo[2,3-b]pyridin-2-yl)-1-ethyl-pyrazolo[3,4-d]pyrimidin-4-amine | 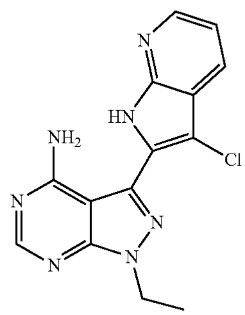 [SMILES: CCn1nc(-c2[nH]c3ncccc3c2Cl)c2c(N)ncnc21] | 5 |
| 47 | 5-(1H-Indol-2-yl)-7-isopropyl-pyrrolo[2,3-d]pyrimidin-4-amine | 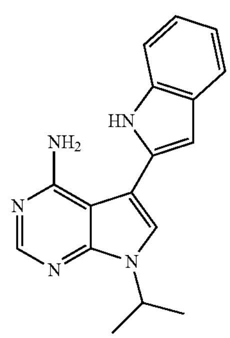 [SMILES: CC(C)n1cc(-c2cc3ccccc3[nH]2)c2c(N)ncnc21] | 3 |
| 48 | 5-(3-Chloro-1H-indol-2-yl)-7-isopropyl-pyrrolo[2,3-d]pyrimidin-4-amine | 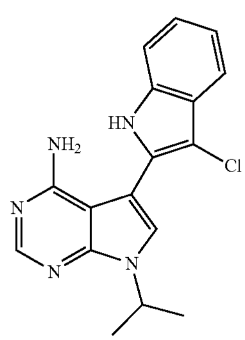 [SMILES: CC(C)n1cc(-c2[nH]c3ccccc3c2Cl)c2c(N)ncnc21] | 5 |

TABLE C-continued

List of Examples and their method of synthesis

| Example | Name | Structure | General Method |
|---|---|---|---|
| 49 | 3-(3-Bromo-1H-indol-2-yl)-1-(tert-butyl)-1H-pyrazolo[3,4-d]pyrimidin-4-amine | 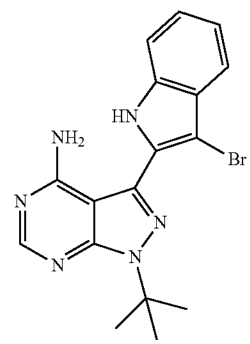 [SMILES: CC(C)(C)n1nc(-c2[nH]c3ccccc3c2Br)c2c(N)ncnc21] | See Below |
| 50 | 1-(tert-Butyl)-3-(5-chloro-1H-pyrrolo[2,3-b]pyridin-2-yl)-1H-pyrazolo[3,4-d]pyrimidin-4-amine | 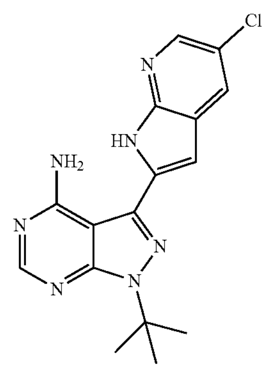 [SMILES: CC(C)(C)n1nc(-c2cc3cc(Cl)cnc3[nH]2)c2c(N)ncnc21] | 3 |
| 51 | 1-(tert-Butyl)-3-(3,5-dichloro-1H-pyrrolo[2,3-b]pyridin-2-yl)-1H-pyrazolo[3,4-d]pyrimidin-4-amine | 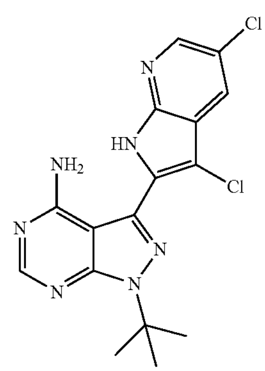 [SMILES: CC(C)(C)n1nc(-c2[nH]c3ncc(Cl)cc3c2Cl)c2c(N)ncnc21] | 5 |
| 52 | 2-(2-(4-Amino-1-(tert-butyl)-1H-pyrazolo[3,4-d]pyrimidin-3-yl)-3-chloro-1H-indol-6-yl)propan-2-ol | 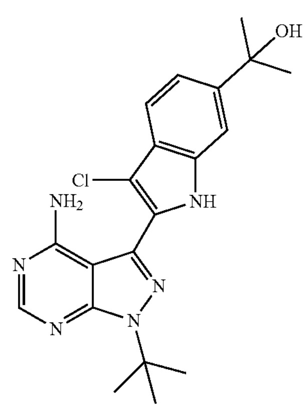 [SMILES: CC(C)(O)c1ccc2c(Cl)c(-c3nn(C(C)(C)C)c4ncnc(N)c34)[nH]c2c1] | See Below |

TABLE C-continued

List of Examples and their method of synthesis

| Example | Name | Structure | General Method |
|---|---|---|---|
| 53 | 1-tert-Butyl-3-(3,4-dichloro-1H-indol-2-yl)pyrazolo[3,4-d]pyrimidin-4-amine | 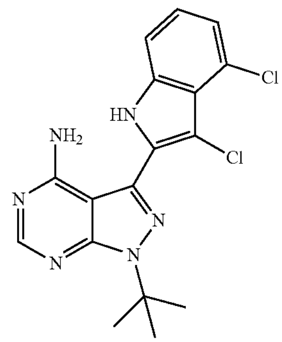 [SMILES: CC(C)(C)n1nc(-c2[nH]c3cccc(Cl)c3c2Cl)c2c(N)ncnc21] | 5 |
| 54 | 2-(4-Amino-1-tert-butyl-pyrazolo[3,4-d]pyrimidin-3-yl)-1H-indole-5-carbonitrile | 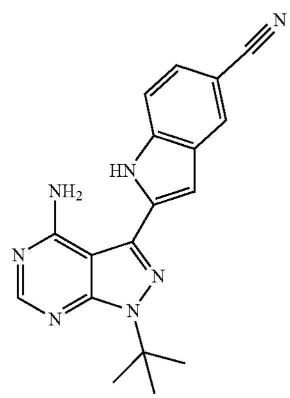 [SMILES: CC(C)(C)n1nc(-c2cc3cc(C#N)ccc3[nH]2)c2c(N)ncnc21] | 3 |
| 55 | 3-(3-Chloro-1H-pyrrolo[2,3-b]pyridin-2-yl)-1-isopropyl-1H-pyrazolo[3,4-d]pyrimidin-4-amine | 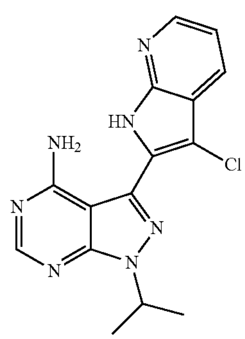 [SMILES: CC(C)n1nc(-c2[nH]c3ncccc3c2Cl)c2c(N)ncnc21] | 6 |
| 56 | 3-(3-Chloro-1H-pyrrolo[2,3-b]pyridin-2-yl)-1-(tetrahydro-2H-pyran-4-yl)-1H-pyrazolo[3,4-d]pyrimidin-4-amine | 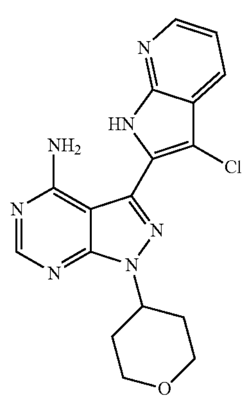 [SMILES: Nc1ncnc2c1c(-c1[nH]c3ncccc3c1Cl)nn2C1CCOCC1] | 6 |

TABLE C-continued

List of Examples and their method of synthesis

| Example | Name | Structure | General Method |
|---|---|---|---|
| 57 | 4-((4-Amino-3-(3-chloro-1H-pyrrolo[2,3-b]pyridin-2-yl)-1H-pyrazolo[3,4-d]pyrimidin-1-yl)methyl)benzonitrile | 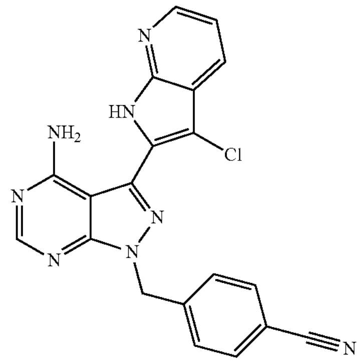 [SMILES: N#Cc1ccc(Cn2nc(-c3[nH]c4ncccc4c3Cl)c3c(N)ncnc32)cc1] | 6 |
| 58 | 1-(Azetidin-3-yl)-3-(3-chloro-1H-pyrrolo[2,3-b]pyridin-2-yl)-1H-pyrazolo[3,4-d]pyrimidin-4-amine | 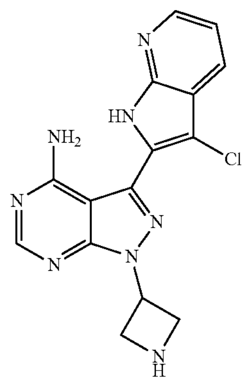 [SMILES: Nc1ncnc2c1c(-c1[nH]c3ncccc3c1Cl)nn2C1CNC1] | 6 |
| 59 | 3-(3-Chloro-1H-pyrrolo[2,3-b]pyridin-2-yl)-1-((tetrahydro-2H-pyran-4-yl)methyl)-1H-pyrazolo[3,4-d]pyrimidin-4-amine | 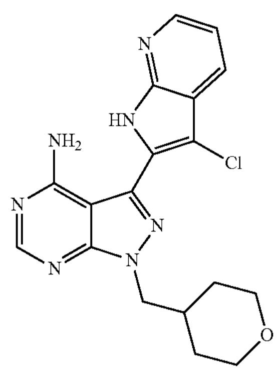 [SMILES: Nc1ncnc2c1c(-c1[nH]c3ncccc3c1Cl)nn2CC1CCOCC1] | 6 |
| 60 | 3-(3-Chloro-1H-pyrrolo[2,3-b]pyridin-2-yl)-1-((tetrahydro-2H-pyran-2-yl)methyl)-1H-pyrazolo[3,4-d]pyrimidin-4-amine | 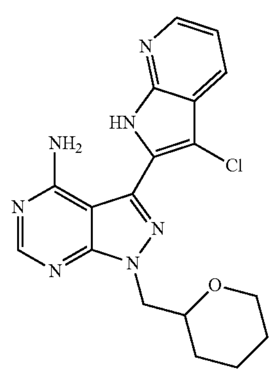 [SMILES: Nc1ncnc2c1c(-c1[nH]c3ncccc3c1Cl)nn2CC1CCCCO1] | 6 |

TABLE C-continued

List of Examples and their method of synthesis

| Example | Name | Structure | General Method |
|---|---|---|---|
| 61 | 3-(3-Chloro-1H-pyrrolo[2,3-b]pyridin-2-yl)-1-(2,2,2-trifluoroethyl)-1H-pyrazolo[3,4-d]pyrimidin-4-amine | 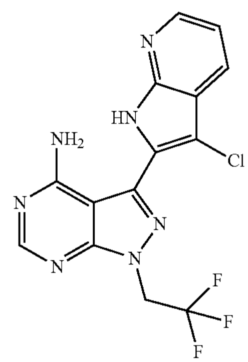 [SMILES: Nc1ncnc2c1c(-c1[nH]c3ncccc3c1Cl)nn2CC(F)(F)F] | 6 |
| 62 | 1-(sec-Butyl)-3-(3-chloro-1H-pyrrolo[2,3-b]pyridin-2-yl)-1H-pyrazolo[3,4-d]pyrimidin-4-amine | 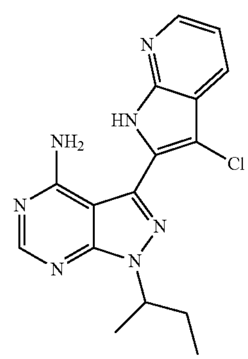 [SMILES: CCC(C)n1nc(-c2[nH]c3ncccc3c2Cl)c2c(N)ncnc21] | 6 |
| 63 | 3-(3-Chloro-1H-indol-2-yl)-1-cyclohexyl-pyrazolo[3,4-d]pyrimidin-4-amine | 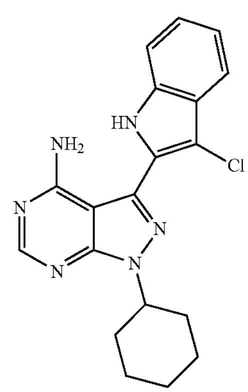 [SMILES: Nc1ncnc2c1c(-c1[nH]c3ccccc3c1Cl)nn2C1CCCCC1] | 4 |
| 64 | 3-(3-Chloro-1H-indol-2-yl)-1-isopropyl-pyrazolo[3,4-d]pyrimidin-4-amine | 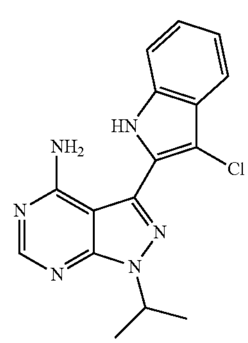 [SMILES: CC(C)n1nc(-c2[nH]c3ccccc3c2Cl)c2c(N)ncnc21] | 4 |

TABLE C-continued

List of Examples and their method of synthesis

| Example | Name | Structure | General Method |
|---|---|---|---|
| 65 | 3-(3-Chloro-1H-pyrrolo[2,3-b]pyridin-2-yl)-1-methyl-pyrazolo[3,4-d]pyrimidin-4-amine | 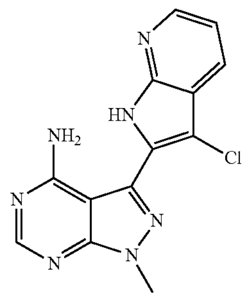 [SMILES: Cn1nc(-c2[nH]c3ncccc3c2Cl)c2c(N)ncnc21] | 5 |
| 66 | 3-(3-Chloro-1H-pyrrolo[2,3-b]pyridin-2-yl)-1-cyclobutyl-pyrazolo[3,4-c]pyrimidin-4-amine | 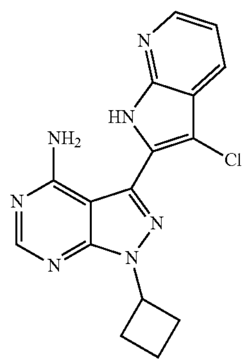 [SMILES: Nc1ncnc2c1c(-c1[nH]c3ncccc3c1Cl)nn2C1CCC1] | 5 |
| 67 | 3-(3-Chloro-1H-pyrrolo[2,3-b]pyridin-2-yl)-1-cyclohexyl-pyrazolo[3,4-d]pyrimidin-4-amine | 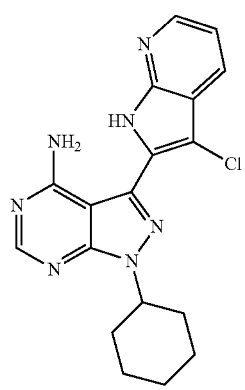 [SMILES: Nc1ncnc2c1c(-c1[nH]c3ncccc3c1Cl)nn2C1CCCCC1] | 5 |
| 68 | N-[trans-4-[4-Amino-3-(3-chloro-1H-pyrrolo[2,3-b]pyridin-2-yl)pyrazolo[3,4-d]pyrimidin-1-yl]cyclohexyl]cyclopropanecarboxamide | 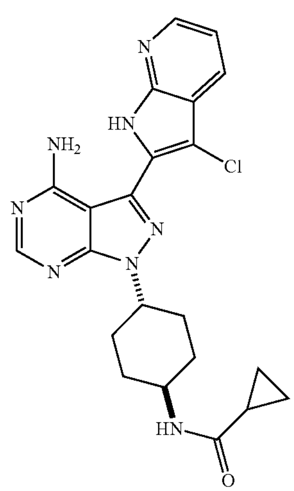 | 5 |

TABLE C-continued

List of Examples and their method of synthesis

| Example | Name | Structure | General Method |
|---|---|---|---|
| 69 | 3-[4-Amino-3-(3-chloro-1H-pyrrolo[2,3-b]pyridin-2-yl)pyrazolo[3,4-d]pyrimidin-1-yl]cyclopentanol | 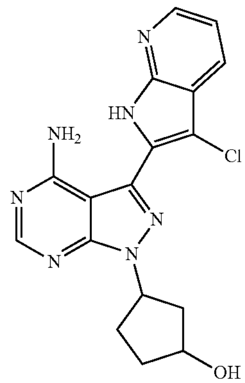 [SMILES: Nc1ncnc2c1c(-c1[nH]c3ncccc3c1Cl)nn2C1CCC(O)C1] | 5 |
| 70 | 1-tert-Butyl-3-(6-methyl-1H-indol-2-yl)pyrazolo[3,4-d]pyrimidin-4-amine | 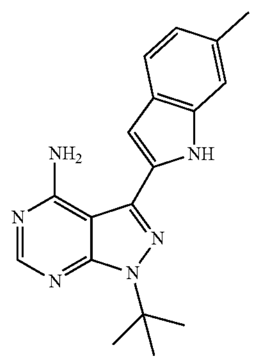 [SMILES: Cc1ccc2cc(-c3nn(C(C)(C)C)c4ncnc(N)c34)[nH]c2c1] | 3 |
| 71 | 1-tert-Butyl-3-(3-chloro-6-methyl-1H-indol-2-yl)pyrazolo[3,4-d]pyrimidin-4-amine | 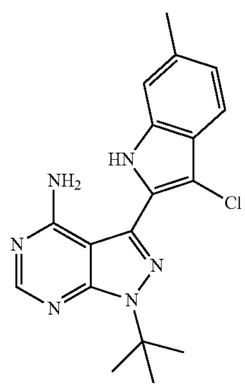 [SMILES: Cc1ccc2c(Cl)c(-c3nn(C(C)(C)C)c4ncnc(N)c34)[nH]c2c1] | 5 |
| 72 | 1-(tert-Butyl)-3-(3-chloro-6-((dimethylamino)methyl)-1H-indol-2-yl)-1H-pyrazolo[3,4-d]pyrimidin-4-amine | 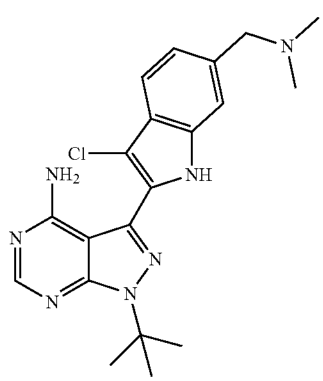 [SMILES: CN(C)Cc1ccc2c(Cl)c(-c3nn(C(C)(C)C)c4ncnc(N)c34)[nH]c2c1] | See Below |

TABLE C-continued

List of Examples and their method of synthesis

| Example | Name | Structure | General Method |
|---|---|---|---|
| 73 | 7-Chloro-1-isopropyl-3-(1H-pyrrolo[2,3-b]pyridin-2-yl)-1H-pyrazolo[4,3-c]pyridin-4-amine | 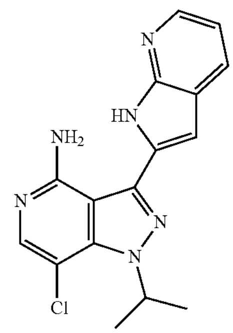 [SMILES: CC(C)n1nc(-c2cc3cccnc3[nH]2)c2c(N)ncc(Cl)c21] | 3 |
| 74 | 1-tert-Butyl-3-(5-fluoro-1H-indol-2-yl)pyrazolo[3,4-d]pyrimidin-4-amine | 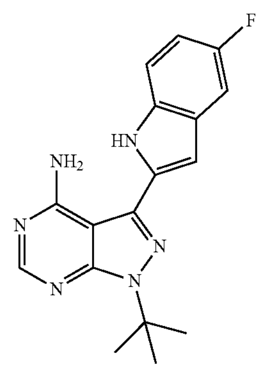 [SMILES: CC(C)(C)n1nc(-c2cc3cc(F)ccc3[nH]2)c2c(N)ncnc21] | 3 |
| 75 | 1-tert-Butyl-3-(4-chloro-1H-indol-2-yl)pyrazolo[3,4-d]pyrimidin-4-amine | 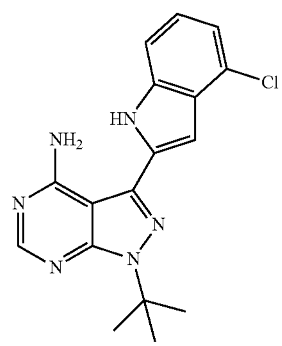 [SMILES: CC(C)(C)n1nc(-c2cc3c(Cl)cccc3[nH]2)c2c(N)ncnc21] | 3 |
| 76 | 1-(tert-Butyl)-3-(3-fluoro-1H-indol-2-yl)-1H-pyrazolo[3,4-d]pyrimidin-4-amine | 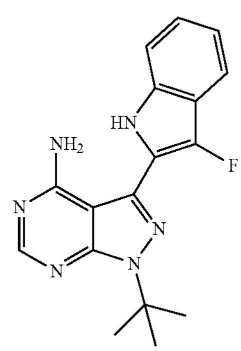 [SMILES: CC(C)(C)n1nc(-c2[nH]c3ccccc3c2F)c2c(N)ncnc21] | See Below |

TABLE C-continued

List of Examples and their method of synthesis

| Example | Name | Structure | General Method |
|---|---|---|---|
| 77 | 3-(3-Chloro-1H-pyrrolo[2,3-b]pyridin-2-yl)-1-(2-(4-(dimethylamino)piperidin-1-yl)ethyl)-1H-pyrazolo[3,4-d]pyrimidin-4-amine | 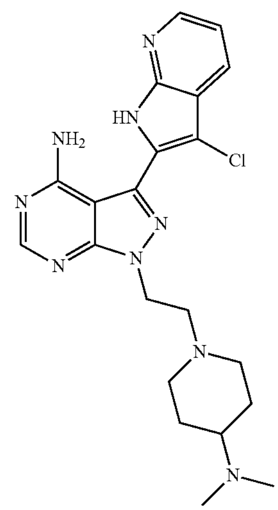 [SMILES: CN(C)C1CCN(CCn2nc(-c3[nH]c4ncccc4c3Cl)c3c(N)ncnc32)CC1] | See Below |
| 78 | 3-(3-Chloro-1H-pyrrolo[2,3-b]pyridin-2-yl)-1-(tetrahydrofuran-3-yl)-1H-pyrazolo[3,4-d]pyrimidin-4-amine | 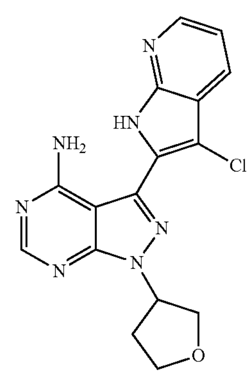 [SMILES: Nc1ncnc2c1c(-c1[nH]c3ncccc3c1Cl)nn2C1CCOC1] | 6 |
| 79 | 3-(3-Chloro-1H-pyrrolo[2,3-b]pyridin-2-yl)-1-cyclopentyl-1H-pyrazolo[3,4-d]pyrimidin-4-amine | 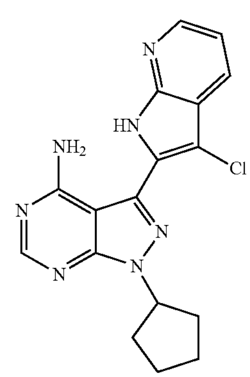 [SMILES: Nc1ncnc2c1c(-c1[nH]c3ncccc3c1Cl)nn2C1CCCC1] | 6 |

TABLE C-continued

List of Examples and their method of synthesis

| Example | Name | Structure | General Method |
|---|---|---|---|
| 80 | 3-(3-Chloro-1H-pyrrolo[2,3-b]pyridin-2-yl)-1-isopentyl-1H-pyrazolo[3,4-d]pyrimidin-4-amine | 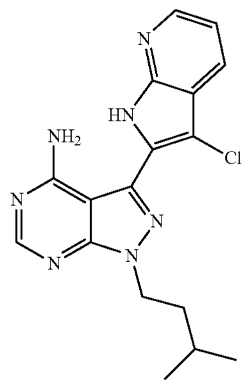 [SMILES: CC(C)CCn1nc(-c2[nH]c3ncccc3c2Cl)c2c(N)ncnc21] | 6 |
| 81 | 3-(3-Chloro-1H-pyrrolo[2,3-b]pyridin-2-yl)-1-neopentyl-1H-pyrazolo[3,4-d]pyrimidin-4-amine | 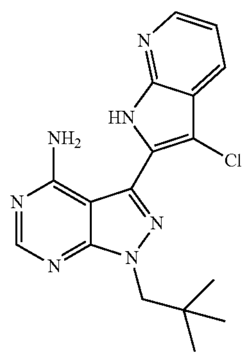 [SMILES: CC(C)(C)Cn1nc(-c2[nH]c3ncccc3c2Cl)c2c(N)ncnc21] | 6 |
| 82 | 3-(3-Chloro-1H-pyrrolo[2,3-b]pyridin-2-yl)-1-propyl-1H-pyrazolo[3,4-d]pyrimidin-4-amine | 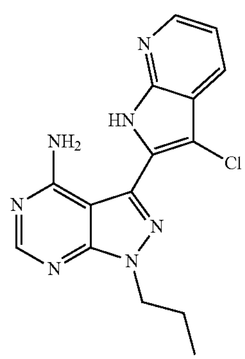 [SMILES: CCCn1nc(-c2[nH]c3ncccc3c2Cl)c2c(N)ncnc21] | 6 |
| 83 | 1-tert-Butyl-3-(3-chloro-5-fluoro-1H-indol-2-yl)pyrazolo[3,4-d]pyrimidin-4-amine | 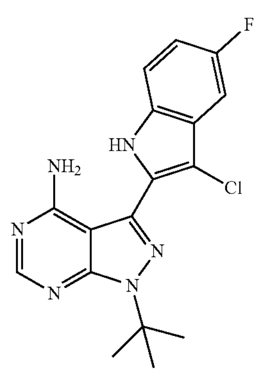 [SMILES: CC(C)(C)n1nc(-c2[nH]c3ccc(F)cc3c2Cl)c2c(N)ncnc21] | 5 |

TABLE C-continued

List of Examples and their method of synthesis

| Example | Name | Structure | General Method |
|---|---|---|---|
| 84 | 1-tert-Butyl-3-(5-methyl-1H-indol-2-yl)pyrazolo[3,4-d]pyrimidin-4-amine | 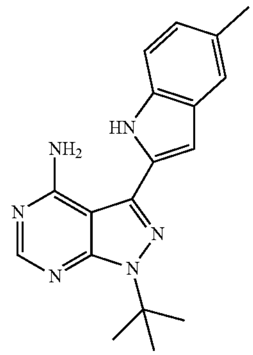 [SMILES: Cc1ccc2[nH]c(-c3nn(C(C)(C)C)c4ncnc(N)c34)cc2c1] | 3 |
| 85 | 3-(3-Chloro-1H-indol-2-yl)-1-((tetrahydro-2H-pyran-4-yl)methyl)-1H-pyrazolo[3,4-d]pyrimidin-4-amine | 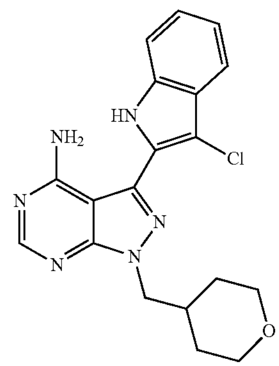 [SMILES: Nc1ncnc2c1c(-c1[nH]c3ccccc3c1Cl)nn2CC1CCOCC1] | 7 |
| 86 | 3-(3-Chloro-1H-indol-2-yl)-1-(tetrahydrofuran-3-yl)-1H-pyrazolo[3,4-d]pyrimidin-4-amine | 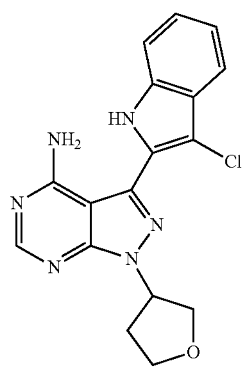 [SMILES: Nc1ncnc2c1c(-c1[nH]c3ccccc3c1Cl)nn2C1CCOC1] | 7 |
| 87 | 3-(3-Chloro-1H-pyrrolo[2,3-b]pyridin-2-yl)-1-(2-(piperidin-1-yl)ethyl)-1H-pyrazolo[3,4-d]pyrimidin-4-amine | 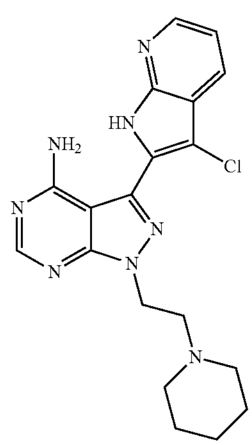 [SMILES: Nc1ncnc2c1c(-c1[nH]c3ncccc3c1Cl)nn2CCN1CCCCC1] | See Below |

TABLE C-continued

List of Examples and their method of synthesis

| Example | Name | Structure | General Method |
|---|---|---|---|
| 88 | 2-(4-Amino-1-(tert-butyl)-1H-pyrazolo[3,4-d]pyrimidin-3-yl)-1H-pyrrolo[2,3-b]pyridine-6-carbonitrile | 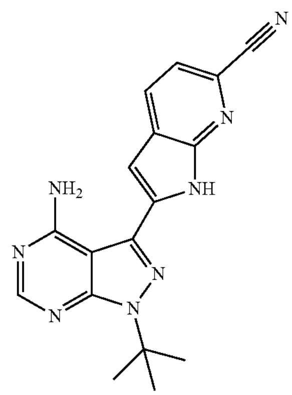 [SMILES: CC(C)(C)n1nc(-c2cc3ccc(C#N)nc3[nH]2)c2c(N)ncnc21] | See Below |

TABLE D

Examples Prepared Using General Methods

| Example | Formula | MW | Adduct | m/z | Yield (%) |
|---|---|---|---|---|---|
| 2 | C$_{19}$H$_{21}$N$_7$O$_2$S | 411.48 | [M − H]$^-$ | 410.1 | 76 |
| 4 | C$_{19}$H$_{20}$ClN$_7$O$_2$S | 445.93 | [M − H]$^-$ | 444.1 | 11 |
| 5 | C$_{23}$H$_{25}$N$_7$O | 415.49 | [M − H]$^-$ | 414.2 | 62 |
| 6 | C$_{23}$H$_{27}$N$_7$O | 417.51 | [M − H]$^-$ | 416.2 | 76 |
| 8 | C$_{23}$H$_{24}$ClN$_7$O | 449.94 | [M − H]$^-$ | 448.2 | 26 |
| 9 | C$_{16}$H$_{17}$N$_7$ | 307.35 | [M + H]$^+$ | 308.3 | 53 |
| 10 | C$_{16}$H$_{16}$ClN$_7$ | 341.8 | [M + H]$^+$ | 342.3 | 12 |
| 11 | C$_{17}$H$_{17}$N$_5$ | 291.35 | [M + H]$^+$ | 292.4 | 35 |
| 12 | C$_{17}$H$_{16}$ClN$_5$ | 325.8 | [M + H]$^+$ | 324.3 | 43 |
| 13 | C$_{17}$H$_{17}$N$_5$ | 291.35 | [M + H]$^+$ | 292.3 | 78 |
| 14 | C$_{17}$H$_{16}$ClN$_5$ | 325.8 | [M + H]$^+$ | 326.3 | 5 |
| 15 | C$_{16}$H$_{15}$BrN$_6$ | 371.23 | [M + H]$^+$ | 373.1 | 38 |
| 16 | C$_{16}$H$_{14}$BrClN$_6$ | 405.68 | [M + H]$^+$ | 407.1 | 23 |
| 17 | C$_{18}$H$_{17}$N$_7$ | 331.37 | [M + H]$^+$ | 332.4 | 38 |
| 18 | C$_{18}$H$_{16}$ClN$_7$ | 365.82 | [M + H]$^+$ | 366.4 | 80 |
| 20 | C$_{17}$H$_{17}$ClN$_6$ | 340.81 | [M + H]$^+$ | 341.1 | 37 |
| 21 | C$_{16}$H$_{16}$N$_6$ | 292.34 | [M − H]$^-$ | 291.2 | 6 |
| 22 | C$_{18}$H$_{20}$N$_8$O$_2$S | 412.47 | [M + H]$^+$ | 413.2 | 44 |
| 23 | C$_{18}$H$_{19}$ClN$_8$O$_2$S | 446.91 | [M + H]$^+$ | 447.1 | 20 |
| 24 | C$_{17}$H$_{16}$Cl$_2$N$_6$ | 375.26 | [M + H]$^+$ | 375.2 | 42 |
| 27 | C$_{23}$H$_{28}$N$_8$O$_2$ | 448.52 | [M + H]$^+$ | 447.3 | 21 |
| 28 | C$_{23}$H$_{28}$N$_8$O$_2$ | 448.52 | [M − H]$^-$ | 447.3 | 75 |
| 29 | C$_{23}$H$_{27}$ClN$_8$O$_2$ | 482.97 | [M − H]$^-$ | 481.3 | 39 |
| 30 | C$_{23}$H$_{27}$ClN$_8$O$_2$ | 482.97 | [M − H]$^-$ | 481.3 | 33 |
| 31 | C$_{13}$H$_{11}$N$_7$ | 265.27 | [M + H]$^+$ | 266.1 | 50 |
| 32 | C$_{16}$H$_{16}$N$_6$ | 292.34 | [M + H]$^+$ | 293.3 | 39 |
| 33 | C$_{16}$H$_{15}$ClN$_6$ | 326.78 | [M + H]$^+$ | 327.3 | 3 |
| 36 | C$_{22}$H$_{24}$N$_8$O | 416.48 | [M + H]$^+$ | 417.7 | 38 |
| 37 | C$_{15}$H$_{13}$N$_7$ | 293.33 | [M − H]$^-$ | 292.7 | 32 |
| 39 | C$_{19}$H$_{20}$N$_6$ | 332.4 | [M + H]$^+$ | 333.8 | 53 |
| 40 | C$_{17}$H$_{17}$N$_7$O | 335.36 | [M − H]$^-$ | 334.7 | 33 |
| 41 | C$_{18}$H$_{19}$N$_7$ | 333.39 | [M − H]$^-$ | 332.7 | 39 |
| 42 | C$_{16}$H$_{15}$N$_7$ | 305.34 | [M − H]$^-$ | 304.7 | 33 |
| 43 | C$_{14}$H$_{13}$N$_7$ | 279.3 | [M − H]$^-$ | 278.6 | 52 |
| 44 | C$_{16}$H$_{16}$N$_6$ | 292.34 | [M − H]$^-$ | 291.7 | 58 |
| 45 | C$_{16}$H$_{15}$ClN$_6$ | 326.78 | [M − H]$^-$ | 325.7 | 2 |
| 46 | C$_{14}$H$_{12}$ClN$_7$ | 313.74 | [M − H]$^-$ | 312.6 | 73 |
| 47 | C$_{17}$H$_{17}$N$_5$ | 291.35 | [M + H]$^+$ | 292.7 | 43 |
| 48 | C$_{17}$H$_{16}$ClN$_5$ | 325.8 | [M + H]$^+$ | 326.7 | 8 |
| 50 | C$_{16}$H$_{16}$ClN$_7$ | 341.8 | [M + H]$^+$ | 342.4 | 10 |
| 51 | C$_{16}$H$_{15}$Cl$_2$N$_7$ | 376.24 | [M + H]$^+$ | 376.3 | 25 |
| 53 | C$_{17}$H$_{16}$Cl$_2$N$_6$ | 375.26 | [M + H]$^+$ | 375.6 | 22 |
| 54 | C$_{18}$H$_{17}$N$_7$ | 331.37 | [M − H]$^-$ | 330.8 | 44 |
| 56 | C$_{17}$H$_{16}$ClN$_7$O | 369.81 | [M + H]$^+$ | 369.9 | 9 |
| 57 | C$_{20}$H$_{13}$ClN$_8$ | 400.82 | [M + H]$^+$ | 400.9 | 9 |
| 58 | C$_{15}$H$_{13}$ClN$_8$ | 340.77 | [M + H]$^+$ | 341.4 | 6 |
| 59 | C$_{18}$H$_{18}$ClN$_7$O | 383.83 | [M + H]$^+$ | 384.3 | 13 |
| 60 | C$_{18}$H$_{18}$ClN$_7$O | 383.83 | [M + H]$^+$ | 384.4 | 6 |
| 61 | C$_{14}$H$_{9}$ClF$_3$N$_7$ | 367.72 | [M + H]$^+$ | 368.3 | 5 |
| 62 | C$_{16}$H$_{16}$ClN$_7$ | 341.8 | [M + H]$^+$ | 342.3 | 19 |
| 63 | C$_{19}$H$_{19}$ClN$_6$ | 366.85 | [M + H]$^+$ | 367.7 | 3 |
| 64 | C$_{16}$H$_{15}$ClN$_6$ | 326.78 | [M + H]$^+$ | 327.7 | 3 |
| 65 | C$_{13}$H$_{10}$ClN$_7$ | 299.72 | [M − H]$^-$ | 298.6 | 5 |
| 66 | C$_{16}$H$_{14}$ClN$_7$ | 339.78 | [M + H]$^+$ | 340.3 | 43 |
| 67 | C$_{18}$H$_{18}$ClN$_7$ | 367.84 | [M − H]$^-$ | 366.7 | 2 |
| 68 | C$_{22}$H$_{23}$ClN$_8$O | 450.92 | [M − H]$^-$ | 449.7 | 39 |
| 69 | C$_{17}$H$_{16}$ClN$_7$O | 369.81 | [M + H]$^+$ | 368.7 | 14 |
| 70 | C$_{18}$H$_{20}$N$_6$ | 320.39 | [M − H]$^-$ | 319.8 | 2 |
| 71 | C$_{18}$H$_{19}$ClN$_6$ | 354.84 | [M − H]$^-$ | 353.7 | 11 |
| 73 | C$_{16}$H$_{15}$ClN$_6$ | 326.78 | [M + H]$^+$ | 327.3 | 6 |
| 74 | C$_{17}$H$_{17}$N$_6$ | 324.36 | [M + H]$^+$ | 323.7 | 42 |
| 75 | C$_{17}$H$_{17}$ClN$_6$ | 340.81 | [M + H]$^+$ | 341.7 | 18 |
| 78 | C$_{16}$H$_{14}$ClN$_7$O | 355.78 | [M + H]$^+$ | 356.1 | 15 |
| 79 | C$_{17}$H$_{16}$ClN$_7$ | 353.81 | [M + H]$^+$ | 354.4 | 27 |
| 80 | C$_{17}$H$_{18}$ClN$_7$ | 355.82 | [M + H]$^+$ | 356.4 | 16 |
| 81 | C$_{17}$H$_{18}$ClN$_7$ | 355.82 | [M + H]$^+$ | 356.3 | 8 |
| 82 | C$_{15}$H$_{14}$ClN$_7$ | 327.77 | [M + H]$^+$ | 328.3 | 13 |
| 83 | C$_{17}$H$_{16}$ClFN$_6$ | 358.8 | [M + H]$^+$ | 359.7 | 22 |
| 84 | C$_{18}$H$_{20}$N$_6$ | 320.39 | [M + H]$^+$ | 321.7 | 27 |
| 85 | C$_{19}$H$_{9}$ClN$_6$O | 382.85 | [M + H]$^+$ | 383.5 | 53 |
| 86 | C$_{17}$H$_{15}$ClN$_6$O | 354.79 | [M + H]$^+$ | 354.9 | 34 |

TABLE E

$^1$H NMR data for Examples

| EXAMPLE | $^1$H NMR (300 or 400 MHz, DMSO-d$_6$) δ |
|---|---|
| 2 | 11.60 (br s, 1H), 8.28 (s, 1H), 7.63 (d, J = 7.82 Hz, 1H), 7.47 (d, J = 7.81 Hz, 1H), 7.17 (dt, J = 1.18, 7.56 Hz, 1H), 7.01-7.09 (m, 1H), 6.88 (s, 1H), 4.83-4.97 (m, 1H), 3.75 (br d, J = 12.24 Hz, 2H), 2.99-3.10 (m, 2H), 2.96 (s, 3H), 2.18-2.37 (m, 2H), 2.03-2.15 (m, 2H). |

TABLE E-continued

¹H NMR data for Examples

| EXAMPLE | ¹H NMR (300 or 400 MHz, DMSO-d₆) δ |
|---|---|
| 4 | 11.89 (s, 1H), 8.28 (s, 1H), 7.58 (d, J = 8.01 Hz, 1H), 7.49 (d, J = 8.01 Hz, 1H), 7.24-7.31 (m, 1H), 7.16-7.24 (m, 1H), 4.92 (s, 1H), 3.74 (br d, J = 12.24 Hz, 2H), 3.06 (br t, J = 11.82 Hz, 2H), 2.95 (s, 3H), 2.09-2.31 (m, 4H). |
| 5 | 11.58 (s, 1H), 8.27 (s, 1H), 8.09 (d, J = 7.63 Hz, 1H), 7.63 (d, J = 7.84 Hz, 1H), 7.48 (dd, J = 0.98, 8.12 Hz, 1H), 7.17 (ddd, J = 1.24, 7.05, 8.16 Hz, 1H), 7.05 (ddd, J = 1.08, 7.01, 7.97 Hz, 1H), 6.85 (s, 1H), 4.72 (t, J = 11.17 Hz, 1H), 3.76-3.63 (m, 1H), 2.21-2.05 (m, 2H), 2.05-1.94 (m, 4H), 1.62-1.38 (m, 2H), 0.73-0.57 (m, 4H). NH₂ not visible. |
| 6 | 11.56 (s, 1H), 8.26 (s, 1H), 7.62 (d, J = 7.81 Hz, 1H), 7.48 (dd, J = 1.03, 8.08 Hz, 1H), 7.16 (ddd, J = 1.24, 6.98, 8.20 Hz, 1H), 7.05 (ddd, J = 1.10, 7.01, 7.99 Hz, 1H), 6.85 (s, 1H), 4.76-4.61 (m, 1H), 3.59 (t, J = 4.55 Hz, 4H), 2.35 (t, J = 11.42 Hz, 1H), 2.21-1.91 (m, 6H), 1.57-1.39 (m, 2H). 2 × CH₂ under DMSO peak. NH₂ not visible. |
| 8 | 11.88 (s, 1H), 8.27 (s, 1H), 8.08 (d, J = 7.62 Hz, 1H), 7.57 (d, J = 7.73 Hz, 1H), 7.48 (d, J = 8.13 Hz, 1H), 7.27 (ddd, J = 1.12, 6.86, 8.20 Hz, 1H), 7.23-7.13 (m, 1H), 6.99 (bis, 2H), 4.82-4.65 (m, 1H), 3.71-3.59 (m, 1H), 2.11-1.93 (m, 7H), 1.62-1.38 (m, 2H), 0.73-0.56 (m, 4H). |
| 9 | 12.11 (br s, 1H), 8.30-8.24 (over-lapping m, 2H), 8.03 (dd, J = 7.8, 1.2 Hz, 1H), 7.12 (dd, J = 7.8, 4.7 Hz, 1H), 7.01 (br s, 2H), 6.80 (s, 1H), 1.78 (s, 9H). |
| 10 | 12.50 (bis, 1H), 8.34 (dd, J = 4.7, 1.6 Hz, 1H), 8.24 (s, 1H), 7.98 (dd, J = 7.9, 1.6 Hz, 1H), 7.48-6.84 (bis, 2H), 7.21 (dd, J = 7.9, 4.7 Hz, 1H), 1.78 (s, 9H). |
| 11 | 11.55 (s, 1H), 7.77 (d, J = 6.1 Hz, 1H), 7.63 (d, J = 7.8 Hz, 1H), 7.50-7.46 (m, 1H), 7.16 (app ddd, 1H), 7.05 (app ddd, 1H), 6.93 (d, J = 6.1 Hz, 1H), 6.83-6.80 (m, 1H), 6.14 (s, 2H), 4.92 (hept, J = 6.5 Hz, 1H), 1.53 (d, J = 6.6 Hz, 6H). |
| 12 | 11.94 (s, 1H), 7.78 (d, J = 6.1 Hz, 1H), 7.58 (d, J = 7.8 Hz, 1H), 7.49 (app d, 1H), 7.28 (app ddd, 1H), 7.20 (app ddd, 1H), 6.96 (d, J = 6.1 Hz, 1H), 5.85 (s, 2H), 4.95 (hept, J = 6.6 Hz, 1H), 1.52 (d, J = 6.6 Hz, 6H). |
| 13 | 11.44 (s, 1H), 7.95 (s, 1H), 7.55 (d, J = 7.9 Hz, 1H), 7.39 (dd, J = 8.0, 1.0 Hz, 1H), 7.26-6.89 (bis, 2H), 7.10 (ddd, J = 8.0, 7.0, 1.3 Hz, 1H), 7.02 (ddd, J = 8.0, 7.1, 1.1 Hz, 1H), 6.73 (s, 1H), 6.51 (br dd, 1H), 3.44 (hept, J = 6.8 Hz, 1H), 1.34 (d, J = 6.8 Hz, 6H). |
| 14 | 11.67 (s, 1H), 7.97 (s, 1H), 7.51 (d, J = 7.6 Hz, 1H), 7.41 (d, J = 7.9 Hz, 1H), 7.22 (ddd, J = 8.2, 7.1, 1.3 Hz, 1H), 7.15 (ddd, J = 8.0, 7.1, 1.1 Hz, 1H), 6.71 (s, 1H), 3.45 (hept, J = 6.9 Hz, 1H), 1.34 (d, J = 6.9 Hz, 6H). NH₂ signals not present. |
| 15 | 11.71 (s, 1H), 8.27 (s, 1H), 7.63 (d, J = 1.76 Hz, 1H), 7.59 (d, J = 8.43 Hz, 1H), 7.18 (dd, J = 1.82, 8.41 Hz, 1H), 7.11 (br s, 2H), 6.88 (s, 1H), 5.10 (p, J = 6.72 Hz, 1H), 1.54 (d, J = 6.74 Hz, 6H). |
| 16 | 11.94 (s, 1H), 8.18 (s, 1H), 7.56 (d, J = 1.65 Hz, 1H), 7.44 (d, J = 8.47 Hz, 1H), 7.23 (dd, J = 1.71, 8.51 Hz, 1H), 7.02 (br s, 2H), 5.03 (p, J = 6.69 Hz, 1H), 1.45 (d, J = 6.67 Hz, 6H). |
| 17 | ND |
| 18 | 12.45 (s, 1H), 8.27 (s, 1H), 7.96 (apps, 1H), 7.73 (d, J = 8.2 Hz, 1H), 7.52 (dd, J = 8.2, 1.1 Hz, 1H), 6.99 (br, 2H), 1.78 (s, 9H). |
| 20 | 11.64 (s, 1H), 8.26 (s, 1H), 7.63 (d, J = 8.5 Hz, 1H), 7.49-7.47 (m, 1H), 7.07 (dd, J = 8.5, 1.9 Hz, 1H), 7.04 (br, 2H), 6.86 (s, 1H), 1.79 (s, 9H). |
| 21 | 11.89 (s, 1H), 8.22-8.14 (m, 2H), 7.93 (d, J = 7.73 Hz, 1H), 7.70 (s, 1H), 7.06 (dd, J = 4.75, 7.80 Hz, 1H), 6.52 (s, 1H), 6.46 (s, 2H), 5.07-4.91 (m, 1H), 1.48 (d, J = 6.72 Hz, 6H). |
| 22 | 12.20 (s, 1H), 8.28 (s, 2H), 8.04 (d, J = 7.21 Hz, 1H), 7.12 (dd, J = 4.73, 7.81 Hz, 1H), 6.86 (s, 1H), 4.97-4.83 (m, 1H), 3.74 (d, J = 11.90 Hz, 2H), 3.06 (t, J = 11.41 Hz, 2H), 2.96 (s, 3H), 2.35-2.22 (m, 2H), 2.13-2.02 (m, 2H). NH₂ not visible. |
| 23 | 12.46 (s, 1H), 8.38 (s, 1H), 8.27 (s, 1H), 8.02 (d, J = 7.76 Hz, 1H), 7.30-7.19 (m, 1H), 4.99-4.85 (m, 1H), 3.73 (d, J = 11.88 Hz, 2H), 3.06 (t, J = 10.85 Hz, 2H), 2.95 (s, 3H), 2.30-2.15 (m, 2H), 2.16-2.04 (m, 2H). NH₂ not visible. |
| 24 | 12.01 (br, 1H), 8.26 (s, 1H), 7.57 (d, J = 8.5 Hz, 1H), 7.50 (br dd, 1H), 7.20 (dd, J = 8.5, 1.9 Hz, 1H), 6.98 (br, 2H), 1.78 (s, 9H). |
| 27 | 12.08 (s, 1H), 8.29 (dd, J = 1.59, 4.63 Hz, 1H), 8.27 (s, 1H), 8.04 (d, J = 6.99 Hz, 1H), 7.13 (dd, J = 4.69, 7.87 Hz, 1H), 6.84 (d, J = 1.98 Hz, 1H), 4.89-4.67 (m, 1H), 3.57 (s, 1H), 2.33-2.16 (m, 2H), 2.00-1.93 (m, 2H), 1.84-1.74 (m, 2H), 1.74-1.60 (m, 2H), 1.41 (s, 9H). NH₂ not visible. |
| 28 | 12.16 (s, 1H), 8.29 (dd, J = 1.61, 4.78 Hz, 1H), 8.26 (s, 1H), 8.03 (d, J = 7.47 Hz, 1H), 7.12 (dd, J = 4.66, 7.81 Hz, 1H), 6.87 (d, J = 7.86 Hz, 1H), 6.82 (d, J = 1.91 Hz, 1H), 4.72-4.58 (m, 1H), 2.24-1.83 (m, 5H), 1.52-1.41 (m, 2H), 1.41 (s, 9H). 1 × CH₂ not visible. |
| 29 | 12.46 (s, 1H), 8.36 (d, J = 4.23 Hz, 1H), 8.25 (s, 1H), 7.99 (dd, J = 1.58, 7.94 Hz, 1H), 7.22 (dd, J = 4.72, 7.87 Hz, 1H), 6.92 (s, 1H), 4.85-4.69 (m, 1H), 3.58 (s, 1H), 2.36-2.19 (m, 2H), 1.98-1.88 (m, 2H), 1.82-1.60 (m, 4H), 1.39 (s, 9H). |
| 30 | 12.50 (s, 1H), 8.36 (d, J = 2.84 Hz, 1H), 8.25 (s, 1H), 8.00 (d, J = 7.84 Hz, 1H), 7.28-7.17 (m, 1H), 6.86 (d, J = 7.81 Hz, 1H), 4.67 (s, 1H), 1.97 (d, J = 12.78 Hz, 4H), 1.52-1.42 (m, 2H), 1.40 (s, 9H). 1 × CH and 1 × CH₂ not visible. |
| 31 | 8.22 (s, 1H), 8.14 (br s, 1H), 7.89 (d, J = 7.52 Hz, 1H), 6.94 (br s, 1H), 6.78 (s, 1H), 3.95 (s, 3H). NH₂ and indole NH not visible. |

TABLE E-continued

¹H NMR data for Examples

| EXAMPLE | ¹H NMR (300 or 400 MHz, DMSO-d₆) δ |
|---|---|
| 32 | 12.12 (s, 1H), 8.28 (dd, J = 4.7, 1.6 Hz, 1H), 8.04 (dd, J = 7.8, 1.6 Hz, 1H), 7.77 (d, J = 6.1 Hz, 1H), 7.13 (dd, J = 7.8, 4.7 Hz, 1H), 6.94 (d, J = 6.1 Hz, 1H), 6.81 (s, 1H), 6.09 (s, 2H), 4.92 (hept, J = 6.6 Hz, 1H), 1.52 (d, J = 6.6 Hz, 6H). |
| 33 | 12.49 (br, 1H), 8.39 (dd, J = 4.7, 1.6 Hz, 1H), 8.02 (dd, J = 7.9, 1.6 Hz, 1H), 7.78 (d, J = 6.2 Hz, 1H), 7.26 (dd, J = 7.9, 4.7 Hz, 1H), 6.96 (d, J = 6.2 Hz, 1H), 5.90 (br, 2H), 4.95 (hept, J = 6.6 Hz, 1H), 1.52 (d, J = 6.6 Hz, 6H). |
| 36 | 12.14 (s, 1H), 8.29 (s, 1H), 8.27 (s, 1H), 8.07 (d, J = 7.70 Hz, 1H), 8.03 (d, J = 7.79 Hz, 1H), 7.12 (dd, J = 4.69, 7.82 Hz, 1H), 6.83 (s, 1H), 4.72 (t, J = 11.40 Hz, 1H), 3.72-3.62 (m, 1H), 2.12 (q, J = 11.22 Hz, 2H), 1.99 (d, J = 11.83 Hz, 4H), 1.62-1.37 (m, 3H), 0.72-0.57 (m, 3H). 1 × CH not visible. |
| 37 | 11.97 (s, 1H), 8.10 (s, 1H), 8.09 (s, 1H), 7.85 (dd, J = 1.60, 7.84 Hz, 1H), 6.94 (dd, J = 4.72, 7.83 Hz, 1H), 6.90 (br s, 2H), 6.65 (s, 1H), 4.91 (p, J = 6.70 Hz, 1H), 1.35 (d, J = 6.69 Hz, 6H). |
| 39 | 11.61-11.54 (m, 1H), 8.26 (s, 1H), 7.62 (d, J = 7.82 Hz, 1H), 7.48 (d, J = 8.06 Hz, 1H), 7.16 (t, J = 7.59 Hz, 1H), 7.05 (t, J = 7.44 Hz, 1H), 6.85 (d, J = 1.59 Hz, 1H), 4.79-4.62 (m, 1H), 2.11-1.82 (m, 6H), 1.73 (d, J = 12.75 Hz, 1H), 1.48 (q, J = 12.86 Hz, 2H), 1.36-1.17 (m, 1H). NH₂ not visible. |
| 40 | 12.21 (s, 1H), 8.29 (dd, J = 1.58, 4.75 Hz, 1H), 8.27 (s, 1H), 8.04 (dd, J = 1.55, 7.85 Hz, 1H), 7.13 (dd, J = 4.66, 7.85 Hz, 1H), 6.83 (d, J = 1.95 Hz, 1H), 5.20 (p, J = 8.12 Hz, 1H), 4.92 (br s, 1H), 4.29-4.18 (m, 1H), 2.49-2.33 (m, 1H), 2.34-2.11 (m, 1H), 2.16-1.98 (m, 2H), 1.99-1.72 (m, 2H). NH₂ not visible. Single isomer but not known if cis or trans. |
| 41 | 12.13 (s, 1H), 8.28 (dd, J = 1.61, 4.65 Hz, 1H), 8.26 (s, 1H), 8.03 (dd, J = 1.60, 7.90 Hz, 1H), 7.12 (dd, J = 4.72, 7.84 Hz, 1H), 7.08 (br s, 2H), 6.82 (d, J = 1.91 Hz, 1H), 4.79-4.62 (m, 1H), 2.12-1.83 (m, 6H), 1.72 (d, J = 12.71 Hz, 1H), 1.48 (q, J = 12.87 Hz, 2H), 1.27 (d, J = 13.86 Hz, 1H). |
| 42 | 12.20 (s, 1H), 8.30 (dd, J = 1.40, 4.85 Hz, 1H), 8.27 (s, 1H), 8.04 (d, J = 8.01 Hz, 1H), 7.13 (dd, J = 4.68, 7.84 Hz, 1H), 7.10 (br s, 2H), 6.85 (s, 1H), 5.37 (p, J = 8.37 Hz, 1H), 2.89-2.69 (m, 2H), 2.49-2.34 (m, 2H), 1.99-1.81 (m, 2H). |
| 43 | 12.21 (s, 1H), 8.28 (s, 1H), 8.27 (s, 1H), 8.03 (d, J = 8.01 Hz, 1H), 7.12 (dd, J = 4.70, 7.85 Hz, 1H), 6.83 (s, 1H), 4.41 (q, J = 7.18 Hz, 2H), 1.45 (t, J = 7.21 Hz, 3H). NH₂ under peak at 7.12 ppm. |
| 44 | 11.59 (s, 1H), 8.27 (s, 1H), 7.63 (d, J = 7.85 Hz, 1H), 7.49 (d, J = 7.99 Hz, 1H), 7.17 (ddd, J = 1.25, 6.99, 8.17 Hz, 1H), 7.10 (br s, 2H), 7.05 (ddd, J = 1.10, 7.03, 7.96 Hz, 1H), 6.85 (d, J = 1.22 Hz, 1H), 5.10 (p, J = 6.67 Hz, 1H), 1.54 (d, J = 6.68 Hz, 6H). |
| 45 | 8.52 (s, 1H), 8.44-8.35 (m, 1H), 8.11 (br s, 3H), 7.28 (dd, J = 5.03, 7.88 Hz, 1H), 4.96 (br s, 2H), 3.33 (s, 1H), 2.36-2.24 (m, 3H), 2.02 (s, 4H), 1.99-1.88 (m, 2H). Azaindole NH not visible. |
| 46 | 12.45 (s, 1H), 8.38 (d, J = 4.78 Hz, 1H), 8.27 (s, 1H), 8.01 (d, J = 8.10 Hz, 1H), 7.24 (dd, J = 4.71, 7.91 Hz, 1H), 7.09 (br s, 2H), 4.43 (q, J = 7.21 Hz, 2H), 1.45 (t, J = 7.22 Hz, 3H). |
| 47 | 11.34 (s, 1H), 8.17 (s, 1H), 7.62 (s, 1H), 7.55 (d, J = 7.66 Hz, 1H), 7.40 (s, 1H), 7.09 (t, J = 7.57 Hz, 1H), 7.01 (t, J = 6.94 Hz, 1H), 6.50 (d, J = 1.91 Hz, 1H), 6.43 (br s, 2H), 5.00 (p, J = 6.72 Hz, 1H), 1.49 (d, J = 6.75 Hz, 6H). |
| 48 | 11.63 (s, 1H), 8.19 (s, 1H), 7.67 (s, 1H), 7.62-7.46 (m, 1H), 7.53-7.35 (m, 1H), 7.27-7.10 (m, 2H), 6.23 (br s, 2H), 5.02 (p, J = 6.72 Hz, 1H), 1.50 (d, J = 6.73 Hz, 6H). |
| 50 | 12.36 (br, 1H), 8.28-8.25 (over-lapping m, 2H), 8.12 (br d, J = 2.4 Hz, 1H), 7.04 (br, 2H), 6.78 (s, 1H), 1.78 (s, 9H). |
| 51 | 12.63 (br s, 1H), 8.35 (br s, 1H), 8.25 (s, 1H), 8.07 (br s, 1H), 1.77 (s, 9H). NH₂ signals not present. |
| 53 | 12.20 (s, 1H), 8.27 (s, 1H), 7.44 (dd, J = 1.35, 7.69 Hz, 1H), 7.21 (t, J = 7.71 Hz, 1H), 7.16 (dd, J = 1.14, 7.75 Hz, 1H), 6.96 (br s, 2H), 1.78 (s, 9H). |
| 54 | 12.09 (s, 1H), 8.28 (s, 1H), 8.16 (dd, J = 0.70, 1.59 Hz, 1H), 7.63 (dt, J = 0.80, 8.42 Hz, 1H), 7.51 (dd, J = 1.59, 8.42 Hz, 1H), 7.09 (br s, 2H), 6.98 (s, 1H), 1.80 (s, 9H). |
| 56 | 8.35 (br, 1H), 8.25 (s, 1H), 8.01-7.96 (m, 1H), 7.25-7.17 (m, 1H), 5.01-4.96 (m, 1H), 4.04-4.00 (m, 2H), 3.59-3.54 (m, 2H), 2.28-2.18 (m, 2H), 1.97-1.90 (m, 2H). NH₂ and NH signals not observed. |
| 57 | 12.51 (br, 1H), 8.37 (br d, J = 4.7 Hz, 1H), 8.29 (s, 1H), 8.00 (dd, J = 8.0, 1.5 Hz, 1H), 7.83 (d, J = 8.4 Hz, 2H), 7.49-7.00 (br, 2H), 7.48 (d, J = 8.4 Hz, 2H), 7.23 (dd, J = 7.7, 4.7 Hz, 1H), 5.73 (s, 2H). |
| 58 | 8.28 (dd, J = 4.7, 1.7 Hz, 1H), 8.22 (s, 1H), 7.91 (dd, J = 7.9, 1.7 Hz, 1H), 7.10 (dd, J = 7.9, 4.7 Hz, 1H), 5.71 (p, J = 7.8 Hz, 1H), 4.33 (app t, 2H), 3.97 (app t, 2H). NH₂ and 2 × NH signals not observed. |
| 59 | 12.47 (br, 1H), 8.36 (br d, J = 2.7 Hz, 1H), 8.26 (s, 1H), 7.99 (br d, J = 7.9 Hz, 1H), 7.25-7.19 (m, 1H), 7.18-6.76 (br, 2H), 4.30 (d, J = 7.1 Hz, 2H), 3.85-3.81 (m, 2H), 3.29-3.22 (m, 2H), 2.24-2.19 (m, 1H), 1.50-1.43 (m, 2H), 1.37-1.26 (m, 2H). |
| 60 | 12.50 (br, 1H), 8.36 (br d, 1H), 8.25 (s, 1H), 8.00 (br dd, J = 7.9, 1.5 Hz, 1H), 7.23 (dd, J = 7.9, 4.7 Hz, 1H), 7.19-6.81 (br, 2H), 4.49 (dd, J = 14.0, 7.7 Hz, 1H), 4.27 (dd, J = 14.0, 4.8 Hz, 1H), 3.90-3.84 (m, 1H), 3.82-3.79 (m, 1H), 3.35-3.29 (m, assume 1H obscured by solvent), 1.84-1.75 (m, 1H), 1.63-1.59 (m, 1H), 1.49-1.44 (m, 3H), 1.36-1.28 (m, 1H). |

TABLE E-continued

¹H NMR data for Examples

| EXAMPLE | ¹H NMR (300 or 400 MHz, DMSO-d₆) δ |
|---|---|
| 61 | 12.50 (br, 1H), 8.39 (br d, J = 4.7 Hz, 1H), 8.33 (s, 1H), 8.03 (br d, J = 7.9 Hz, 1H), 7.54-6.86 (br, 2H), 7.25 (dd, J = 7.9, 4.7 Hz, 1H), 5.34 (q, J = 9.0 Hz, 2H). |
| 62 | 12.43 (br, 1H), 8.38 (br d, J = 4.6 Hz, 1H), 8.25 (s, 1H), 8.00 (br dd, J = 7.9, 1.6 Hz, 1H), 7.24 (dd, J = 7.9, 4.7 Hz, 1H), 7.02 (br, 2H), 4.91-4.83 (m, 1H), 2.06-1.95 (m, 1H), 1.91-1.81 (m, 1H), 1.51 (d, J = 6.7 Hz, 3H), 0.74 (t, J = 7.3 Hz, 3H). |
| 63 | 11.87 (s, 1H), 8.26 (s, 1H), 7.58 (d, J = 7.77 Hz, 1H), 7.49 (dt, J = 0.97, 8.08 Hz, 1H), 7.28 (ddd, J = 1.33, 7.03, 8.20 Hz, 1H), 7.19 (ddd, J = 1.08, 6.99, 7.96 Hz, 1H), 6.97 (br s, 2H), 4.73 (p, J = 8.03 Hz, 1H), 2.04-1.83 (m, 6H), 1.72 (d, J = 12.92 Hz, 1H), 1.55-1.43 (m, 2H), 1.36-1.21 (m, 1H). |
| 64 | 11.88 (s, 1H), 8.27 (s, 1H), 7.58 (d, J = 7.91 Hz, 1H), 7.54 (s, 0H), 7.49 (dt, J = 0.98, 8.11 Hz, 1H), 7.28 (ddd, J = 1.33, 7.04, 8.21 Hz, 1H), 7.20 (ddd, J = 1.12, 7.06, 8.05 Hz, 1H), 6.96 (br s, 2H), 5.11 (p, J = 6.68 Hz, 1H), 1.53 (d, J = 6.69 Hz, 6H). |
| 65 | 12.56 (s, 1H), 8.37 (dd, J = 1.58, 4.74 Hz, 1H), 8.28 (s, 1H), 8.01 (dd, J = 1.58, 7.89 Hz, 1H), 7.36 (br s, 2H), 7.24 (dd, J = 4.72, 7.92 Hz, 1H), 4.01 (s, 3H). |
| 66 | 12.48 (s, 1H), 8.36 (dd, J = 1.51, 4.71 Hz, 1H), 8.25 (s, 1H), 8.00 (dd, J = 1.50, 7.89 Hz, 1H), 7.31 (br s, 2H), 7.22 (dd, J = 4.73, 7.96 Hz, 1H), 5.38 (p, J = 8.47 Hz, 1H), 2.85-2.65 (m, 2H), 2.49-2.36 (m, 2H), 1.98-1.81 (m, 2H). |
| 67 | 8.27-8.23 (m, 1H), 8.20 (s, 1H), 7.88 (d, J = 7.72 Hz, 1H), 7.08 (s, 1H), 4.69 (tt, J = 5.14, 10.21 Hz, 1H), 2.05-1.85 (m, 6H), 1.71 (d, J = 12.73 Hz, 1H), 1.48 (q, J = 12.20, 12.84 Hz, 2H), 1.28-1.21 (m, 1H). |
| 68 | 12.45 (s, 1H), 8.38 (dd, J = 1.55, 4.89 Hz, 1H), 8.27 (s, 1H), 8.07 (d, J = 7.65 Hz, 1H), 8.01 (dd, J = 1.59, 7.97 Hz, 1H), 7.24 (dd, J = 4.73, 7.93 Hz, 1H), 7.09 (br s, 2H), 4.82-4.67 (m, 1H), 3.72-3.60 (m, 1H), 2.09-1.93 (m, 6H), 1.62-1.37 (m, 3H), 0.73-0.56 (m, 4H). |
| 69 | 12.45 (s, 1H), 8.38 (d, J = 4.53 Hz, 1H), 8.26 (s, 1H), 8.02 (d, J = 7.88 Hz, 1H), 7.25 (dd, J = 4.74, 7.95 Hz, 1H), 7.08 (br s, 2H), 5.22 (p, J = 8.14 Hz, 1H), 4.94 (d, J = 5.27 Hz, 1H), 4.23 (q, J = 5.75 Hz, 1H), 2.42 (dd, J = 6.97, 13.81 Hz, 1H), 2.28-1.99 (m, 3H), 1.99-1.70 (m, 2H). |
| 70 | 11.38 (s, 1H), 8.26 (s, 1H), 7.50 (d, J = 8.00 Hz, 1H), 7.27 (dq, J = 0.80, 1.63 Hz, 1H), 7.00 (br s, 2H), 6.89 (ddd, J = 0.60, 1.51, 8.07 Hz, 1H), 6.75 (d, J = 1.04 Hz, 1H), 2.42 (s, 3H), 1.79 (s, 9H). |
| 71 | 11.69 (s, 1H), 8.26 (s, 1H), 7.45 (d, J = 8.32 Hz, 1H), 7.26 (dt, J = 0.78, 1.58 Hz, 1H), 7.02 (dd, J = 1.35, 8.23 Hz, 1H), 6.89 (br s, 2H), 2.45 (s, 3H), 1.78 (s, 9H). |
| 73 | 12.21 (br, 1H), 8.34-8.24 (m, 1H), 8.05 (dd, J = 7.8, 1.6 Hz, 1H), 7.78 (s, 1H), 7.14 (dd, J = 7.8, 4.7 Hz, 1H), 6.83 (s, 1H), 6.27 (s, 2H), 5.57 (hept, J = 6.5 Hz, 1H), 1.56 (d, J = 6.5 Hz, 6H). |
| 74 | 11.63 (s, 1H), 8.27 (s, 1H), 7.47 (dd, J = 4.73, 8.78 Hz, 1H), 7.38 (dd, J = 2.55, 9.91 Hz, 1H), 7.03 (br s, 2H), 7.01 (ddd, J = 2.61, 8.84, 9.66 Hz, 1H), 6.82 (dd, J = 0.84, 2.10 Hz, 1H), 1.79 (s, 9H). |
| 75 | 11.96-11.88 (m, 1H), 8.30 (s, 1H), 7.47 (d, J = 7.37 Hz, 1H), 7.23-7.09 (m, 4H), 6.81 (d, J = 2.17 Hz, 1H), 1.80 (s, 9H). |
| 78 | 12.45 (br, 1H), 8.38 (d, J = 4.8 Hz, 1H), 8.27 (s, 1H), 8.02 (d, J = 7.9 Hz, 1H), 7.25 (dd, J = 7.9, 4.8 Hz, 1H), 7.11 (br, 2H), 5.57-5.51 (m, 1H), 4.17-4.07 (overlapping m, 2H), 3.98 (dd, J = 9.1, 4.4 Hz, 1H), 3.94-3.89 (m, 1H), 2.46-2.41 (m, 2H). |
| 79 | 8.33 (dd, J = 4.8, 1.6 Hz, 1H), 8.23 (s, 1H), 7.96 (dd, J = 7.9, 1.6 Hz, 1H), 7.41 (br, 2H), 7.18 (dd, J = 7.9, 4.8 Hz, 1H), 5.27 (app pent, 1H), 2.17-2.02 (overlapping m, 4H), 1.98-1.88 (over-lapping m, 2H), 1.75-1.65 (over-lapping m, 2H). Azaindole NH not observed. |
| 80 | 12.37 (br, 1H), 8.36 (dd, J = 4.8, 1.6 Hz, 1H), 8.26 (s, 1H), 7.99 (dd, J = 7.9, 1.6 Hz, 1H), 7.22 (dd, J = 7.9, 4.8 Hz, 1H), 7.20 (br, 2H), 4.41 (t, J = 7.2 Hz, 2H), 1.78 (q, J = 7.2 Hz, 2H), 1.53 (hept, J = 6.7 Hz, 1H), 0.93 (d, J = 6.7 Hz, 6H). |
| 81 | 12.48 (br, 1H), 8.35 (br d, 1H), 8.25 (s, 1H), 7.97 (br d, 1H), 7.20 (m, 1H), 4.20 (s, 2H), 0.99 (s, 9H). NH₂ not observed. |
| 82 | 8.33 (br, 1H), 8.24 (s, 1H), 7.96 (br d, J = 7.7 Hz, 1H), 7.40 (br, 2H), 7.17 (br, 1H), 4.34 (t, J = 6.9 Hz, 2H), 1.89 (sext, J = 7.2 Hz, 2H), 0.88 (t, J = 7.4 Hz, 3H). Indole NH not observed. |
| 83 | 11.98 (s, 1H), 8.27 (s, 1H), 7.49 (dd, J = 4.41, 8.92 Hz, 1H), 7.30 (dd, J = 2.52, 9.32 Hz, 1H), 7.13 (td, J = 2.55, 9.28 Hz, 1H), 6.94 (br s, 2H), 1.78 (s, 9H). |
| 84 | 11.40 (s, 1H), 8.26 (s, 1H), 7.40 (s, 1H), 7.37 (d, J = 8.17 Hz, 1H), 7.01 (br s, 2H), 7.00 (dd, J = 1.40, 8.37 Hz, 1H), 6.73 (d, J = 1.16 Hz, 1H), 2.39 (s, 3H), 1.79 (s, 9H). |
| 85 | 11.89 (s, 1H), 8.28 (s, 1H), 7.58 (app d, 1H), 7.49 (app dt, 1H), 7.28 (ddd, 1H), 7.19 (ddd,1H), 4.31 (d, J = 7.1 Hz, 2H), 3.85-3.81 (m, 2H), 3.26 (td, 2H), 2.25-2.19 (m, 1H), 1.51-1.41 (m, 2H), 1.37-1.27 (m, 2H). NH₂ signals not observed. |
| 86 | 11.88 (s, 1H), 8.28 (s, 1H), 7.58 (app d, 1H), 7.50 (app dt, 1H), 7.28 (ddd, J = 7.1, 1.2 Hz, 1H), 7.19 (ddd, J = 7.1, 1.0 Hz, 1H), 5.58-5.52 (m, 1H), 4.17-4.07 (overlapping m, 2H), 3.99 (dd, J = 9.2, 4.4 Hz, 1H), 3.94-3.89 (m, 1H), 2.47-2.41 (m, 2H). NH₂ signals not observed. |

Synthesis of Other Examples

Example 19—(2-(4-Amino-1-(tert-butyl)-1H-pyrazolo[3,4-d]pyrimidin-3-yl)-3-chloro-1H-indol-6-yl)methanol To a solution of methyl 2-(4-amino-1-(tert-butyl)-1H-pyrazolo[3,4-d]pyrimidin-3-yl)-3-chloro-1H-indole-6-carboxylate (500 mg, 1.25 mmol) in THF (12 mL) at 0° C. was added LiAlH$_4$ (2.0 M in THF, 2.19 mL). The resulting mixture was warmed to room temperature, maintained at this temperature for 45 min, then recooled to 0° C. NaOH (2.0 M, 20 mL) and water (20 mL) were added, the mixture was warmed to room temperature and stirred for 15 min. EtOAc (20 mL) was added and the biphasic mixture separated. The aq layer was extracted with further EtOAc (2×20 mL) and the combined organic extracts dried and concentrated in vacuo. The crude product was purified by fcc (0-5% MeOH in DCM) to return the title compound (346 mg, 75% yield) as an off-white solid. LCMS [M+H]$^+$ 371; $^1$H NMR δ 11.79 (s, 1H), 8.26 (s, 1H), 7.50 (d, J=8.0 Hz, 1H), 7.44 (dd, J=1.4, 0.8 Hz, 1H), 7.14 (dd, J=8.0, 1.4 Hz, 1H), 7.00-6.61 (br, 2H), 5.21 (t, J=5.8 Hz, 1H), 4.63 (d, J=5.8 Hz, 2H), 1.78 (s, 9H).

Example 25—1-(tert-Butyl)-3-(3-chloro-6-((methylamino)methyl)-1H-indol-2-yl)-1H-pyrazolo[3,4-d]pyrimidin-4-amine A solution of 2-(4-amino-1-(tert-butyl)-1H-pyrazolo[3,4-d]pyrimidin-3-yl)-3-chloro-1H-indole-6-carbaldehyde (59 mg, 0.16 mmol) and methanamine (33 wt % in EtOH, 60 μL, 0.48 mmol) in MeOH (1.5 mL) was stirred at room temperature for 3 h then concentrated in vacuo. The resulting residue was taken up into MeOH (1.5 mL), treated with NaBH$_4$ (6.1 mg, 0.16 mmol) and stirred for a further 18 h. Water (10 mL) was added and the mixture concentrated in vacuo, then partitioned between EtOAc (10 mL) and NaOH (1.0 M, 10 mL). The biphasic mixture was separated and the aq layer extracted with further EtOAc (2×10 mL). The combined organic extracts were dried, concentrated in vacuo and the crude product purified by preparative HPLC to return the title compound (4 mg, 7% yield) as a yellow solid. LCMS [M+H]$^+$ 384; $^1$H NMR (400 MHz, DMSO-d$_6$) δ 8.30 (s, 1H), 8.26 (s, 1H), 7.52 (d, J=8.2 Hz, 1H), 7.47 (s, 1H), 7.18 (d, J=8.2 Hz, 1H), 3.90 (s, 2H), 2.37 (s, 3H), 1.78 (s, 9H). Indole NH and NH$_2$ signals not present.

Example 26—1-(tert-Butyl)-3-(3-chloro-6-(methoxymethyl)-1H-indol-2-yl)-1H-pyrazolo[3,4-d]pyrimidin-4-amine To a solution of (2-(4-amino-1-(tert-butyl)-1H-pyrazolo[3,4-d]pyrimidin-3-yl)-3-chloro-1H-indol-6-yl)methanol (80 mg, 0.19 mmoL) in MeOH (3 mL) was added HCl (4.0 M in 1,4-dioxane, 49 μL). The resulting mixture was heated at 60° C. for 20 h, then cooled to room temperature and partitioned between EtOAc (25 mL) and sat aq NaHCO$_3$ (20 mL). The organic layer was separated, washed with further sat aq NaHCO$_3$ (20 mL), brine (20 mL) then dried and concentrated in vacuo. The crude product was purified by fcc (5-100% EtOAc in isohexane). The solid that was isolated was dissolved in EtOAc (1 mL) and precipitated through the slow addition of isohexane (6 mL). This material was filtered, washed with isohexane (5 mL) and further purified by fcc (0-100% EtOAc in isohexane) to return the title compound (74 mg, quant) as a white solid. LCMS [M+H]$^+$ 385; $^1$H NMR (400 MHz, DMSO-d$_6$) δ 11.84 (s, 1H), 8.26 (s, 1H), 7.54 (app d, J=8.2 Hz, 1H), 7.42 (app s, 1H), 7.15 (dd, J=8.2, 1.4 Hz, 1H), 7.05-6.65 (br, 2H), 4.54 (s, 2H), 3.31 (s, obscured by solvent, assume 3H), 1.78 (s, 9H).

Example 34—3-(3-Bromo-1H-pyrrolo[2,3-b]pyridin-2-yl)-1-(tert-butyl)-1H-pyrazolo[3,4-d]pyrimidin-4-amine To a suspension of 1-tert-butyl-3-(1H-pyrrolo[2,3-b]pyridin-2-yl)pyrazolo[3,4-d]pyrimidin-4-amine (45 mg, 0.14 mmol) in DMF (2 mL) was added NBS (28 mg, 0.15 mmol). The resulting mixture was stirred at room temperature for 2 h then concentrated in vacuo. The crude product was purified by fcc (0-10% MeOH/NH$_3$ (0.7 M) in DCM) to return the title compound (23 mg, 46% yield) as a cream coloured solid. LCMS [M+H]$^+$ 386 and 388; $^1$H NMR (400 MHz, DMSO-d$_6$) δ 12.51 (br, 1H), 8.35 (app d, 1H), 8.25 (s, 1H), 7.92 (dd, J=7.9, 1.6 Hz, 1H), 7.24 (dd, J=7.9, 4.7 Hz, 1H), 6.95 (br, 2H), 1.78 (s, 9H).

Example 35—3-(6-(Aminomethyl)-3-chloro-1H-indol-2-yl)-1-(tert-butyl)-1H-pyrazolo[3,4-d]pyrimidin-4-amine To a solution of 2-(4-amino-1-(tert-butyl)-1H-pyrazolo[3,4-d]pyrimidin-3-yl)-3-chloro-1H-indole-6-carbonitrile (280 mg, 0.765 mmol) in THF (7.5 mL) at room temperature was added LiAlH$_4$ (2.0 M in THF, 0.765 mL) and the resulting mixture heated at 50° C. for 2 h then cooled to 0° C. Aq NaOH (2.0 M, 10 mL) and water (10 mL) were added and the mixture stirred at room temperature for 15 min. EtOAc (10 mL) was then added and the biphasic mixture separated. The aq layer was extracted with further EtOAc (2×10 mL) and the combined organic extracts dried and concentrated in vacuo. An aliquot (49 mg) of the crude product was purified by preparative HPLC to return the title compound (8 mg) as a white solid. LCMS [M+H]$^+$ 370; $^1$H NMR (400 MHz, DMSO-d$_6$) δ8.38 (s, 1H), 8.26 (s, 1H), 7.54-7.52 (overlapping d and s, 2H), 7.21 (br dd, 1H), 7.04 (br, 2H), 4.02 (s, 2H), 3.80-3.50 (brs, 2H), 1.78 (s, 9H).

Example 38—1-(4-Aminocyclohexyl)-3-(3-chloro-1H-pyrrolo[2,3-b]pyridin-2-yl)pyrazolo[3,4-d]pyrimidin-4-amine Dihydrochloride To a thin suspension of tert-butyl N-[4-[4-amino-3-(3-chloro-1H-pyrrolo[2,3-b]pyridin-2-yl)pyrazolo[3,4-d]pyrimidin-1-yl]cyclohexyl]carbamate (16 mg, 0.03 mmol) in THF (0.20 mL) was added HCl (4M in 1,4-dioxane, 0.17 mL, 0.66 mmol) dropwise. The reaction was stirred for 40 min then further HCl (4M in 1,4-dioxane, 0.17 mL, 0.66 mmol) was added. The reaction was stirred for 6 h then concentrated to give the title compound (18 mg, quant) as a light yellow powder. LCMS [M-H]$^-$ 381.2; $^1$H NMR (300 MHz, DMSO-d$_6$) δ 8.52 (s, 1H), 8.44-8.35 (m, 1H), 8.11 (br s, 3H), 7.28 (dd, J=5.03, 7.88 Hz, 1H), 4.96 (br s, 2H), 3.33 (s, 1H), 2.36-2.24 (m, 3H), 2.02 (s, 4H), 1.99-1.88 (m, 2H). Azaindole NH not visible.

Example 49—3-(3-Bromo-1H-indol-2-yl)-1-(tert-butyl)-1H-pyrazolo[3,4-d]pyrimidin-4-amine To a solution of 1-tert-butyl-3-(1H-indol-2-yl)pyrazolo[3,4-d]pyrimidin-4-amine (110 mg, 0.338 mmol) in DMF (2 mL) was added NBS (67.0 mg, 0.371 mmol) and the resulting mixture stirred at room temperature for 2 h. DIPEA (120 μL, 0.680 mmol) was added, the mixture was heated at 50° C. for 2 h then cooled to room temperature, concentrated in vacuo and purified by fcc (50% EtOAc in isohexane) to return the title compound (9 mg, 7% yield) as a pink solid. LCMS [M+H]$^+$ 385 and 387; $^1$H NMR (400 MHz, DMSO-d$_6$) δ11.97 (s, 1H), 8.27 (s, 1H), 7.50 (br t, 2H), 7.27 (ddd, J=8.2, 7.0, 1.3 Hz, 1H), 7.20 (ddd, J=8.0, 7.0, 1.1 Hz, 1H), 1.78 (s, 9H). NH$_2$ signals not observed.

Example 52—2-(2-(4-Amino-1-(tert-butyl)-1H-pyrazolo[3,4-d]pyrimidin-3-yl)-3-chloro-1H-indol-6-yl) propan-2-ol To a solution of methyl 2-(4-amino-1-(tert-butyl)-1H-pyrazolo[3,4-d]pyrimidin-3-yl)-3-chloro-1H-indole-6-carboxylate (75 mg, 0.19 mmol) in THF (2 mL) at 0° C. was added MeLi (1.6 M in Et$_2$O, 0.59 mL). The resulting mixture stirred for 10 min and then diluted with sat aq NH$_4$Cl (5 mL), EtOAc (10 mL) and water (5 mL). This mixture was passed through a phase separator and the organic extracts concentrated in vacuo. The crude product was purified by fcc (50-100% EtOAc in isohexane) to return the title compound (46 mg, 61% yield) as a pale yellow glass. LCMS [M+H]$^+$ 399; $^1$H NMR (400 MHz, DMSO-d$_6$) δ11.73 (s, 1H), 8.26 (s, 1H), 7.60 (dd, J=1.5, 0.7 Hz, 1H), 7.47 (d, J=8.4 Hz, 1H), 7.28 (dd, J=8.4, 1.5 Hz, 1H), 7.06-6.64 (br, 2H), 5.06 (s, 1H), 1.78 (s, 9H), 1.49 (s, 6H).

Example 72—1-(tert-Butyl)-3-(3-chloro-6-((dimethylamino)methyl)-1H-indol-2-yl)-1H-pyrazolo[3,4-d]pyrimidin-4-amine To a solution of 2-(4-amino-1-tert-butyl-pyrazolo[3,4-d]pyrimidin-3-yl)-3-chloro-N,N-dimethyl-1H-indole-6-carboxamide (68 mg, 0.14 mmol) in THF (3 mL) at 0° C. was added LiAlH$_4$ (2.0 M in THF, 0.25 mL) dropwise. The resulting mixture was warmed to room temperature and stirred for 1 h, then cooled to back to 0° C. and quenched through the dropwise addition of aq NaOH (2.0 M, 3 mL). After stirring for 10 min, water (5 mL) and EtOAc (20 mL) were added and the layers separated. The aq layer was extracted with further EtOAc (2×20 mL) and the combined organic extracts washed with brine (3×10 mL), dried and concentrated in vacuo. The crude product was purified by fcc (0-10% [0.7 M NH$_3$ in MeOH] in DCM) to return the title compound (19 mg, 34% yield) as a white solid. LCMS [M+H]$^+$ 398; $^1$H NMR (400 MHz, DMSO-d$_6$) δ11.76 (br s, 1H), 8.26 (s, 1H), 7.49 (d, J=8.2 Hz, 1H), 7.37 (app s, 1H), 7.13 (dd, J=8.2, 1.4 Hz, 1H), 6.88 (br, 2H), 3.50 (s, 2H), 2.17 (s, 6H), 1.78 (s, 9H).

Example 76—1-(tert-Butyl)-3-(3-fluoro-1H-indol-2-yl)-1H-pyrazolo[3,4-d]pyrimidin-4-amine To a solution of 1-tert-butyl-3-(1H-indol-2-yl)pyrazolo[3,4-d]pyrimidin-4-amine (42 mg, 0.13 mmol) in MeCN (3 mL) was added Selectfluor® (50 mg, 0.13 mmol) and the resulting mixture stirred at room temperature for 20 min. Sat aq NaHCO$_3$ (2 mL) was added, the mixture stirred for 15 min and then diluted with EtOAc (20 mL). The organic layer was separated and retained and the aq phase was extracted with further EtOAc (20 mL). The combined organic extracts were washed with further sat aq NaHCO$_3$ (5 mL), water (2×5 mL), brine (10 mL), dried and concentrated in vacuo. The crude product was purified by fcc (0-10% MeOH/NH$_3$ (0.7 M) in DCM). The resulting solid was further purified by preparative HPLC to return the title compound (5 mg, 91% pure by HPLC, 12% yield) as a green solid. LCMS [M+H]$^+$ 325; $^1$H NMR (400 MHz, DMSO-d$_6$) δ 11.37 (br, 1H), 8.24 (s, 1H), 7.59 (d, J=8.1 Hz, 1H), 7.43 (br dd, J=8.2, 2.3 Hz, 1H), 7.25-6.89 (br, 2H), 7.22 (app t, 1H), 7.11 (app t, 1H), 1.78 (s, 9H).

Example 77—3-(3-Chloro-1H-pyrrolo[2,3-b]pyridin-2-yl)-1-(2-(4-(dimethylamino)piperidin-1-yl) ethyl)-1H-pyrazolo[3,4-d]pyrimidin-4-amine To a solution of 2-(4-amino-3-(3-chloro-1H-pyrrolo[2,3-b]pyridin-2-yl)-1H-pyrazolo[3,4-d] pyrimidin-1-yl)acetaldehyde trifluoroacetate (224 mg, 0.304 mmol) in THF (15 mL) was added acetic acid (23.3 μL, 0.407 mmol) and N,N-dimethylpiperidin-4-amine (57.4 μL, 0.407 mmol). The resulting mixture was stirred at room temperature for 15 min, then NaBH(OAc)$_3$ (104 mg, 0.489 mmol) was added and the mixture maintained at room temperature for a further 19 h. EtOAc (20 mL) and sat aq NaHCO$_3$ (30 mL) were added and the biphasic mixture separated. The organic extracts were washed with brine (20 mL), dried and concentrated in vacuo. The crude product was purified by preparative HPLC to return the title compound (2 mg, 91% pure by HPLC, 2% yield) as a yellow solid. LCMS [M+H]$^+$ 440; $^1$H NMR (400 MHz, DMSO-d$_6$) δ8.33 (dd, J=4.7, 1.6 Hz, 1H), 8.25 (s, 1H), 7.97 (dd, J=7.9, 1.6 Hz, 1H), 7.43 (br, 2H), 7.19 (dd, J=7.9, 4.7 Hz, 1H), 4.47 (t, J=6.6 Hz, 2H), 2.96 (app d, 2H), 2.81 (t, J=6.6 Hz, 2H), 2.19 (m, 6H), 2.14-2.08 (m, 1H) 1.98 (br t, 2H), 1.69 (br d, 2H), 1.34-1.24 (m, 2H). NH of azaindole not observed.

Example 87—3-(3-Chloro-1H-pyrrolo[2,3-b]pyridin-2-yl)-1-(2-(piperidin-1-yl)ethyl)-1H-pyrazolo[3,4-d]pyrimidin-4-amine Prepared according to a similar procedure to that used for 3-(3-chloro-1H-pyrrolo[2,3-b]pyridin-2-yl)-1-(2-(4-(dimethylamino)piperidin-1-yl)ethyl)-1H-pyrazolo[3,4-d]pyrimidin-4-amine from 2-(4-amino-3-(3-chloro-1H-pyrrolo [2,3-b]pyridin-2-yl)-1H-pyrazolo[3,4-d]pyrimidin-1-yl) acetaldehyde trifluoroacetate (230 mg, 0.266 mmol) and piperidine (52.5 μL, 0.531 mmol) for a reaction time of 18 h and purified by fcc (0-100% MeOH in DCM) to return the title compound (4 mg, 4% yield) as a yellow solid. LCMS [M+H]$^+$ 397; $^1$H NMR (400 MHz, DMSO-d$_6$) δ12.50 (br, 1H), 8.35 (dd, J=4.7, 1.6 Hz, 1H), 8.26 (s, 1H), 7.98 (dd, J=7.9, 1.6 Hz, 1H), 7.58-6.99 (br, 2H), 7.20 (dd, J=7.9, 4.7 Hz, 1H), 4.48 (t, J=6.7 Hz, 2H), 2.79 (t, J=6.7 Hz, 2H), 2.42 (br t, 4H), 1.45-1.40 (over-lapping m, 4H), 1.38-1.29 (m, 2H).

Example 88—2-(4-Amino-1-(tert-butyl)-1H-pyrazolo[3,4-d]pyrimidin-3-yl)-3-chloro-1H-pyrrolo[2,3-b] pyridine-6-carbonitrile A mixture of 3-bromo-1-tert-butyl-pyrazolo[3,4-d]pyrimidin-4-amine (450 mg, 1.38 mmol), tert-butyl 6-cyano-2-tributylstannyl-pyrrolo[2,3-b]pyridine-1-carboxylate (1.16 g, 1.96 mmol), Pd(PPh$_3$)$_4$ (190 mg, 0.164 mmol) and CuI (63.0 mg, 0.331 mmol) were degassed with nitrogen, dissolved in 1,4-dioxane (10 mL) and heated at 90° C. for 6.5 h. The crude mixture was then cooled to room temperature, diluted with EtOAc (30 mL) and passed through a pad of celite, washing with further EtOAc (150 mL). The resulting solution was concentrated in vacuo and purified by fcc (0-50% EtOAc in isohexane). The brown solid that was obtained was taken up into DCM (1 mL), treated with TFA (1.00 mL, 13.0 mmol) and stirred at room temperature for 2 h. DCM (20 mL) and sat aq NaHCO$_3$ (30 mL) were added and the biphasic mixture passed through a phase separator. The resulting organic extracts were concentrated in vacuo and purified by fcc (0-2% MeOH/NH$_3$ (0.7 M) in DCM) to return the title compound (6 mg, 94% pure by $^1$H NMR, 1% yield) as a beige solid. LCMS [M+H]$^+$ 333; $^1$H NMR (400 MHz, DMSO-d$_6$) δ12.69 (s, 1H), 8.28 (s, 1H), 8.23 (d, J=8.0 Hz, 1H), 7.68 (d, J=8.0 Hz, 1H), 7.10 (br, 2H), 6.96 (s, 1H), 1.79 (s, 9H).

Biological Data

RET and KDR Enzyme Assays

Kinase activity was detected using CisBio HTRF kinEASE kit based on time-resolved fluorescence transfer (FRET). The assay was performed in 384-well white plates (Corning #3574) in a reaction volume of 10 μL containing 1×CisBio enzymatic buffer supplemented with a final concentration of 5 mM MgCl$_2$, 1 mM DTT, 10 nM SEB and 0.01% Triton X100 for RET. The same buffer was used for the KDR biochemical assay with the addition of 2 mM MnCl$_2$.

Inhibitors were pre-incubated in the plate for 15 mins with 5 μL kinase and assay buffer at the following concentrations; 13 pM RET (Carna Biosciences; 08-159) and 150 pM KDR (Millipore; 14-630). The reaction was initiated by the addition of 5 μL ATP and substrate at 2× final reaction concentrations. For RET, this was 18 μM and 2 μM; for KDR, this was 16 μM and 1 μM, respectively. Reactions were performed at ATP K$_m$ for each target. The assay was allowed to proceed at room temperature for 20 mins before terminating with the addition of 10 μL HTRF detection buffer containing EDTA supplemented with TK-antibody labelled with Eu$^{3+}$-Cryptate (1:100 dilution) and streptavidin-XL665 (128 nM). Following incubation at room temperature for 1 hour, FRET signal was measured using the Pherastar FS Microplate Reader.

Activity data (IC$_{50}$) for the compounds of the present invention against RET and KDR enzymes is shown in Table 1 below.

TABLE 1

RET and KDR enzyme activity data

| Example | RET Enzyme IC$_{50}$ (μM) | KDR Enzyme IC$_{50}$ (μM) | RET$^{V804M}$ Enzyme IC$_{50}$ (μM) |
|---|---|---|---|
| 1 | 0.0612 | 26 | 2.02 |
| 2 | 0.117 | >30 | 6.66 |
| 3 | 0.257 | >30 | 0.31 |
| 4 | 0.104 | >30 | 0.315 |
| 5 | 0.0285 | 13.2 | 2.63 |
| 6 | 0.0265 | 9.06 | 2.57 |
| 7 | 0.0253 | 26.1 | 0.188 |
| 8 | 0.0340 | 17.3 | 0.129 |
| 9 | 0.0007 | 0.142 | 0.179 |
| 10 | 0.0007 | 0.144 | 0.00844 |
| 11 | 0.0307 | 8.53 | 3.97 |
| 12 | 0.0822 | >30 | 0.905 |
| 13 | 0.0086 | 3 | 3 |
| 14 | 0.1130 | >30 | |
| 15 | 0.0586 | >30 | >30 |
| 16 | 0.1860 | >30 | >30 |
| 17 | 0.0294 | >30 | 5.3 |
| 18 | 0.0069 | 9.49 | 0.0775 |
| 19 | 0.0036 | 5.05 | 0.0982 |
| 20 | 5.4200 | >30 | 29.4 |
| 21 | 0.0003 | 0.025 | 0.0354 |
| 22 | 0.0090 | 9.49 | 3 |
| 23 | 0.0043 | 8.64 | 0.0602 |
| 24 | 1.7400 | >30 | 21.9 |
| 25 | 0.0936 | 5.19 | 1.03 |
| 26 | 0.0219 | >30 | 0.0887 |
| 27 | 0.0166 | >30 | >30 |
| 28 | 0.0261 | >30 | 6.98 |
| 29 | 0.0068 | >30 | 0.0469 |
| 30 | 0.0103 | 6.35 | 0.137 |
| 31 | 0.1010 | >30 | >30 |
| 32 | 0.0035 | 0.21 | 0.621 |
| 33 | 0.0029 | 0.584 | 0.0439 |
| 34 | 0.0018 | 2.15 | 0.0289 |
| 35 | 0.0945 | 1.68 | 1.35 |
| 36 | 0.0064 | >30 | |
| 37 | 0.0031 | | |
| 38 | 0.0013 | 0.117 | 0.0244 |
| 39 | 0.0429 | 21 | 14.9 |
| 40 | 0.0040 | 0.734 | |
| 41 | 0.0231 | >30 | |
| 42 | 0.0025 | 1.75 | |
| 43 | 0.0210 | 3.97 | |
| 44 | 0.0187 | 4.57 | 1.87 |
| 45 | 0.0011 | 1.52 | 0.0261 |
| 46 | 0.0044 | 6.4 | 0.0981 |
| 47 | 0.0050 | 3.33 | 1.67 |
| 48 | 0.0501 | 27.1 | 1.22 |
| 49 | 0.1760 | >30 | 2.58 |
| 50 | 0.0020 | 1.41 | 4.6 |
| 51 | 0.0192 | 5.24 | 0.123 |
| 52 | 0.4820 | >30 | 2.18 |
| 53 | 0.4240 | >30 | >30 |
| 54 | 0.5300 | >30 | >30 |
| 55 | 0.0017 | | 0.0462 |
| 56 | 0.0089 | >30 | 0.157 |
| 57 | 0.2550 | >30 | >30 |
| 58 | 0.0444 | >30 | 1.2 |
| 59 | 0.0285 | >30 | 0.343 |
| 60 | 0.0241 | >30 | 0.735 |
| 61 | 0.0080 | 29.6 | 0.124 |
| 62 | 0.0027 | >30 | 0.0392 |
| 63 | 0.3690 | >30 | 3.25 |
| 64 | 0.0623 | 15.1 | 0.226 |
| 65 | >30 | >30 | >30 |
| 66 | 0.0034 | 1.87 | 0.0323 |
| 67 | >30 | >30 | >30 |
| 68 | 0.0020 | 11.4 | 0.0319 |
| 69 | 0.0012 | 0.657 | 0.0191 |
| 70 | 3.0500 | >30 | >30 |
| 71 | 2.0800 | >30 | 22 |
| 72 | 0.2570 | >30 | 1.13 |
| 73 | 0.0026 | 0.466 | 0.627 |
| 74 | 0.0490 | >30 | >30 |
| 75 | 0.1570 | >30 | 10.9 |
| 76 | 0.0339 | 7.32 | 0.13 |
| 77 | 0.1870 | >30 | 5.71 |
| 78 | 0.0045 | 1.87 | 0.0688 |
| 79 | 0.0016 | 1.29 | 0.0285 |
| 80 | 0.0316 | >30 | 0.41 |
| 81 | 0.0424 | >30 | 0.29 |
| 82 | 0.0119 | >30 | 0.0951 |
| 83 | 0.1030 | >30 | 1.36 |
| 84 | 0.0618 | 3.37 | 11.4 |
| 85 | 0.4710 | >30 | 5.34 |
| 86 | 0.0442 | 17.1 | 0.6 |
| 87 | 0.3090 | >30 | >30 |
| 88 | 0.0040 | 5.48 | 0.5 |

BaF3 Cell Assay

The system originally developed by Daley and Baltimore[16] was used, whereby IL3-dependent BaF3 cells are modified to express an activated recombinant kinase. Following removal of IL3, the modified cells are dependent on the activity of the recombinant kinase for survival and proliferation. The BaF3 cell lines, expressing KIF5B-RET (gift from Pasi Janne[7]) and KDR (Advanced Cellular Dynamics, San Diego) were maintained in RPMI-1640 media containing 10% FBS and appropriate antibiotics. Non-modified BaF3 cells (WT) were maintained in RPMI-1640 media containing 10% FBS and supplemented with 10 ng/mL recombinant mouse IL3 (R&D systems). For assessment of compound $IC_{50}$, cells were plated into 384-well plates at 1500 or 3000 cells per well in 30 µL culture medium and compounds dispensed using an acoustic liquid handling platform (LABCYTE). Following incubation of the cells for 48 hours at 37° C. in a humidified 5% $CO_2$ atmosphere, viability was determined by addition of 10 µL CellTiter-Glo reagent (Promega) and measurement of luminescence.

Cell activity data is presented in Table 2 below.

TABLE 2

Cell activity data

| Example | RET Cell IC50 (µM) | KDR Cell IC50 (µM) | $RET^{V804M}$ Cell $IC_{50}$ (µM) | BaF3 $IC_{50}$ (µM) |
|---|---|---|---|---|
| 1 | 0.0989 | 4.88 | 1.88 | 2.19 |
| 2 | 0.139 | 1.17 | 1.24 | 0.85 |
| 3 | 0.1 | 6.38 | 0.458 | 7.2 |
| 4 | 0.301 | 6.94 | 0.997 | 7.74 |
| 5 | 0.102 | 0.814 | 0.592 | 0.799 |
| 6 | 0.137 | 1.61 | 1.14 | 1.58 |
| 7 | 0.128 | 4.87 | 0.341 | 6.04 |
| 8 | 0.238 | 4.79 | 0.641 | 9.19 |
| 9 | 0.0419 | 0.692 | 1.36 | 3.8 |
| 10 | 0.0113 | 0.541 | 0.0629 | >10 |
| 11 | 0.558 | 3.61 | 2.91 | 6.33 |
| 12 | 0.809 | 1.55 | 1.4 | 4.8 |
| 13 | 0.107 | 2.19 | 1.49 | 5.07 |
| 14 | 0.559 | 8.47 | 1.19 | >10 |
| 15 | 0.231 | >10 | 1.36 | >10 |
| 16 | 0.283 | >10 | 0.796 | >10 |
| 17 | 0.103 | >10 | 9.17 | >10 |
| 18 | 0.0652 | >10 | 0.202 | >10 |
| 19 | 0.0363 | 6.73 | 0.173 | >10 |
| 20 | 0.561 | >10 | 2.95 | >10 |
| 21 | 0.0144 | 0.318 | 0.462 | 2.51 |
| 22 | 0.619 | >10 | 3.49 | >10 |
| 23 | 0.204 | >10 | 1.36 | >10 |
| 24 | 0.746 | >10 | 1.29 | >10 |
| 25 | 0.61 | 6.36 | 1.42 | 5.29 |
| 26 | 0.0498 | 8.24 | 0.0887 | >10 |
| 27 | 0.124 | 6.95 | 0.627 | 9.06 |
| 28 | 0.101 | 6.46 | 0.317 | 4.53 |
| 29 | 0.0617 | 7.74 | 0.16 | >10 |
| 30 | 0.0613 | 9.31 | 0.307 | >10 |
| 31 | 2.19 | >10 | 6.15 | >10 |
| 32 | 0.0911 | 0.885 | 1.22 | 8.57 |
| 33 | 0.0844 | 1.57 | 0.43 | 7.26 |
| 34 | 0.0257 | 0.709 | 0.345 | 3.59 |
| 35 | 0.202 | >10 | 0.751 | >10 |
| 36 | 0.0996 | >10 | 0.353 | 4.08 |
| 37 | 0.0702 | 1.37 | 1.11 | 4.01 |
| 38 | 0.0525 | 1.47 | 0.762 | 1.3 |
| 39 | 0.153 | 2.88 | 1.01 | 3.03 |
| 40 | 0.11 | 1.96 | 1.43 | 3.16 |
| 41 | 0.139 | 5.87 | 1.6 | >10 |
| 42 | 0.0756 | 0.837 | 1.15 | 4.79 |
| 43 | 0.294 | 4.35 | 3.99 | 9.5 |
| 44 | 0.0836 | 2.77 | 1.47 | 3.63 |
| 45 | 0.0158 | 0.552 | 0.0966 | 2.24 |
| 46 | 0.0949 | 6.18 | 0.738 | >10 |
| 47 | 0.0577 | 2.33 | 1.19 | 4.09 |
| 48 | 0.231 | >10 | 0.762 | >10 |
| 49 | 0.138 | 5.38 | 1.41 | 9.18 |
| 50 | 0.0506 | 0.522 | 3.92 | >10 |
| 51 | 0.0403 | 0.758 | 0.452 | 2.24 |

TABLE 2-continued

Cell activity data

| Example | RET Cell IC50 (µM) | KDR Cell IC50 (µM) | $RET^{V804M}$ Cell $IC_{50}$ (µM) | BaF3 $IC_{50}$ (µM) |
|---|---|---|---|---|
| 52 | 0.322 | >10 | 0.695 | >10 |
| 53 | 0.542 | >10 | 3.95 | >10 |
| 54 | 1.06 | >10 | 4.17 | >10 |
| 55 | 0.036 | 1.8 | 0.203 | 3.16 |
| 56 | 0.148 | >10 | 1.32 | >10 |
| 57 | 2.38 | >10 | 5.46 | >10 |
| 58 | 5.51 | >10 | >10 | >10 |
| 59 | 0.518 | >10 | 2.08 | >10 |
| 60 | 0.477 | >10 | 1.81 | >10 |
| 61 | 0.12 | >10 | 0.919 | >10 |
| 62 | 0.0678 | 8.48 | 0.44 | >10 |
| 63 | 0.353 | >10 | 1.16 | >10 |
| 64 | 0.0962 | >10 | 0.303 | >10 |
| 65 | 1.01 | >10 | 3.85 | >10 |
| 66 | 0.0436 | 1.31 | 0.195 | 2.15 |
| 67 | 0.0687 | 3.03 | 0.335 | 3.16 |
| 68 | 0.067 | 9.33 | 0.569 | >10 |
| 69 | 0.0409 | 1.64 | 0.299 | 3.16 |
| 70 | 0.396 | >10 | 3.17 | >10 |
| 71 | 0.278 | >10 | 0.735 | >10 |
| 72 | 1.32 | 5.19 | 1.57 | 5.16 |
| 73 | 0.0562 | 0.439 | 2.87 | >10 |
| 74 | 0.0731 | 3.62 | 1.96 | 5 |
| 75 | 0.609 | >10 | 4.38 | 5.34 |
| 76 | 0.103 | 7.56 | 1.44 | 5.48 |
| 77 | 7.62 | >10 | >10 | >10 |
| 78 | 0.106 | 5.78 | 0.798 | >10 |
| 79 | 0.0443 | 1.91 | 0.18 | >10 |
| 80 | 0.309 | >10 | 1.26 | 8.5 |
| 81 | 0.991 | >10 | 5.06 | >10 |
| 82 | 0.151 | >10 | 0.86 | >10 |
| 83 | 0.104 | >10 | 0.946 | >10 |
| 84 | 0.0672 | 1.58 | 1.94 | 6.13 |
| 85 | 1.68 | >10 | 2.33 | >10 |
| 86 | 0.542 | >10 | 1.3 | >10 |
| 87 | 3.35 | >10 | 7.34 | >10 |
| 88 | 0.0251 | >10 | 1.44 | >10 |

While specific embodiments of the invention have been described herein for the purpose of reference and illustration, various modifications will be apparent to a person skilled in the art without departing from the scope of the invention as defined by the appended claims.

REFERENCES

[1] Carlomagno, F., Guida, T., Anagantil, S., Vecchio, G., Fusco, A., Ryan, A., Billaud, M., Santoro, M. (2004). Disease associated mutations at valine 804 in the RET receptor tyrosine kinase confer resistance to selective kinase inhibitors. Oncogene 23, 6056-6063

[2] Chao, B., Briesewitz, R., Villalona-Calero, M. (2012) RET fusion genes in Non-Small-Cell Lung Cancer. JCO 30, 4439-4441.

[3] Dinér, P., Alao, J., Söderland, J., Sunnerhagen, P. Grotli, M. (2012) J Med Chem 2012 55 (10) 4872-6

[4] Elisei, R., Cosci, B., Romei, C., Bottici, V., Renzini, G., Molinaro, E., Agate, L., Vivaldi, A., Faviana, P., Basolo, F., Miccoli, P., Berti, P., Pacini, F., Pinchera, A. (2008) RET genetic screening in patients with medullary thyroid cancer and their relatives: experience with 807 individuals at one center. Journal of Clinical Endocrinology and Metabolism 93, 682-687.

[5] Ju, Y., Lee, W., Shin, J., Lee, S., Bleazard, T., Won, J., Kim, Y., Kim, J., Kang, J., Seo, J. (2011). A transforming KIF5B and RET gene fusion in lung adenocarcinoma revealed from whole-genome and transcriptome sequencing. Genome Res. 3, 436-445.

[6] Kohno, T., Ichikawa, H., Totoki, Y., Yasuda, K., Hiramoto, M., Nammo, T., Sakamoto, H., Tsuta, K., Furuta, K., Shimada, Y., Iwakawa, R., Ogiwara, H., Oike, T., Enari, M., Schetter, A., Okayama, H., Haugen, A., Skaug, V. Chiku, S., Yamanaka, I., Arai, Y., Watanabe, S., Sekine, I., Ogawa, S., Harris, C., Tsuda, H., Yoshida, T., Yokota, J., Shibata, T. (2012) KIF5B-RET fusions in lung adenocarcinoma. Nat Med. 12, 375-377.

[7] Lipson, D., Capelletti, M., Yelensky, R., Otto, G., Parker, A., Jaroszi, M., Curran, J., Balasubramanian, S., Bloom, T., Brennan, K., Donahue, A., Downing, S., Frampton, G., Garcia, L., Juhn, F., Mitchell, K., White, E., White, J., Zwirko, Z., Peretz, T., Nechushtan, H., Soussan-Gutman, L., Kim, J., Sasaki, H., Kim, H., Park, S., Ercan, D., Sheehan, C., Ross, J. Cronin, M., Jänne, P., Stephens, P. (2012) Identification of new ALK and RET gene fusions from colorectal and lung cancer biopsies. Nat Med. 12, 382-384.

[8] Matsubara, D., Kanai, Y., Ishikawa, S., Ohara, S., Yoshimoto, T., Sakatani, T., Oguni, S., Tamura, T., Kataoka, H., Endo, S., Murakami, Y., Aburatani, H., Fukayama, M., Niki, T. (2012). Identification of CCDC6-RET fusion in the human lung adenocarcinoma cell line, LC-2/ad. J Thorac Oncol. 12, 1872-6.

[9] Nagilla, M., Brown, R., Cohen, E. (2012). Cabozantinib for the treatment of Advanced Medullary Thyroid Cancer. Adv Ther 11, 925-934.

[10] Santoro, M. and Carlomagno, F. (2006). Drug insight: Small-molecule inhibitors of protein kinases in the treatment of thyroid cancer. Nature Clinical Practice: Endocrinology and Metabolism 2, 42-52.

[11] Verbeek. H. H., Alves, M. M., de Groot, J. W., Osinga J, Plukker, J. T., Links, T. P., Hofstra, R. M. (2011). The effects of four different tyrosine kinase inhibitors on medullary and papillary thyroid cancer cells. J Clin Endocrinol Metab. 96, 2010-2381.

[12] Vitagliano, D., De Falco, V., Tamburrino, A., Coluzzi, S., Troncone, G., Chiappetta, G., Ciardiello, F., Tortora, G., Fagin, J., Ryan, A., Carlomagno, F., Santoro, (2011). The tyrosine inhibitor ZD6474 blocks proliferation of RET mutant medullary thyroid carcinoma cells. Endocrine-related Cancer 18, 1-11.

[13] Wang, R., Hu, H., Pan, Y., Li, Y., Ye, T., Li, C., Luo, X., Wang, L., Li, H., Zhang, Y., Li, F., Lu, Y., Lu, Q., Xu, J., Garfield, D., Shen, L., Ji, H., Pao, W., Sun, Y., Chen, H. (2012). RET fusions define a unique molecular and clinicopathologic subtype of non-small-cell lung cancer. JCO 30, 4352-4359.

[14] Wells, S. and Santoro, M. (2009) Targeting the RET pathway in thyroid cancer. Clin Can Res. 15, 7119-7123.

[15] Wells, S., Gosnell, J., Gagel, R., Moley, J., Pfister, D., Sosa, J., Skinner, M., Krebs, A., Vasselli, J., Schlumberger, M. (2012). Vandetanib in patients with locally advanced or metastatic medullary thyroid cancer: a randomized, double-blind phase III trial. JCO 10, 134-141.

[16] Daley, G. Q.; Baltimore, D. Transformation of an interleukin 3-dependent hematopoietic cell line by the chronic myelogenous leukemia-specific P210bcr/abl protein. Proc. Natl. Acad. Sci. U.S.A. 1988, 85, 9312-16.

The invention claimed is:
1. A compound of formula Ib:

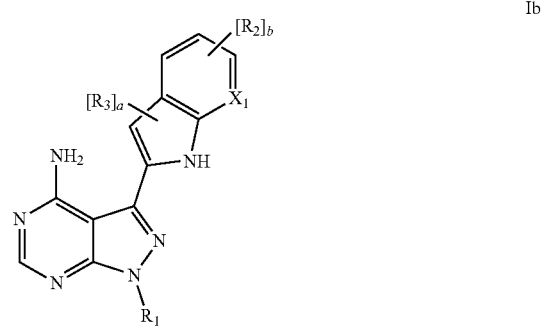

or a pharmaceutically acceptable salt thereof, wherein:
$R_1$ is a group of the formula -L-Y-Q;
L is absent or is (1-5C)alkylene;
Y is absent;
Q is (1-6C)alkyl, phenyl, (3-10C)cycloalkyl, or 4-6-membered heterocyclyl containing 1-3 heteroatoms selected from N and O, each of which is optionally substituted by one or more substituents independently selected from halo, amino, cyano, hydroxy, $NR_cR_d$, $C(O)OR_c$, $N(R_d)C(O)R_c$, and $S(O)_pR_c$;
p is 2;
$R_c$ and Rd are independently hydrogen, (1-6C)alkyl, or (3-6C)cycloalkyl,
or $R_c$ and Rd are taken together with the nitrogen atom to which they are attached to form a 4-7 membered heterocyclic ring optionally substituted by one or more substituents selected from (1-4C)alkyl and halo;
$X_1$ is CH or N;
each $R_2$ is independently halo, (1-4C)alkyl, cyano, C(O)N($R_k$)$R_j$, or $(CH_2)_vNR_jR_k$, wherein (1-4C)alkyl is optionally substituted by one or more substituents selected from (1-4C)alkoxy, amino, $NR_{j1}R_{k1}$, and $OR_{j1}$;
v is 1;
$R_j$ and $R_k$ are each independently hydrogen or (1-4C) alkyl;
$R_{j1}$ and $R_{k1}$ are each independently hydrogen or (1-4C) alkyl;
b is 0, 1, or 2;
$R_3$ is halo; and
a is 1.

2. The compound of claim 1, or a pharmaceutically acceptable salt thereof, wherein L is absent or is (1-3C) alkylene.

3. The compound of claim 1, or a pharmaceutically acceptable salt thereof, wherein Q is (3-6C)alkyl.

4. The compound of claim 1, or a pharmaceutically acceptable salt thereof, wherein:
Q is 4-6-membered heterocyclyl containing 1-3 heteroatoms selected from N and O and optionally substituted by one or more substituents independently selected from halo, amino, hydroxy, $NR_cR_d$, and $S(O)_pR_c$;
p is 2; and
$R_c$ and $R_d$ are independently hydrogen or (1-6C)alkyl.

5. The compound of claim 1, or a pharmaceutically acceptable salt thereof, wherein:
Q is (3-10C)cycloalkyl optionally substituted by one or more substituents independently selected from hydroxy, $NR_cR_d$, and $N(R_d)C(O)R_c$; and $R_c$ and $R_d$ are independently hydrogen, (1-6C)alkyl, or (3-6C)cycloalkyl, or $R_c$ and $R_d$ are taken together with the nitrogen atom to which they are attached to form a 4-7 membered heterocyclic ring.

6. The compound of claim 1, or a pharmaceutically acceptable salt thereof, wherein Q is phenyl optionally substituted by one or more substituents independently selected from halo, amino, and cyano.

7. The compound of claim 1, or a pharmaceutically acceptable salt thereof, wherein $R_1$ is (1-6C)alkyl.

8. The compound of claim 7, or a pharmaceutically acceptable salt thereof, wherein $R_1$ is tert-butyl.

9. The compound of claim 1, or a pharmaceutically acceptable salt thereof, wherein $X_1$ is CH.

10. The compound of claim 1, or a pharmaceutically acceptable salt thereof, wherein $X_1$ is N.

11. The compound of claim 1, or a pharmaceutically acceptable salt thereof, wherein b is 0.

12. The compound of claim 1, or a pharmaceutically acceptable salt thereof, wherein:

$R_2$ is halo, (1-4C)alkyl, cyano, or $(CH_2)_v NR_j R_k$, wherein (1-4C)alkyl is optionally substituted by one or more substituents selected from (1-4C)alkoxy, amino, $NR_{j1}R_{k1}$, and $OR_{j1}$;

v is 1;

$R_j$ and $R_k$ are each independently hydrogen or (1-4C)alkyl;

$R_{j1}$ and $R_{k1}$ are each independently hydrogen or (1-4C)alkyl; and b is 1.

13. The compound of claim 1, or a pharmaceutically acceptable salt thereof, wherein:

$R_2$ is $C(O)N(R_k)R_j$;

$R_j$ and $R_k$ are each independently hydrogen or (1-4C)alkyl; and b is 1.

14. The compound of claim 1, or a pharmaceutically acceptable salt thereof, wherein $R_3$ is chloro or bromo.

15. The compound of claim 1, or a pharmaceutically acceptable salt thereof, wherein the compound selectively inhibits RET kinase enzyme activity, or enzyme activity of mutant forms thereof, over KDR enzyme activity in vitro or in vivo, optionally wherein the mutant form is $RET^{V804M}$.

16. A pharmaceutical composition comprising the compound of claim 1, or a pharmaceutically acceptable salt thereof, and a pharmaceutically acceptable carrier or excipient.

17. A compound which is selected from:

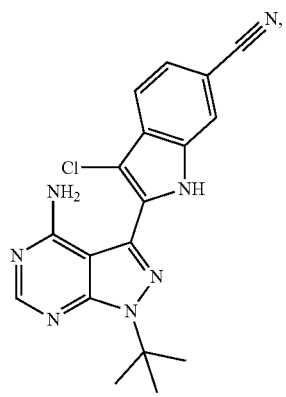

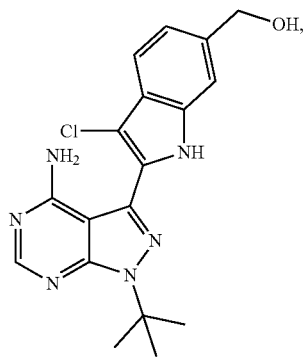

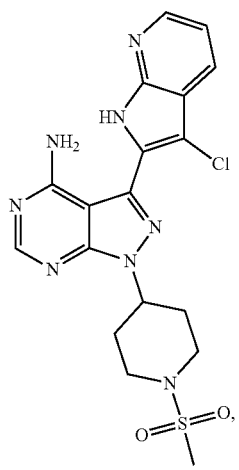

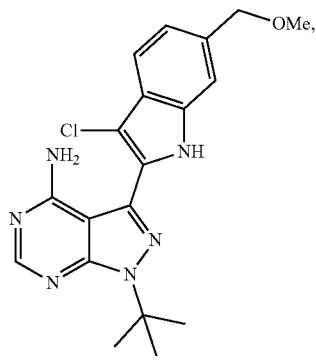

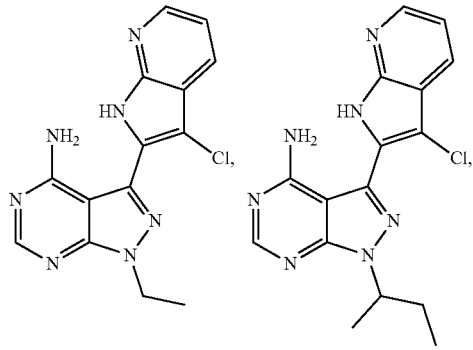

-continued

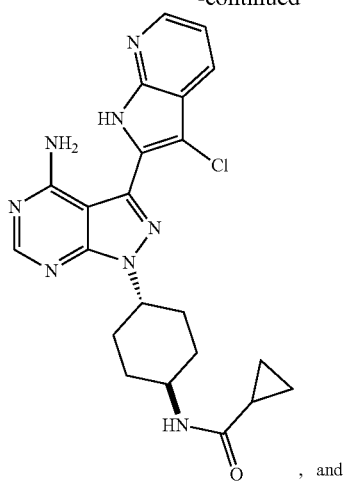

, and

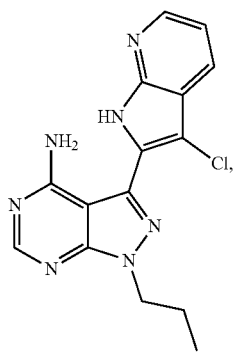

or a pharmaceutically acceptable salt thereof.

18. A method for treatment of a cancer in which RET kinase activity is implicated in a subject in need thereof, comprising administering a therapeutically effective amount of the compound of claim 1, or a pharmaceutically acceptable salt thereof, to the subject.

19. The method of claim 18, wherein the cancer is leukemia, lung cancer, colon cancer, breast cancer, ovarian cancer, prostate cancer, liver cancer, pancreatic cancer, brain cancer, skin cancer, medullary thyroid cancer, or non-small cell lung cancer.

20. The method of claim 18, wherein the cancer comprises a RET mutation.

21. The method of claim 20, wherein the RET mutation is a RET fusion translocation, optionally wherein the RET fusion translocation is KIF5B-RET or CCDC6-RET.

22. The method of claim 20, wherein the RET mutation is a mutation at the RET gatekeeper residue V804, optionally wherein the mutation at the RET gatekeeper residue V804 is $RET^{V804M}$.

23. The method of claim 18, wherein the compound of formula Ib, or a pharmaceutically acceptable salt thereof, inhibits cell proliferation, regulates cell proliferation, inhibits angiogenesis, inhibits metastasis, inhibits invasion of tumor cells into neighboring normal structures, or promotes apoptosis.

24. The method of claim 18, wherein the compound of formula Ib, or a pharmaceutically acceptable salt thereof, selectively inhibits RET kinase enzyme activity, or enzyme activity of mutant forms thereof, over KDR enzyme activity in vitro or in vivo, optionally wherein the mutant form is $RET^{V804M}$.

* * * * *

UNITED STATES PATENT AND TRADEMARK OFFICE
CERTIFICATE OF CORRECTION

PATENT NO. : 11,661,423 B2
APPLICATION NO. : 17/075004
DATED : May 30, 2023
INVENTOR(S) : Allan Michael Jordan et al.

It is certified that error appears in the above-identified patent and that said Letters Patent is hereby corrected as shown below:

In the Claims

In Claim 1, Column 138, Line 32, "Rd" should read --$R_d$--; and

In Claim 12, Column 139, Line 22, "$(CH_2),NR_jR_k$" should read --$(CH_2)_v NR_j R_k$--.

Signed and Sealed this
Twenty-ninth Day of August, 2023

Katherine Kelly Vidal
*Director of the United States Patent and Trademark Office*